US008106176B2

(12) United States Patent
Aurisicchio et al.

(10) Patent No.: US 8,106,176 B2
(45) Date of Patent: Jan. 31, 2012

(54) MATRIX METALLOPROTEINASE 11 VACCINE

(75) Inventors: Luigi Aurisicchio, Rome (IT); Daniela Peruzzi, Pomezia (IT); Nicola La Monica, Rome (IT); Gennaro Ciliberto, Rome (IT); Domenico Lazzaro, Rome (IT); Federica Mori, Pomezia (IT)

(73) Assignee: Instituto di Richerche di Biologia Molecolare P. Angeletti SpA, Rome (IT)

( * ) Notice: Subject to any disclaimer, the term of this patent is extended or adjusted under 35 U.S.C. 154(b) by 380 days.

(21) Appl. No.: 12/083,031

(22) PCT Filed: Oct. 3, 2006

(86) PCT No.: PCT/EP2006/009536
§ 371 (c)(1),
(2), (4) Date: Apr. 3, 2008

(87) PCT Pub. No.: WO2007/042169
PCT Pub. Date: Apr. 19, 2007

(65) Prior Publication Data
US 2009/0155298 A1 Jun. 18, 2009

Related U.S. Application Data

(60) Provisional application No. 60/724,498, filed on Oct. 7, 2005.

(51) Int. Cl.
*C07H 1/00* (2006.01)
*C07H 5/04* (2006.01)
*C07H 5/06* (2006.01)
*C07H 19/00* (2006.01)
*C07H 21/00* (2006.01)
*C07H 21/04* (2006.01)
*C08B 37/00* (2006.01)
*C12P 21/06* (2006.01)
*C12N 5/00* (2006.01)
*C12N 5/02* (2006.01)

(52) U.S. Cl. .............. 536/23.4; 536/1.11; 536/18.7; 536/22.1; 536/23.1; 536/23.2; 536/23.5; 435/69.1; 435/320.1; 435/325

(58) Field of Classification Search .......... 435/69.1, 435/320.1, 325; 536/1.11, 18.7, 22.1, 23.1, 536/23.2, 23.4, 23.5
See application file for complete search history.

(56) References Cited

U.S. PATENT DOCUMENTS 5,786,464 A 7/1998 Seed
6,114,148 A 9/2000 Seed et al.

FOREIGN PATENT DOCUMENTS

WO WO 02/22080 A3 3/2002
WO WO 2004/052301 A2 6/2004
WO WO 2005/077977 A2 8/2005

OTHER PUBLICATIONS

Jones et al, 2004, Clin Cancer Res, 10: 2832-2845.*
Snider, 1995, Crit Rev Immunol, 15(3&4): 317-348.*
Barbacid et al, 1998, Protein expression and Purification, 13:243-250.*
Chamberlain et al. (Expert Opinion on Pharmacotherapy, 1(4): 603-614, 2000).*
Andarawewa, K. et al. "Dual Stromelysin-3 Function during Natural Mouse Mammary Tumor Virus-ras Tumor Progression", Cancer Research, 2003, vol. 63, pp. 5844-5849.
Andarawewa, K. et al. "Stromelysin-3 Is a Potent Negative Regulator of Adipogenesis Participating to Cancer Cell-Adipocyte Interaction/Crosstalk at the Tumor Invasive Front", Cancer Research, 2005, vol. 65, pp. 10862-10871.
Basset, P. et al. "A novel metalloproteinase gene specifically expressed in stomal cells of breast carcinomas", Nature, 1990, vol. 348, pp. 699-704.
Basset, P. et al. "Stromelysin-3: a pardigm for stroma-derived factors implicated in carcinoma progression", Critial Reviews in Oncology/Hematology, 1997, vol. 26, pp. 43-53.
Boulay, A. et al. "High Cancer Cell Death in Syngeneic Tumors Developed in Host Mice Deficient for the Stromelysin-3 Matrix Metalloproteinase", Cancer Research, 2001, vol. 61, pp. 2189-2193.
Damjanovski, S. et al. "Overexpresion of Matrix Metalloproteinases Leads to Lethality in Transgenic *Xenopus laevis*: Implications for Tissue-Dependent Functions of Matrix Metalloproteinases During Late Embryonic Development", Developmental Dynamics, 2001, vol. 221, pp. 37-47.
Deng, H. et al. "Matrix metalloproteinase 11 depletion inhibits cell proliferation in gastric cancer cells", Biochemical and Biophysical Research Communications, 2005, vol. 326, pp. 274-281.
Egeblad, M. et al. "New Functions for the Matrix Metalloproteinases in Cancer Progression", Nature Reviews, 2002, vol. 2, pp. 161-174.
Fromigue, O. et al. "Active Stromelysin-3 (MMP-11) Increases MCF-7 Survival in Three-Dimensional Matrigel Culture Via Activation of p42/p44 Map-Kinase", Int. Journal of Cancer, 2003, vol. 106, pp. 355-363.
Fu, L. et al. "A Causative Role of Stomelysin-3 in Extracellular Matrix Remodelling and Epithelial Apoptosis during Intestinal Metamorphosis in *Xenopus laevis*", The Journal of Biological Chemistry, 2005, vol. 280, pp. 27856-27865.

(Continued)

*Primary Examiner* — Alana H Dent
(74) *Attorney, Agent, or Firm* — Alysia A. Finnegan; Sheldon O. Heber

(57) ABSTRACT

Compositions comprising matrix metalloproteinase 11 (MMP-11) or stromelysin-3 (ST-3) or the nucleic acid encoding the MMP-11 for use in vaccines for treating tumors and cancers, which overexpress MMP-11, are described. In particular embodiments, the compositions comprise a nucleic acid encoding a fusion polypeptide that includes the catalytically inactivated MMP-11 linked at the C-terminus to an immunoenhancing element wherein the codons encoding the MMP-11 and the immunoenhancing element have been optimized for enhanced expression of the fusion polypeptide in human cells. In other embodiments, the compositions comprise the catalytically inactivated MMP-11 linked at the C-terminus to an immunoenhancing element. The compositions can be used alone or in synergy with vaccines against other tumor associated antigens as well as with conventional therapies such as radiation therapy and chemotherapy.

9 Claims, 21 Drawing Sheets

OTHER PUBLICATIONS

Fuglsang, A. "Codon optimizer: a freeware tool for codon optimization", Protein Expression and Purification, 2003, vol. 31, pp. 247-249.

Jones, L. et al. "Comprehensive Analysis of Matrix Metalloproteinase and Tissue Inhibitor Expression in Pancreatic Cancer: Increased Expression of Matrix Metalloproteinase-7 Predicts Poor Survival", Clinical Cancer Research, 2004, vol. 10, pp. 2832-2845.

Kataoka, H. et al. "Enhanced Tumor Growth and Invasiveness in Vivo by a Carboxyl-Terminal Fragment of αl-Proteinase Inhibitor Generated by Matrix Metalloproteinases", American Journal of Pathology, 1999, vol. 154, pp. 457-468.

Lathe, R. "Synthetic Oligonucleotide Probes Deduced from Amino Acid Sequence Data Theoretical and Practical Considerations", Journal of Molecular Biology, 1985, vol. 183, pp. 1-12.

Mari, B. et al. "Stromelysin-3 Is Induced in Tumor/Stroma Cocultures and Inactivated via a Tumor-specific and Basic Fibroblast Growth Factor-dependent Mechanism", The Journal of Biological Chemistry, 1998, vol. 273, pp. 618-626.

Masson, R. et al. "In Vivo Evidence That the Stromelysin-3 Metalloproteinase Contributes in a Paracrine Manner to Epithelial Cell Malignancy", The Journal of Cell Biology, 1998, vol. 140, pp. 1535-1541.

Montgomery, D. et al. "Heterologous and Homologous Protection Against Influenza A by DNA Vaccination: Optimization of DNA Vectors", DNA and Cell Biology, 1993, vol. 12, pp. 777-783.

Nakamura, Y. et al. Codon usage tabulated from international DNA sequence databases: status for the year 2000, Nucleic Acids Research, 2000, vol. 28, pp. 292.

Noel, A. et al. "Demonstration in vivo that stromelysin-3 functions through its proteolytic activity", Oncogene, 2000, vol. 19, pp. 1605-1612.

Noel, A. et al. "Stromelysin-3 Expression Promotes Tumor Take in Nude Mice", The Journal of Clinical Investigation, 1996, vol. 97, pp. 1924-1930.

Thewes, M. et al. "Stromelysin-3 (ST-3) mRNA Expression in Colorectal Carcinomas", Diagnostic Molecular Pathology, 1996, vol. 5, pp. 284-190.

Wu, E. et al. "Stromelysin-3 Suppresses Tumor Cell Apoptosis in a Murine Model", Journal of Cellular Biochemistry, 2001, vol. 82, pp. 549-555.

Accession No. NM_008606, Feb. 11, 2008.

Chenard et al., "High Levels of Stromelysin-3 Correlate with Poor Prognosis in Patients with Breast Carcinoma", Int. J. Cancer (Pred. Oncol.), 1996, vol. 69, pp. 448-451.

* cited by examiner

```
   1 CTGCAGAGAT CTGGTACCGA TATCGCCACC ATGGCCAGAG CCGCCTGCCT
     GCTGAGAGCC ATCAGCAGAG TGCTGCTGCT GCCTCTGCCA CTGCTGCTCC
 101 TGTTGCTGCT CCTGCTGCCT AGCCCTCTGA TGGCCAGAGC TAGGCCTCCT
     GAGAGCCACA GACACCACCC TGTGAAGAAG GGCCCTAGAC TGCTGCACGC
 201 CGCCCTGCCT AACACCCTGA CCAGCGTGCC TGCCAGCCAC TGGGTGCCAA
     GCCCTGCCGG CAGCAGCAGA CCTCTGAGAT GTGGCGTGCC TGACCTGCCT
 301 GACGTGCTGA ACGCCAGGAA CAGGCAGAAG CGGTTCGTGC TGAGCGGCGG
     CAGATGGGAA AAGACCGACC TGACCTACAG GATCCTGAGA TTCCCCTGGC
 401 AGCTGGTGCG TGAGCAAGTG CGTCAGACCG TGGCCGAGGC CCTCCAGGTG
     TGGAGCGAGG TGACCCCTCT GACCTTCACC GAGGTGCACG AGGGCAGAGC
 501 CGACATCATG ATCGACTTCG CCAGATACTG GCACGGCGAC AACCTGCCTT
     TCGACGGCCC TGGCGGCATC CTGGCCCACG CCTTTTTCCC CAAGACCCAC
 601 AGAGAGGGCG ACGTGCACTT CGACTACGAC GAGACCTGGA CCATCGGCGA
     TAACCAGGGC ACCGACCTGC TCCAGGTGGC CGCCCACGCT TTCGGCCACG
 701 TGCTGGGCCT CCAGCACACC ACCGCCGCCA AGGCCCTGAT GAGCCCCTTC
     TACACCTTCA GATACCCCCT GAGCCTGAGC CCTGACGACA GAAGAGGCAT
 801 CCAGCACCTG TACGGCAGAC CTCAGATGGC CCCTACCAGC CCTGCCCCTA
     CCCTGAGCAG CCAGGCCGGC ACCGACACCA ACGAGATCGC CCTGCTGGAG
 901 CCTGAGACCC CTCCTGATGT GTGCGAGACC AGCTTCGACG CCGTGTCTAC
     CATCAGAGGC GAGCTGTTCT TCTTCAAGGC CGGCTTTGTG TGGAGACTGA
1001 GGAGCGGCAG ACTCCAGCCT GGCTACCCTG CCCTGGCCAG CAGACACTGG
     CAGGGCCTGC CTTCCCCTGT GGACGCCGCC TTCGAGGACG CCCAGGGCCA
1101 GATTTGGTTC TTCCAGGGCG CCCAGTACTG GGTGTACGAC GGCGAGAAGC
     CTGTGCTGGG CCCTGCCCCA CTGAGCAAGC TGGGACTCCA GGGCAGCCCT
1201 GTGCACGCTG CCCTGGTGTG GGGACCTGAA AAGAACAAAA TCTATTTCTT
     CAGAGGCGGC GACTACTGGA GATTCCACCC CAGGACCCAG AGAGTGGACA
1301 ACCCCGTGCC CAGAAGAAGC ACCGACTGGA GAGGCGTGCC TAGCGAGATC
     GACGCCGCTT TCCAGGATGC TGAGGGCTAC GCCTACTTCC TGAGGGGCCA
1401 CCTGTACTGG AAGTTCGACC CCGTGAAGGT GAAGGTGCTG GAGGGCTTCC
     CTAGACCTGT GGGCCCTGAC TTCTTCGACT GCGCCGAGCC TGCCAACACC
1501 TTCCGGTCTA GATGATAAGT GACTAAATGA GAATTCGTCG ACGCGGCCGC
     CGGCGGTAGT CGTACCTCTT AACTATTAGA TCTACTATTC ACTGATTTAC
1601 TCTTAAGCAG CTGCGCCGGC G
```

FIG.3

```
   1  CTGCAGAGAT CTGGTACCGA TATCGCCACC ATGGCCAGAG CCGCCTGCCT
      GCTGAGAGCC ATCAGCAGAG TGCTGCTGCT GCCTCTGCCA CTGCTGCTCC
 101  TGTTGCTGCT CCTGCTGCCT AGCCCTCTGA TGGCCAGAGC TAGGCCTCCT
      GAGAGCCACA GACACCACCC TGTGAAGAAG GGCCCTAGAC TGCTGCACGC
 201  CGCCCTGCCT AACACCCTGA CCAGCGTGCC TGCCAGCCAC TGGGTGCCAA
      GCCCTGCCGG CAGCAGCAGA CCTCTGAGAT GTGGCGTGCC TGACCTGCCT
 301  GACGTGCTGA ACGCCAGGAA CAGGCAGAAG CGGTTCGTGC TGAGCGGCGG
      CAGATGGGAA AAGACCGACC TGACCTACAG GATCCTGAGA TTCCCCTGGC
 401  AGCTGGTGCG TGAGCAAGTG CGTCAGACCG TGGCCGAGGC CCTCCAGGTG
      TGGAGCGAGG TGACCCCTCT GACCTTCACC GAGGTGCACG AGGGCAGAGC
 501  CGACATCATG ATCGACTTCG CCAGATACTG GCACGGCGAC AACCTGCCTT
      TCGACGGCCC TGGCGGCATC CTGGCCCACG CCTTTTTCCC CAAGACCCAC
 601  AGAGAGGGCG ACGTGCACTT CGACTACGAC GAGACCTGGA CCATCGGCGA
      TAACCAGGGC ACCGACCTGC TCCAGGTGGC CGCCCACGCT TTCGGCCACG
 701  TGCTGGGCCT CCAGCACACC ACCGCCGCCA AGGCCCTGAT GAGCCCCTTC
      TACACCTTCA GATACCCCCT GAGCCTGAGC CCTGACGACA GAAGAGGCAT
 801  CCAGCACCTG TACGGCAGAC CTCAGATGGC CCCTACCAGC CCTGCCCCTA
      CCCTGAGCAG CCAGGCCGGC ACCGACACCA ACGAGATCGC CCTGCTGGAG
 901  CCTGAGACCC CTCCTGATGT GTGCGAGACC AGCTTCGACG CCGTGTCTAC
      CATCAGAGGC GAGCTGTTCT TCTTCAAGGC CGGCTTTGTG TGGAGACTGA
1001  GGAGCGGCAG ACTCCAGCCT GGCTACCCTG CCCTGGCCAG CAGACACTGG
      CAGGGCCTGC CTTCCCCTGT GGACGCCGCC TTCGAGGACG CCCAGGGCCA
1101  GATTTGGTTC TTCCAGGGCG CCCAGTACTG GGTGTACGAC GGCGAGAAGC
      CTGTGCTGGG CCCTGCCCCA CTGAGCAAGC TGGGACTCCA GGGCAGCCCT
1201  GTGCACGCTG CCCTGGTGTG GGGACCTGAA AAGAACAAAA TCTATTTCTT
      CAGAGGCGGC GACTACTGGA GATTCCACCC CAGGACCCAG AGAGTGGACA
1301  ACCCCGTGCC CAGAAGAAGC ACCGACTGGA GAGGCGTGCC TAGCGAGATC
      GACGCCGCTT TCCAGGATGC TGAGGGCTAC GCCTACTTCC TGAGGGGCCA
1401  CCTGTACTGG AAGTTCGACC CCGTGAAGGT GAAGGTGCTG GAGGGCTTCC
      CTAGACCTGT GGGCCCTGAC TTCTTCGACT GCGCCGAGCC TGCCAACACC
1501  TTCCGGTCTA GAgcccccca gagcatcacc gagctgtgca gcgagtaccg
      gaacacccag atttacacca tcaacgacaa gatcctgagc tacaccgaga
1601  gcatggccgg caagagggag atggtgatca tcaccttcaa gagcggcgcc
      accttccagg tggaggtgcc cggcagccag cacatcgaca gccagaagaa
1701  ggccatcgag cggatgaagg acaccctgcg gatcacctac ctcaccgaga
      ccaagatcga caagctgtgc gtgtgggaca acaagacccc caacagcatc
1801  gccgccatca gcatggagaa tTGATAATCT AGATGATAAG TGACTAAATG
      AGAATTCGTC GACGCGGCCG CCGGCGGTAG TCGTACCTCT TAACTATTAGA
1901  TCTACTATTC ACTGATTTAC TCTTAAGCAG CTGCGCCGGC G
```

FIG.4

```
  1  MARAACLLRA ISRVLLLPLP LLLLLLLLLP SPLMARARPP ESHRHHPVKK
 51  GPRLLHAALP NTLTSVPASH WVPSPAGSSR PLRCGVPDLP DVLNARNRQK
101  RFVLSGGRWE KTDLTYRILR FPWQLVREQV RQTVAEALQV WSEVTPLTFT
151  EVHEGRADIM IDFARYWHGD NLPFDGPGGI LAHAFFPKTH REGDVHFDYD
201  ETWTIGDNQG TDLLQVAAHA FGHVLGLQHT TAAKALMSPF YTFRYPLSLS
251  PDDRRGIQHL YGRPQMAPTS PAPTLSSQAG TDTNEIALLE PETPPDVCET
301  SFDAVSTIRG ELFFFKAGFV WRLRSGRLQP GYPALASRHW QGLPSPVDAA
351  FEDAQGQIWF FQGAQYWVYD GEKPVLGPAP LSKLGLQGSP VHAALVWGPE
401  KNKIYFFRGG DYWRFHPRTQ RVDNPVPRRS TDWRGVPSEI DAAFQDAEGY
451  AYFLRGHLYW KFDPVKVKVL EGFPRPVGPD FFDCAEPANT FRSRAPQSIT
501  ELCSEYRNTQ IYTINDKILS YTESMAGKRE MVIITFKSGA TFQVEVPGSQ
551  HIDSQKKAIE RMKDTLRITY LTETKIDKLC VWNNKTPNSI AAISMEN
```

FIG.5

```
   1  ATGGCTCCTG CCGCCTGGCT GAGAAGCGCT GCCGCTAGAG CCCTGCTGCC
      CCCTATGCTG CTGCTCCTGC TGCAGCCTCC TCCTCTGCTG GCTCGGGCTC
 101  TGCCTCCTGA CGTGCACCAC CTGCATGCCG AGAGGAGGGG GCCACAGCCC
      TGGCATGCTG CCCTGCCCAG TAGCCCTGCT CCTGCCCCTG CCACACAGGA
 201  AGCCCCCAGA CCTGCCAGCA GCCTGAGGCC TCCCAGATGT GGCGTGCCCG
      ACCCATCTGA TGGGCTGAGT GCCCGCAACC GGCAGAAGAG ATTCGTGCTG
 301  TCTGGCGGAC GCTGGGAGAA AACCGACCTG ACCTACAGGA TCCTGCGGTT
      CCCATGGCAG CTGGTGCAGG AACAGGTGCG GCAGACAATG GCTGAGGCCC
 401  TGAAAGTGTG GAGCGATGTG ACCCCACTGA CCTTTACTGA AGTGCACGAG
      GGCAGGGCTG ACATCATGAT CGACTTCGCC CGGTACTGGC ATGGGGACGA
 501  CCTGCCTTTT GATGGGCCTG GGGGCATCCT GGCCCATGCC TTCTTCCCCA
      AAACTCACCG GGAAGGGGAT GTGCACTTCG ACTATGATGA GACCTGGACT
 601  ATCGGGGATG ACCAGGGCAC AGACCTGCTG CAGGTGGCCG CCCATGTGTT
      TGGCCACGTG CTGGGGCTGC AGCACACAAC AGCTGCCAAG GCCCTGATGT
 701  CCGCCTTCTA CACCTTTCGC TACCCACTGA GTCTGAGCCC AGATGACTGC
      AGGGGCGTGC AGCACCTGTA TGGCCAGCCC TGGCCCACTG TGACCTCCAG
 801  GACCCCAGCC CTGGGCCCCC AGGCTGGGAT TGACACCAAT GAGATTGCCC
      CCCTGGAGCC AGACGCCCCT CCAGATGCCT GTGAGGCCTC CTTTGACGCC
 901  GTGTCCACCA TCAGAGGCGA GCTGTTTTTC TTCAAGGCCG GCTTTGTGTG
      GAGACTGAGA GGGGGCCAGC TGCAGCCCGG CTACCCAGCT CTGGCCTCTC
1001  GCCACTGGCA GGGACTGCCC AGCCCTGTGG ACGCTGCCTT CGAGGATGCC
      CAGGGCCACA TTTGGTTCTT CCAGGGCGCT CAGTACTGGG TGTACGACGG
1101  CGAAAAGCCA GTGCTGGGCC CTGCTCCCCT GACCGAGCTG GGCCTGGTGA
      GATTCCCAGT GCATGCCGCC CTGGTGTGGG ACCCGAGAA GAACAAAATC
1201  TACTTCTTCC GGGGCAGGGA CTACTGGAGA TTCCACCCCA GCACCCGGAG
      AGTGGACAGT CCCGTGCCCA GAAGGGCCAC TGACTGGAGA GGAGTGCCCT
1301  CTGAGATCGA CGCCGCCTTC CAGGACGCTG ATGGCTATGC CTACTTCCTG
      CGCGGCAGGC TGTACTGGAA GTTTGACCCT GTGAAAGTGA AGGCTCTGGA
1401  AGGCTTCCCC AGACTGGTGG GCCCTGACTT CTTTGGCTGT GCCGAGCCTG
      CCAACACTTT CCTGTGATAA
```

FIG. 14

```
  1  MAPAAWLRSA AARALLPPML LLLLQPPPLL ARALPPDVHH LHAERRGPQP
 51  WHAALPSSPA PAPATQEAPR PASSLRPPRC GVPDPSDGLS ARNRQKRFVL
101  SGGRWEKTDL TYRILRFPWQ LVQEQVRQTM AEALKVWSDV TPLTFTEVHE
151  GRADIMIDFA RYWHGDDLPF DGPGGILAHA FFPKTHREGD VHFDYDETWT
201  IGDDQGTDLL QVAAHVFGHV LGLQHTTAAK ALMSAFYTFR YPLSLSPDDC
251  RGVQHLYGQP WPTVTSRTPA LGPQAGIDTN EIAPLEPDAP PDACEASFDA
301  VSTIRGELFF FKAGFVWRLR GGQLQPGYPA LASRHWQGLP SPVDAAFEDA
351  QGHIWFFQGA QYWVYDGEKP VLGPAPLTEL GLVRFPVHAA LVWGPEKNKI
401  YFFRGRDYWR FHPSTRRVDS PVPRRATDWR GVPSEIDAAF QDADGYAYFL
451  RGRLYWKFDP VKVKALEGFP RLVGPDFFGC AEPANTFL
```

FIG. 15

ATGGCTCCTGCCGCCTGGCTGAGAAGCGCTGCCGCTAGAGCCCTGCTGCCCCCTAT
GCTGCTGCTCCTGCTGCAGCCTCCTCCTCTGCTGGCTCGGGCTCTGCCTCCTGACG
TGCACCACCTGCATGCCGAGAGGAGGGGGCCACAGCCCTGGCATGCTGCCCTGCCC
AGTAGCCCTGCTCCTGCCCCTGCCACACAGGAAGCCCCCAGACCTGCCAGCAGCCT
GAGGCCTCCCAGATGTGGCGTGCCCGACCCATCTGATGGGCTGAGTGCCCGCAACC
GGCAGAAGAGATTCGTGCTGTCTGGCGGACGCTGGGAGAAAACCGACCTGACCTAC
AGGATCCTGCGGTTCCCATGGCAGCTGGTGCAGGAACAGGTGCGGCAGACAATGGC
TGAGGCCCTGAAAGTGTGGAGCGATGTGACCCCACTGACCTTTACTGAAGTGCACG
AGGGCAGGGCTGACATCATGATCGACTTCGCCCGGTACTGGCATGGGGACGACCTG
CCTTTTGATGGGCCTGGGGGCATCCTGGCCCATGCCTTCTTCCCCAAAACTCACCG
GGAAGGGGATGTGCACTTCGACTATGATGAGACCTGGACTATCGGGGATGACCAGG
GCACAGACCTGCTGCAGGTGGCCGCCCATGTGTTTGGCCACGTGCTGGGGCTGCAG
CACACAACAGCTGCCAAGGCCCTGATGTCCGCCTTCTACACCTTTCGCTACCCACT
GAGTCTGAGCCCAGATGACTGCAGGGGCGTGCAGCACCTGTATGGCCAGCCCTGGC
CCACTGTGACCTCCAGGACCCCAGCCCTGGGCCCCCAGGCTGGGATTGACACCAAT
GAGATTGCCCCCCTGGAGCCAGACGCCCCTCCAGATGCCTGTGAGGCCTCCTTTGA
CGCCGTGTCCACCATCAGAGGCGAGCTGTTTTTCTTCAAGGCCGGCTTTGTGTGGA
GACTGAGAGGGGGCCAGCTGCAGCCCGGCTACCCAGCTCTGGCCTCTCGCCACTGG
CAGGGACTGCCCAGCCCTGTGGACGCTGCCTTCGAGGATGCCCAGGGCCACATTTG
GTTCTTCCAGGGCGCTCAGTACTGGGTGTACGACGGCGAAAAGCCAGTGCTGGGCC
CTGCTCCCCTGACCGAGCTGGGCCTGGTGAGATTCCCAGTGCATGCCGCCCTGGTG
TGGGGACCCGAGAAGAACAAAATCTACTTCTTCCGGGGCAGGGACTACTGGAGATT
CCACCCCAGCACCCGGAGAGTGGACAGTCCCGTGCCCAGAAGGGCCACTGACTGGA
GAGGAGTGCCCTCTGAGATCGACGCCGCCTTCCAGGACGCTGATGGCTATGCCTAC
TTCCTGCGCGGCAGGCTGTACTGGAAGTTTGACCCTGTGAAAGTGAAGGCTCTGGA
AGGCTTCCCCAGACTGGTGGGCCCTGACTTCTTTGGCTGTGCCGAGCCTGCCAACA
CTTTCCTGTCTAGAgccccccagagcatcaccgagctgtgcagcgagtaccggaac
Acccagatttacaccatcaacgacaagatcctgagctacaccgagagcatggccgg
Caagagggagatggtgatcatcaccttcaagagcggcgccaccttccaggtggagg
Tgcccggcagccagcacatcgacagccagaagaaggccatcgagcggatgaaggac
Accctgcggatcacctacctcaccgagaccaagatcgacaagctgtgcgtgtggaa
caacaagaccccaacagcatcgccgccatcagcatggagaattgataa MAPAAWLRSA AARALLPPML LLLLQPPPLL ARALPPDVHH LHAERRGPQP
WHAALPSSPA PAPATQEAPR PASSLRPPRC GVPDPSDGLS ARNRQKRFVL
SGGRWEKTDL TYRILRFPWQ LVQEQVRQTM AEALKVWSDV TPLTFTEVHE
GRADIMIDFA RYWHGDDLPF DGPGGILAHA FFPKTHREGD VHFDYDETWT
IGDDQGTDLL QVAAHVFGHV LGLQHTTAAK ALMSAFYTFR YPLSLSPDDC
RGVQHLYGQP WPTVTSRTPA LGPQAGIDTN EIAPLEPDAP PDACEASFDA
VSTIRGELFF FKAGFVWRLR GGQLQPGYPA LASRHWQGLP SPVDAAFEDA
QGHIWFFQGA QYWVYDGEKP VLGPAPLTEL GLVRFPVHAA LVWGPEKNKI
YFFRGRDYWR FHPSTRRVDS PVPRRATDWR GVPSEIDAAF QDADGYAYFL
RGRLYWKFDP VKVKALEGFP RLVGPDFFGC AEPANTFLSR APQSITELCS
EYRNTQIYTI NDKILSYTES MAGKREMVII TFKSGATFQV EVPGSQHIDS
QKKAIERMKD TLRITYLTET KIDKLCVWNN KTPNSIAAIS MEN

FIG. 17

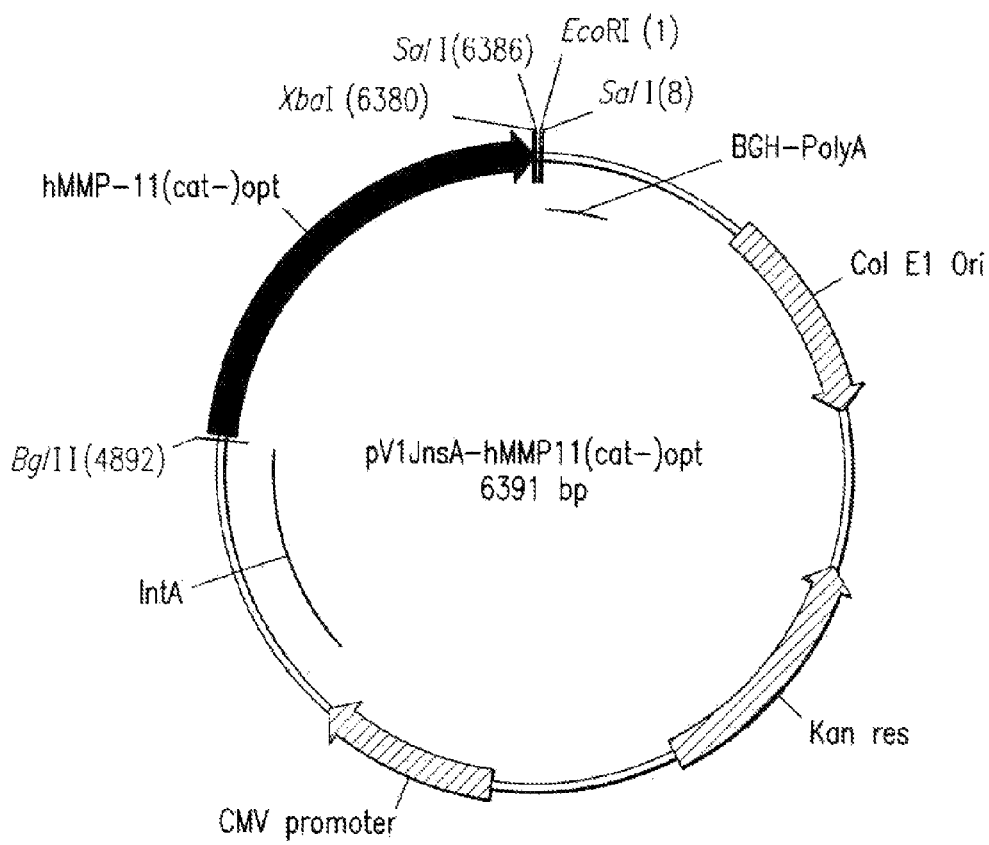

FIG. 18

SEQUENCE LISTING

<160> NUMBER OF SEQ ID NOS: 17

<210> SEQ ID NO 1
<211> LENGTH: 1467
<212> TYPE: DNA
<213> ORGANISM: Homo Sapiens

<400> SEQUENCE: 1

```
atggctccgg ccgcctggct ccgcagcgcg gccgcgcgcg ccctcctgcc cccgatgctg      60
ctgctgctgc tccagccgcc gccgctgctg gcccgggctc tgccgccgga cgccaccac     120 ctccatgccg agaggagggg gccacagccc tggcatgcag ccctgcccag tagcccggca     180
cctgcccctg ccacgcagga agccccccgg cctgccagca gcctcaggcc tccccgctgt     240
ggcgtgcccg acccatctga tgggctgagt gcccgcaacc gacagaagag gttcgtgctt     300
tctggcgggc gctgggagaa gacggacctc acctacagga tccttcggtt cccatggcag     360
ttggtgcagg agcaggtgcg gcagacgatg gcagaggccc taaaggtatg gagcgatgtg     420
acgccactca cctttactga ggtgcacgag ggccgtgctg acatcatgat cgacttcgcc     480
aggtactggc atgggacga cctgccgttt gatgggcctg ggggcatcct ggcccatgcc     540
ttcttcccca agactcaccg agaaggggat gtccacttcg actatgatga cctggact      600 atcggggatg accagggcac agacctgctg caggtggcag cccatgaatt tggccacgtg     660
ctggggctgc agcacacaac agcagccaag gccctgatgt ccgccttcta cacctttcgc     720
tacccactga gtctcagccc agatgactgc aggggcgttc aacacctata tggccagccc     780
tggcccactg tcacctccag gacccagcc ctgggccccc aggctgggat agacaccaat     840
gagattgcac cgctggagcc agacgccccg ccagatgcct gtgaggcctc ctttgacgcg     900
gtctccacca tccgaggcga gctcttttc ttcaaagcgg gctttgtgtg gcgcctccgt     960
gggggccagc tgcagcccgg ctacccagca ttggcctctc gccactggca gggactgccc    1020
agccctgtgg acgctgcctt cgaggatgcc cagggccaca tttggttctt caaggtgct    1080 cagtactggg tgtacgacga tgaaaagcca gtcctgggcc ccgcacccct caccgagctg    1140
ggcctggtga ggttcccggt ccatgctgcc ttggtctggg gtcccgagaa gaacaagatc    1200
tacttcttcc gaggcaggga ctactggcgt ttccacccca gcacccggcg tgtagacagt    1260
cccgtgcccc gcagggccac tgactggaga ggggtgccct ctgagatcga cgctgccttc    1320
caggatgctg atggctatgc ctacttcctg cgcggccgcc tctactggaa gtttgaccct    1380
gtgaaggtga aggctctgga aggcttcccc cgtctcgtgg gtcctgactt ctttggctgt    1440
```

```
gccgagcctg ccaacacttt cctctga                                       1467

<210> SEQ ID NO 2
<211> LENGTH: 6717
<212> TYPE: DNA
<213> ORGANISM: Artificial Sequence
<220> FEATURE:
<223> OTHER INFORMATION: pV1JnsA-MMP-11(cat-1)-LTBopt
<220> FEATURE:
<221> NAME/KEY: misc_feature
<222> LOCATION: 357, 366, 5234
<223> OTHER INFORMATION: n = a, t, c or g

<400> SEQUENCE: 2
ctagagcccc ccagagcatc accgagctgt gcagcgagta ccggaacacc cagatttaca     60
ccatcaacga caagatcctg agctacaccg agagcatggc cggcaagagg gagatggtga    120
tcatcacctt caagagcggc gccaccttcc aggtggaggt gcccggcagc cagcacatcg    180
acagccagaa aaaggccatc gagcggatga aggacaccct gcggatcacc tacctcaccg    240
agaccaagat cgacaagctg tgcgtgtgga caacaagac ccccaacagc atcgccgcca    300
tcagcatgga gaattgataa tctagatgat aagtgactaa atgagaattc gtcgacngcg    360
gccgcngatc tgctgtgcct tctagttgcc agccatctgt gtttgcccc tcccccgtgc    420
cttccttgac cctggaaggt gccactccca ctgtcctttc ctaataaaat gaggaaattg    480
catcgcattg tctgagtagg tgtcattcta ttctgggggg tggggtgggg caggacagca    540
agggggagga ttgggaagac aatagcaggc atgctgggga tcggtgggc tctatggccg    600
cagcggccag gtgctgaaga attgacccgg ttcctcctgg ccagaaaga agcaggcaca    660
tccccttctc tgtgacacac cctgtccacg ccctggttc ttagttccag ccccactcat    720
aggacactca tagctcagga gggctccgcc ttcaatccca cccgctaaag tacttggagc    780
ggtctctccc tccctcatca gcccaccaaa ccaaacctag cctccaagag tgggaagaaa    840
ttaaagcaag ataggctatt aagtgcagag ggagagaaaa tgcctccaac atgtgaggaa    900
gtaatgagag aaatcataga atttcttccg cttcctcgct cactgactcg ctgcgctcgg    960
tcgttcggct gcggcgagcg gtatcagctc actcaaaggc ggtaatacgg ttatccacag   1020
aatcagggga taacgcagga agaacatgt gagcaaaagg ccagcaaaag gccaggaacc   1080
gtaaaaaggc cgcgttgctg gcgttttttcc ataggctccg cccccctgac gagcatcaca   1140
aaaatcgacg ctcaagtcag aggtggcgaa acccgacagg actataaaga taccaggcgt   1200
ttcccctggg aagctccctc gtgcgctctc ctgttccgac cctgccgctt accggatacc   1260
tgtccgcctt tctcccttcg ggaagcgtgg cgctttctca tagctcacgc tgtaggtatc   1320
tcagttcggt gtaggtcgtt cgctccaagc tgggctgtgt gcacgaaccc cccgttcagc   1380
ccgaccgctg cgccttatcc ggtaactatc gtcttgagtc caacccggta agacacgact   1440
tatcgccact ggcagcagcc actggtaaca ggattagcag agcgaggtat gtaggcggtg   1500
ctacagagtt cttgaagtgg tggcctaact acggctacac tagaagaaca gtatttggta   1560
tctgcgctct gctgaagcca gttaccttcg gaaaaagagt tggtagctct tgatccggca   1620
aacaaaccac cgctggtagc ggtggttttt tgtttgcaa gcagcagatt acgcgcagaa   1680
aaaaaggatc tcaagaagat cctttgatct tttctacggg gtctgacgct cagtggaacg   1740
aaaactcacg ttaagggatt ttggtcatga gattatcaaa aaggatcttc acctagatcc   1800
ttttaaatta aaaatgaagt tttaaatcaa tctaaagtat atatgagtaa acttggtctg   1860
acagttacca atgcttaatc agtgaggcac ctatctcagc gatctgtcta tttcgttcat   1920
```

```
ccatagttgc ctgactcggg ggggggggc gctgaggtct gcctcgtgaa aaggtgttg    1980 ctgactcata ccaggcctga atcgccccat catccagcca gaaagtgagg gagccacggt    2040
tgatgagagc tttgttgtag gtggaccagt tggtgatttt gaacttttgc tttgccacgg    2100
aacggtctgc gttgtcggga agatgcgtga tctgatcctt caactcagca aaagttcgat    2160
ttattcaaca aagccgccgt cccgtcaagt cagcgtaatg ctctgccagt gttacaacca    2220
attaaccaat tctgattaga aaaactcatc gagcatcaaa tgaaactgca atttattcat    2280
atcaggatta tcaataccat attttttgaaa aagccgtttc tgtaatgaag gagaaaactc    2340
accgaggcag ttccatagga tggcaagatc ctggtatcgg tctgcgattc cgactcgtcc    2400
aacatcaata caacctatta atttcccctc gtcaaaaata aggttatcaa gtgagaaatc    2460
accatgagtg acgactgaat ccggtgagaa tggcaaaagc ttatgcattt ctttccagac    2520
ttgttcaaca ggccagccat tacgctcgtc atcaaaatca ctcgcatcaa ccaaaccgtt    2580
attcattcgt gattgcgcct gagcgagacg aaatacgcga tcgctgttaa aaggacaatt    2640
acaaacagga atcgaatgca accggcgcag gaacactgcc agcgcatcaa caatatttc    2700 acctgaatca ggatattctt ctaatacctg gaatgctgtt ttcccgggga tcgcagtggt    2760
gagtaaccat gcatcatcag gagtacggat aaaatgcttg atggtcggaa gaggcataaa    2820
ttccgtcagc cagtttagtc tgaccatctc atctgtaaca tcattggcaa cgctacccttt    2880 gccatgtttc agaaacaact ctggcgcatc gggcttccca tacaatcgat agattgtcgc    2940
acctgattgc ccgacattat cgcgagccca tttatacccca tataaatcag catccatgtt    3000
ggaatttaat cgcggcctcg agcaagacgt ttcccgttga atatggctca taacacccct    3060
tgtattactg tttatgtaag cagacagttt tattgttcat gatgatatat ttttatcttg    3120
tgcaatgtaa catcagagat tttgagacac aacgtggctt tccccccccc cccattattg    3180
aagcatttat cagggttatt gtctcatgag cggatacata tttgaatgta tttagaaaaa    3240
taaacaaata ggggttccgc gcacatttcc ccgaaaagtg ccacctgacg tctaagaaac    3300
cattattatc atgacattaa cctataaaaa taggcgtatc acgaggccct ttcgtctcgc    3360
gcgtttcggt gatgacggtg aaaacctctg acacatgcag ctcccggaga cggtcacagc    3420
ttgtctgtaa gcggatgccg ggagcagaca agcccgtcag ggcgcgtcag cgggtgttgg    3480
cgggtgtcgg ggctggctta actatgcggc atcagagcag attgtactga gagtgcacca    3540
tatgcggtgt gaaataccgc acagatgcgt aaggagaaaa taccgcatca gattggctat    3600
tggccattgc atacgttgta tccatatcat aatatgtaca tttatattgg ctcatgtcca    3660
acattaccgc catgttgaca ttgattattg actagttatt aatagtaatc aattacgggg    3720
tcattagttc atagcccata tatggagttc cgcgttacat aacttacggt aaatggcccg    3780
cctggctgac cgcccaacga ccccgcccca ttgacgtcaa taatgacgta tgttcccata    3840
gtaacgccaa tagggacttt ccattgacgt caatgggtgg agtatttacg gtaaactgcc    3900
cacttggcag tacatcaagt gtatcatatg ccaagtacgc cccctattga cgtcaatgac    3960
ggtaaatggc ccgcctggca ttatgcccag tacatgacct tatgggactt tcctacttgg    4020
cagtacatct acgtattagt catcgctatt accatggtga tgcggttttg gcagtacatc    4080
aatgggcgtg gatagcggtt tgactcacgg ggatttccaa gtctccaccc cattgacgtc    4140
aatgggagtt tgttttggca ccaaaatcaa cgggactttc caaaatgtcg taacaactcc    4200
gccccattga cgcaaatggg cggtaggcgt gtacggtggg aggtctatat aagcagagct    4260
cgtttagtga accgtcagat cgcctggaga cgccatccac gctgttttga cctccataga    4320
```

```
agacaccggg accgatccag cctccgcggc cgggaacggt gcattggaac gcggattccc   4380
cgtgccaaga gtgacgtaag taccgcctat agactctata ggcacacccc tttggctctt   4440
atgcatgcta tactgttttt ggcttggggc ctatacaccc ccgcttcctt atgctatagg   4500
tgatggtata gcttagccta taggtgtggg ttattgacca ttattgacca ctcccctatt   4560
ggtgacgata ctttccatta ctaatccata acatggctct tgccacaac tatctctatt    4620
ggctatatgc caatactctg tccttcagag actgacacgg actctgtatt tttacaggat   4680
ggggtcccat ttattattta caaattcaca tatacaacaa cgccgtcccc cgtgcccgca   4740
gtttttatta aacatagcgt gggatctcca cgcgaatctc gggtacgtgt tccggacatg   4800
ggctcttctc cggtagcggc ggagcttcca catccgagcc ctggtcccat gcctccagcg   4860
gctcatggtc gctcggcagc tccttgctcc taacagtgga ggccagactt aggcacagca   4920
caatgcccac caccaccagt gtgccgcaca aggccgtggc ggtagggtat gtgtctgaaa   4980
atgagcgtgg agattgggct cgcacggctg acgcagatgg aagacttaag gcagcggcag   5040
aagaagatgc aggcagctga gttgttgtat tctgataaga gtcagaggta actcccgttg   5100
cggtgctgtt aacggtggag ggcagtgtag tctgagcagt actcgttgct gccgcgcgcg   5160
ccaccagaca taatagctga cagactaaca gactgttcct ttccatgggt cttttctgca   5220
gtcaccgtcc ttanagatct gatatcgcca ccatggctcc tgccgcctgg ctgagaagcg   5280
ctgccgctag agccctgctg cccctatgc tgctgctcct gctgcagcct cctcctctgc    5340
tggctcgggc tctgcctcct gacgtgcacc acctgcatgc cgagaggagg gggccacagc   5400
cctggcatgc tgccctgccc agtagccctg ctcctgcccc tgccacacag gaagccccca   5460
gacctgccag cagcctgagg cctcccagat gtggcgtgcc cgacccatct gatgggctga   5520
gtgcccgcaa ccggcagaag agattcgtgc tgtctggcgg acgctgggag aaaaccgacc   5580
tgacctacag gatcctgcgg ttcccatggc agctggtgca ggaacaggtg cggcagacaa   5640
tggctgaggc cctgaaagtg tggagcgatg tgaccccact gacctttact gaagtgcacg   5700
agggcagggc tgacatcatg atcgacttcg cccggtactg gcatgggac gacctgcctt    5760
ttgatgggcc tgggggcatc ctggcccatg ccttcttccc caaaactcac cgggaagggg   5820
atgtgcactt cgactatgat gagacctgga ctatcgggga tgaccagggc acagacctgc   5880
tgcaggtggc cgcccatgtg tttggccacg tgctggggct gcagcacaca acagctgcca   5940
aggccctgat gtccgccttc tacacctttc gctacccact gagtctgagc ccagatgact   6000
gcaggggcgt gcagcacctg tatggccagc cctggcccac tgtgacctcc aggacccag    6060
ccctgggccc ccaggctggg attgacacca atgagattgc ccccctggag ccagacgccc   6120
ctccagatgc ctgtgaggcc tcctttgacg ccgtgtccac catcagaggc gagctgtttt   6180
tcttcaaggc cggctttgtg tggagactga gagggggcca gctgcagccc ggctacccag   6240
ctctggcctc tcgccactgg cagggactgc ccagccctgt ggacgctgcc ttcgaggatg   6300
cccagggcca catttggttc ttccagggcg ctcagtactg ggtgtacgac ggcgaaaagc   6360
cagtgctggg ccctgctccc ctgaccgagc tgggcctggt gagattccca gtgcatgccg   6420
ccctggtgtg gggacccgag aagaacaaaa tctacttctt ccggggcagg gactactgga   6480
gattccaccc cagcacccgg agagtggaca gtccgtgcc cagaagggcc actgactgga   6540
gaggagtgcc ctctgagatc gacgccgcct tccaggacgc tgatggctat gcctacttcc   6600
tgcgcggcag gctgtactgg aagtttgacc ctgtgaaagt gaaggctctg gaaggcttcc   6660
ccagactggt gggccctgac ttctttggct gtgccgagcc tgccaacact ttcctgt      6717
```

```
<210> SEQ ID NO 3
<211> LENGTH: 11
<212> TYPE: PRT
<213> ORGANISM: Artificial Sequence
<220> FEATURE:
<223> OTHER INFORMATION: Amino acid sequence of Zn binding domain of
      hMMP-11
<220> FEATURE:
<221> NAME/KEY: VARIANT
<222> LOCATION: 3, 4, 6, 7, 9, 10
<223> OTHER INFORMATION: Xaa = Any Amino Acid

<400> SEQUENCE: 3

His Glu Xaa Xaa His Xaa Xaa Gly Xaa Xaa His
 1               5                  10

<210> SEQ ID NO 4
<211> LENGTH: 1467
<212> TYPE: DNA
<213> ORGANISM: Artificial Sequence
<220> FEATURE:
<223> OTHER INFORMATION: DNA encoding hMMP-11 catalytically inactive

<400> SEQUENCE: 4
atggctccgg ccgcctggct ccgcagcgcg gccgcgcgcg ccctcctgcc cccgatgctg      60
ctgctgctgc tccagccgcc gccgctgctg gcccgggctc tgccgccgga cgccaccac     120 ctccatgccg agaggagggg gccacagccc tggcatgcag ccctgcccag tagcccggca     180 cctgccctg ccacgcagga agcccccgg cctgccagca gctcaggcc tccccgctgt       240 ggcgtgcccg acccatctga tgggctgagt gcccgcaacc gacagaagag gttcgtgctt     300
tctggcgggc gctgggagaa gacggacctc acctacagga tccttcggtt cccatggcag     360
ttggtgcagg agcaggtgcg gcagacgatg gcagaggccc taaaggtatg gagcgatgtg     420
acgccactca cctttactga ggtgcacgag ggcgtgctg acatcatgat cgacttcgcc     480
aggtactggc atgggacga cctgccgttt gatgggcctg ggggcatcct ggcccatgcc     540
ttcttcccca agactcaccg agaagggat gtccacttcg actatgatga cctggact       600 atcggggatg accagggcac agacctgctg caggtggcag cccatgtgtt tggccacgtg     660
ctggggctgc agcacacaac agcagccaag gccctgatgt ccgccttcta cacctttcgc    720
tacccactga gtctcagccc agatgactgc agggcgttc aacacctata tggccagccc     780
tggcccactg tcacctccag gaccccagcc ctgggccccc aggctgggat agacaccaat     840
gagattgcac cgctggagcc agacgccccg ccagatgcct gtgaggcctc ctttgacgcg    900
gtctccacca tccgaggcga gctcttttc ttcaaagcgg gctttgtgtg gcgcctccgt     960 ggggccagc tgcagcccgg ctaccagca ttggcctctc gccactggca gggactgccc   1020
agccctgtgg acgctgcctt cgaggatgcc caggccaca tttggttctt ccaaggtgct    1080
cagtactggg tgtacgacgg tgaaaagcca gtcctgggcc ccgcacccct caccgagctg   1140
ggcctggtga ggttcccggt ccatgctgcc ttggtctggg gtcccgagaa gaacaagatc   1200
tacttcttcc gaggcaggga ctactggcgt ttccacccca gcaccggcg tgtagacagt   1260 cccgtgcccc gcagggccac tgactggaga ggggtgccct ctgagatcga cgctgccttc   1320
caggatgctg atggctatgc ctacttcctg cgcggccgcc tctactggaa gtttgaccct   1380
gtgaaggtga aggctctgga aggcttcccc cgtctcgtgg gtcctgactt ctttggctgt   1440
gccgagcctg ccaacacttt cctctga                                       1467
```

<210> SEQ ID NO 5
<211> LENGTH: 488
<212> TYPE: PRT
<213> ORGANISM: Artificial Sequence
<220> FEATURE:
<223> OTHER INFORMATION: hMMP-11 cat inactive

<400> SEQUENCE: 5

```
Met Ala Pro Ala Ala Trp Leu Arg Ser Ala Ala Arg Ala Leu Leu
 1               5                  10                  15

Pro Pro Met Leu Leu Leu Leu Gln Pro Pro Leu Leu Ala Arg
            20                  25                  30

Ala Leu Pro Pro Asp Val His His Leu His Ala Glu Arg Arg Gly Pro
        35                  40                  45

Gln Pro Trp His Ala Ala Leu Pro Ser Ser Pro Ala Pro Ala
50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg Phe Val Leu Ser Gly Gly Arg Trp Glu Lys Thr Asp Leu Thr Tyr
                100                 105                 110

Arg Ile Leu Arg Phe Pro Trp Gln Leu Val Gln Glu Val Arg Gln
            115                 120                 125

Thr Met Ala Glu Ala Leu Lys Val Trp Ser Asp Val Thr Pro Leu Thr
130                 135                 140

Phe Thr Glu Val His Glu Gly Arg Ala Asp Ile Met Ile Asp Phe Ala
145                 150                 155                 160

Arg Tyr Trp His Gly Asp Asp Leu Pro Phe Asp Gly Pro Gly Gly Ile
                165                 170                 175

Leu Ala His Ala Phe Phe Pro Lys Thr His Arg Glu Gly Asp Val His
                180                 185                 190

Phe Asp Tyr Asp Glu Thr Trp Thr Ile Gly Asp Asp Gln Gly Thr Asp
            195                 200                 205

Leu Leu Gln Val Ala Ala His Val Phe Gly His Val Leu Gly Leu Gln
210                 215                 220

His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
                245                 250                 255

Tyr Gly Gln Pro Trp Pro Thr Val Thr Ser Arg Thr Pro Ala Leu Gly
            260                 265                 270

Pro Gln Ala Gly Ile Asp Thr Asn Glu Ile Ala Pro Leu Glu Pro Asp
        275                 280                 285

Ala Pro Pro Asp Ala Cys Glu Ala Ser Phe Asp Ala Val Ser Thr Ile
290                 295                 300

Arg Gly Glu Leu Phe Phe Phe Lys Ala Gly Phe Val Trp Arg Leu Arg
305                 310                 315                 320

Gly Gly Gln Leu Gln Pro Gly Tyr Pro Ala Leu Ala Ser Arg His Trp
                325                 330                 335

Gln Gly Leu Pro Ser Pro Val Asp Ala Ala Phe Glu Asp Ala Gln Gly
            340                 345                 350

His Ile Trp Phe Phe Gln Gly Ala Gln Tyr Trp Val Tyr Asp Gly Glu
        355                 360                 365

Lys Pro Val Leu Gly Pro Ala Pro Leu Thr Glu Leu Gly Leu Val Arg
370                 375                 380
```

```
Phe Pro Val His Ala Ala Leu Val Trp Gly Pro Glu Lys Asn Lys Ile
385                 390                 395                 400

Tyr Phe Phe Arg Gly Arg Asp Tyr Trp Arg Phe His Pro Ser Thr Arg
            405                 410                 415

Arg Val Asp Ser Pro Val Pro Arg Ala Thr Asp Trp Arg Gly Val
                420                 425                 430

Pro Ser Glu Ile Asp Ala Ala Phe Gln Asp Ala Asp Gly Tyr Ala Tyr
            435                 440                 445

Phe Leu Arg Gly Arg Leu Tyr Trp Lys Phe Asp Pro Val Lys Val Lys
        450                 455                 460

Ala Leu Glu Gly Phe Pro Arg Leu Val Gly Pro Asp Phe Phe Gly Cys
465                 470                 475                 480

Ala Glu Pro Ala Asn Thr Phe Leu
                485
```

<210> SEQ ID NO 6
<211> LENGTH: 1470
<212> TYPE: DNA
<213> ORGANISM: Artificial Sequence
<220> FEATURE:
<223> OTHER INFORMATION: codon optimized DNA encoding catalytically
      inactive hMMP-11

<400> SEQUENCE: 6

```
atggctcctg ccgcctggct gagaagcgct gccgctagag ccctgctgcc ccctatgctg      60
ctgctcctgc tgcagcctcc tcctctgctg gctcgggctc tgcctcctga cgtgcaccac     120
ctgcatgccg agaggagggg gccacagccc tggcatgctg ccctgcccag tagccctgct     180
cctgcccctg ccacacagga agccccagaa cctgccagca gcctgaggcc tcccagatgt     240
ggcgtgcccg acccatctga tgggctgagt gcccgcaacc ggcagaagag attcgtgctg     300
tctggcggac gctgggagaa aaccgacctg acctacagga cctgcgcgtt ccatggcag      360
ctggtgcagg aacaggtgcg gcagacaatg gctgaggccc tgaaagtgtg gagcgatgtg     420
accccactga cctttactga gtgcacgag gcaggctg acatcatgat cgacttcgcc       480
cggtactggc atggggacga cctgcctttt gatgggcctg ggggcatcct ggcccatgcc     540
ttcttcccca aaactcaccg ggaagggat gtgcacttcg actatgatga cctggact        600
atcggggatg accagggcac agacctgctg caggtggccg cccatgtgtt tggccacgtg     660
ctggggctgc agcacacaac agctgccaag gccctgatgt ccgccttcta caccttcgc     720
tacccactga gtctgagccc agatgactgc aggggcgtgc agcacctgta tggccagccc     780
tggcccactg tgacctccag gaccccagcc tgggccccc aggctgggat tgacaccaat     840
gagattgccc ccctggagcc agacgcccct ccagatgcct gtgaggcctc ctttgacgcc     900
gtgtccacca tcagaggcga gctgttttc ttcaaggccg gctttgtgtg gagactgaga     960
ggggccagc tgcagcccgg ctaccagct ctggcctctc gccactggca gggactgccc      1020
agccctgtgg acgctgcctt cgaggatgcc cagggccaca tttggttctt ccagggcgct     1080
cagtactggg tgtacgacgg cgaaaagcca gtgctgggcc tgctccct gaccgagctg      1140
ggcctggtga gattcccagt gcatgccgcc ctggtgtggg acccgagaa gaacaaatc      1200
tacttcttcc ggggcaggga ctactggaga ttccacccca gcaccggag agtggacagt     1260
cccgtgccca aaggccac tgactggaga ggagtgcct ctgagatcga cgccgcttc        1320
caggacgctg atggctatgc ctacttcctg cgcggcaggc tgtactggaa gtttgaccct     1380
gtgaaagtga aggctctgga aggcttcccc agactggtgg gccctgactt ctttggctgt     1440
```

```
gccgagcctg ccaacacttt cctgtgataa                                    1470
```

<210> SEQ ID NO 7
<211> LENGTH: 309
<212> TYPE: DNA
<213> ORGANISM: Artificial Sequence
<220> FEATURE:
<223> OTHER INFORMATION: DNA encoding LTB without the signal peptide

<400> SEQUENCE: 7

```
gctcccccagt ctattacaga actatgttcg gaatatcgca acacacaaat atatacgata    60
aatgacaaga tactatcata tacggaatcg atggcaggta aaagagaaat ggttatcatt   120
acatttaaga gcggcgcaac atttcaggtc gaagtcccgg gcagtcaaca tatagactcc   180
caaaaaaaag ccattgaaag gatgaaggac acattaagaa tcacatatct gaccgagacc   240
aaaattgata attatgtgt atggaataat aaaacccca attcaattgc ggcaatcagt     300
atggaaaac                                                           309
```

<210> SEQ ID NO 8
<211> LENGTH: 309
<212> TYPE: DNA
<213> ORGANISM: Artificial Sequence
<220> FEATURE:
<223> OTHER INFORMATION: Codon optimized DNA encoding LTB without signal
      peptide

<400> SEQUENCE: 8

```
gccccccaga gcatcaccga gctgtgcagc gagtaccgga cacccagat ttacaccatc      60
aacgacaaga tcctgagcta caccgagagc atggccggca gagggagat ggtgatcatc    120
accttcaaga gcggcgccac cttccaggtg gaggtgcccg gcagccagca catcgacagc   180
cagaagaagg ccatcgagcg gatgaaggac accctgcgga tcacctacct caccgagacc   240
aagatcgaca agctgtgcgt gtggaacaac aagaccccca cagcatcgc cgccatcagc    300
atggagaat                                                          309
```

<210> SEQ ID NO 9
<211> LENGTH: 103
<212> TYPE: PRT
<213> ORGANISM: Artificial Sequence
<220> FEATURE:
<223> OTHER INFORMATION: LTB without the signal sequence

<400> SEQUENCE: 9

```
Ala Pro Gln Ser Ile Thr Glu Leu Cys Ser Glu Tyr Arg Asn Thr Gln
  1               5                  10                  15
Ile Tyr Thr Ile Asn Asp Lys Ile Leu Ser Tyr Thr Glu Ser Met Ala
             20                  25                  30
Gly Lys Arg Glu Met Val Ile Ile Thr Phe Lys Ser Gly Ala Thr Phe
         35                  40                  45
Gln Val Glu Val Pro Gly Ser Gln His Ile Asp Ser Gln Lys Lys Ala
     50                  55                  60
Ile Glu Arg Met Lys Asp Thr Leu Arg Ile Thr Tyr Leu Thr Glu Thr
 65                  70                  75                  80
Lys Ile Asp Lys Leu Cys Val Trp Asn Asn Lys Thr Pro Asn Ser Ile
                 85                  90                  95
Ala Ala Ile Ser Met Glu Asn
            100
```

<210> SEQ ID NO 10
<211> LENGTH: 593
<212> TYPE: PRT
<213> ORGANISM: Artificial Sequence
<220> FEATURE:
<223> OTHER INFORMATION: catalytically inactive hMMP-11-LTB fusion polypeptide

<400> SEQUENCE: 10

```
Met Ala Pro Ala Ala Trp Leu Arg Ser Ala Ala Arg Ala Leu Leu
 1               5                  10                  15

Pro Pro Met Leu Leu Leu Leu Gln Pro Pro Leu Leu Ala Arg
            20                  25                  30

Ala Leu Pro Pro Asp Val His His Leu His Ala Glu Arg Gly Pro
            35                  40                  45

Gln Pro Trp His Ala Ala

```
    370                 375                 380

Phe Pro Val His Ala Ala Leu Val Trp Gly Pro Glu Lys Asn Lys Ile
385                 390                 395                 400

Tyr Phe Phe Arg Gly Arg Asp Tyr Trp Arg Phe His Pro Ser Thr Arg
                405                 410                 415

Arg Val Asp Ser Pro Val Pro Arg Arg Ala Thr Asp Trp Arg Gly Val
            420                 425                 430

Pro Ser Glu Ile Asp Ala Ala Phe Gln Asp Ala Asp Gly Tyr Ala Tyr
        435                 440                 445

Phe Leu Arg Gly Arg Leu Tyr Trp Lys Phe Asp Pro Val Lys Val Lys
    450                 455                 460

Ala Leu Glu Gly Phe Pro Arg Leu Val Gly Pro Asp Phe Phe Gly Cys
465                 470                 475                 480

Ala Glu Pro Ala Asn Thr Phe Leu Ser Arg Ala Pro Gln Ser Ile Thr
                485                 490                 495

Glu Leu Cys Ser Glu Tyr Arg Asn Thr Gln Ile Tyr Thr Ile Asn Asp
            500                 505                 510

Lys Ile Leu Ser Tyr Thr Glu Ser Met Ala Gly Lys Arg Glu Met Val
        515                 520                 525

Ile Ile Thr Phe Lys Ser Gly Ala Thr Phe Gln Val Glu Val Pro Gly
    530                 535                 540

Ser Gln His Ile Asp Ser Gln Lys Lys Ala Ile Glu Arg Met Lys Asp
545                 550                 555                 560

Thr Leu Arg Ile Thr Tyr Leu Thr Glu Thr Lys Ile Asp Lys Leu Cys
                565                 570                 575

Val Trp Asn Asn Lys Thr Pro Asn Ser Ile Ala Ala Ile Ser Met Glu
            580                 585                 590

Asn

<210> SEQ ID NO 11
<211> LENGTH: 1779
<212> TYPE: DNA
<213> ORGANISM: Artificial Sequence
<220> FEATURE:
<223> OTHER INFORMATION: catalytically inactive hMMP-11-LTB fusion
      polypeptide

<400> SEQUENCE: 11
atggctccgg ccgcctggct ccgcagcgcg gccgcgcgcg ccctcctgcc cccgatgctg      60
ctgctgctgc tccagccgcc gccgctgctg gcccgggctc tgccgccgga cgcccaccac     120
ctccatgccg agaggagggg gccacagccc tggcatgcag ccctgcccag tagcccggca     180
cctgcccctg ccacgcagga agccccccgg cctgccagca gcctcaggcc tccccgctgt     240
ggcgtgcccg acccatctga tgggctgagt gcccgcaacc gacagaagag gttcgtgctt     300
tctggcgggc gctgggagaa gacggacctc acctacagga tccttcggtt cccatggcag     360
ttggtgcagg agcaggtgcg gcagacgatg gcagaggccc taaaggtatg gagcgatgtg     420
acgccactca cctttactga ggtgcacgag ggccgtgctg acatcatgat cgacttcgcc     480
aggtactggc atggggacga cctgccgttt gatgggcctg gggggcatcct ggcccatgcc     540 ttcttcccca agactcaccg agaaggggat gtccacttcg actatgatga gacctggact     600
atcggggatg accagggcac agacctgctg caggtggcag cccatgtgtt tggccacgtg     660
ctggggctgc agcacacaac agcagccaag gccctgatgt ccgccttcta cacctttcgc     720
tacccactga gtctcagccc agatgactgc aggggcgttc aacacctata tggccagccc     780
```

-continued

```
tggcccactg tcacctccag gaccccagcc ctgggccccc aggctgggat agacaccaat    840
gagattgcac cgctggagcc agacgccccg ccagatgcct gtgaggcctc ctttgacgcg    900
gtctccacca tccgaggcga gctctttttc ttcaaagcgg gctttgtgtg gcgcctccgt    960
gggggccagc tgcagcccgg ctacccagca ttggcctctc gccactggca gggactgccc   1020
agccctgtgg acgctgcctt cgaggatgcc cagggccaca tttggttctt ccaaggtgct   1080
cagtactggg tgtacgacgg tgaaaagcca gtcctgggcc ccgcacccct caccgagctg   1140
ggcctggtga ggttcccggt ccatgctgcc ttggtctggg gtcccgagaa gaacaagatc   1200
tacttcttcc gaggcaggga ctactggcgt ttccacccca gcacccggcg tgtagacagt   1260
cccgtgcccc gcagggccac tgactggaga ggggtgccct ctgagatcga cgctgccttc   1320
caggatgctg atggctatgc ctacttcctg cgcggccgcc tctactggaa gtttgaccct   1380
gtgaaggtga aggctctgga aggcttcccc cgtctcgtgg gtcctgactt ctttggctgt   1440
gccgagcctg ccaacacttt cctctctaga gccccccaga gcatcaccga gctgtgcagc   1500
gagtaccgga acacccagat ttacaccatc aacgacaaga tcctgagcta caccgagagc   1560
atggccggca agagggagat ggtgatcatc accttcaaga gcggcgccac cttccaggtg   1620
gaggtgcccg gcagccagca catcgacagc cagaagaagg ccatcgagcg gatgaaggac   1680
accctgcgga tcacctacct caccgagacc aagatcgaca agctgtgcgt gtggaacaac   1740
aagaccccca acagcatcgc cgccatcagc atggagaat                           1779
```

<210> SEQ ID NO 12
<211> LENGTH: 1785
<212> TYPE: DNA
<213> ORGANISM: Artificial Sequence
<220> FEATURE:
<223> OTHER INFORMATION: Codon-optimized DNA encoding catalytically inactive hMMP-11-LTB fusion polypeptide

<400> SEQUENCE: 12

```
atggctcctg ccgcctggct gagaagcgct gccgctagag ccctgctgcc ccctatgctg     60
ctgctcctgc tgcagcctcc tcctctgctg gctcgggctc tgcctcctga cgtgcaccac    120
ctgcatgccg agaggagggg gccacagccc tggcatgctg ccctgcccag tagccctgct    180
cctgcccctg ccacacagga agcccccaga cctgccagca gcctgaggcc tcccagatgt    240
ggcgtgcccg acccatctga tgggctgagt gcccgcaacc ggcagaagag attcgtgctg    300
tctggcggac gctgggagaa aaccgacctg acctacagga tcctgcggtt cccatggcag    360
ctggtgcagg aacaggtgcg gcagacaatg gctgaggccc tgaaagtgtg gagcgatgtg    420
accccactga cctttactga agtgcacgag ggcagggctg acatcatgat cgacttcgcc    480
cggtactggc atggggacga cctgcctttt gatgggcctg gggcatcct ggcccatgcc     540
ttcttcccca aaactcaccg ggaaggggat gtgcacttcg actatgatga gacctggact    600
atcggggatg accagggcac agacctgctg caggtggccg cccatgtgtt tggccacgtg    660
ctggggctgc agcacacaac agctgccaag gccctgatgt ccgccttcta cacctttcgc    720
tacccactga gtctgagccc agatgactgc aggggcgtgc agcacctgta tggccagccc    780
tggcccactg tgacctccag gaccccagcc ctgggccccc aggctgggat tgacaccaat    840
gagattgccc ccctggagcc agacgcccct ccagatgcct gtgaggcctc ctttgacgcc    900
gtgtccacca tcagaggcga gctgtttttc ttcaaggccg gctttgtgtg gagactgaga    960
gggggccagc tgcagcccgg ctacccagct ctggcctctc gccactggca gggactgccc   1020
agccctgtgg acgctgcctt cgaggatgcc cagggccaca tttggttctt ccagggcgct   1080
```

```
cagtactggg tgtacgacgg cgaaaagcca gtgctgggcc ctgctcccct gaccgagctg    1140
ggcctggtga gattcccagt gcatgccgcc ctggtgtggg acccgagaa gaacaaaatc     1200 tacttcttcc ggggcaggga ctactggaga ttccacccca gcaccggag agtggacagt     1260 cccgtgccca gaagggccac tgactggaga ggagtgccct ctgagatcga cgccgccttc    1320
caggacgctg atggctatgc ctacttcctg cgcggcaggc tgtactggaa gtttgaccct    1380
gtgaaagtga aggctctgga aggcttcccc agactggtgg gccctgactt ctttggctgt    1440
gccgagcctg ccaacacttt cctgtctaga gccccccaga gcatcaccga gctgtgcagc    1500
gagtaccgga cacccagat ttacaccatc aacgacaaga tcctgagcta caccgagagc    1560
atggccggca gagggagat ggtgatcatc accttcaaga gcggcgccac cttccaggtg    1620
gaggtgcccg gcagccagca catcgacagc cagaagaagg ccatcgagcg gatgaaggac    1680
accctgcgga tcacctacct caccgagacc aagatcgaca gctgtgcgt gtggaacaac    1740 aagacccca cagcatcgc cgccatcagc atggagaatt gataa                     1785

<210> SEQ ID NO 13
<211> LENGTH: 1621
<212> TYPE: DNA
<213> ORGANISM: Artificial Sequence
<220> FEATURE:
<223> OTHER INFORMATION: Codon-optimized DNA encoding catalytically
      inactive mMMP-11 and flanking regions

<400> SEQUENCE: 13
ctgcagagat ctggtaccga tatcgccacc atggccagag ccgcctgcct gctgagagcc      60
atcagcagag tgctgctgct gcctctgcca ctgctgctcc tgttgctgct cctgctgcct    120
agccctctga tggccagagc taggcctcct gagagccaca gacaccaccc tgtgaagaag    180
ggccctagac tgctgcacgc cgccctgcct aacaccctga ccagcgtgcc tgccagccac    240
tgggtgccaa gccctgccgg cagcagcaga cctctgagat gtggcgtgcc tgacctgcct    300
gacgtgctga cgccaggaa caggcagaag cggttcgtgc tgagcggcgg cagatgggaa    360
aagaccgacc tgacctacag gatcctgaga ttccctggc agctggtgcg tgagcaagtg    420
cgtcagaccg tggccgaggc cctccaggtg tggagcgagg tgacccctct gaccttcacc    480
gaggtgcacg agggcagagc cgacatcatg atcgacttcg ccagatactg gcacggcgac    540
aacctgcctt tcgacggccc tggcggcatc ctggcccacg cctttttccc caagacccac    600
agagagggcg acgtgcactt cgactacgac gagacctgga ccatcggcga taaccagggc    660
accgacctgc tccaggtggc cgcccacgct ttcggccacg tgctgggcct ccagcacacc    720
accgccgcca aggccctgat gagccccttc tacaccttca gataccccct gagcctgagc    780
cctgacgaca aagaggcat ccagcacctg tacggcagac ctcagatggc cctaccagc     840 cctgccccta ccctgagcag ccaggccggc accgacacca cgagatcgc cctgctggag    900 cctgagaccc ctcctgatgt gtgcgagacc agcttcgacg ccgtgtctac catcagaggc    960
gagctgttct tcttcaaggc cggctttgtg tggagactga ggagcggcag actccagcct   1020 ggctacccctg cctggccag cagacactgg cagggcctgc cttccctgt ggacgccgcc    1080 ttcgaggacg cccaggggcca gatttggttc ttccagggcg cccagtactg ggtgtacgac    1140
ggcgagaagc ctgtgctggg ccctgcccca ctgagcaagc tgggactcca gggcagcctc    1200
gtgcacgctg ccctggtgtg gggacctgaa aagaacaaaa tctatttctt cagaggcggc    1260
gactactgga gattccaccc caggacccag agagtggaca accccgtgcc cagaagaagc    1320
```

-continued

```
accgactgga gaggcgtgcc tagcgagatc gacgccgctt tccaggatgc tgagggctac   1380
gcctacttcc tgaggggcca cctgtactgg aagttcgacc ccgtgaaggt gaaggtgctg   1440
gagggcttcc ctagacctgt gggccctgac ttcttcgact gcgccgagcc tgccaacacc   1500
ttccggtcta gatgataagt gactaaatga gaattcgtcg acgcggccgc cggcggtagt   1560
cgtacctctt aactattaga tctactattc actgatttac tcttaagcag ctgcgccggc   1620
g                                                                   1621
```

<210> SEQ ID NO 14
<211> LENGTH: 1972
<212> TYPE: DNA
<213> ORGANISM: Artificial Sequence
<220> FEATURE:
<223> OTHER INFORMATION: Codon-optimized DNA encoding catalytically inactive mMMP-11-LTB fusion polypeptide and flanking regions

<400> SEQUENCE: 14

```
ctgcagagat ctggtaccga tatcgccacc ctgcagagat ctggtaccga tatcgccacc     60
atggccagag ccgcctgcct gctgagagcc atcagcagag tgctgctgct gcctctgcca    120
ctgctgctcc tgttgctgct cctgctgcct agccctctga tggccagagc taggcctcct    180
gagagccaca gacaccaccc tgtgaagaag ggccctagac tgctgcacgc cgccctgcct    240
aacaccctga ccagcgtgcc tgccagccac tgggtgccaa gccctgccgg cagcagcaga    300
cctctgagat gtggcgtgcc tgacctgcct gacgtgctga acgccaggaa caggcagaag    360
cggttcgtgc tgagcggcgg cagatgggaa aagaccgacc tgacctacag gatcctgaga    420
ttcccctggc agctggtgcg tgagcaagtg cgtcagaccg tggccgaggc cctccaggtg    480
tggagcgagg tgacccctct gaccttcacc gaggtgcacg agggcagagc cgacatcatg    540
atcgacttcg ccagatactg gcacggcgac aacctgcctt tcgacggccc tggcggcatc    600
ctggcccacg cctttttccc caagacccac agagagggcg acgtgcactt cgactacgac    660
gagacctgga ccatcggcga taaccagggc accgacctgc tccaggtggc cgcccacgct    720
ttcggccacg tgctgggcct ccagcacacc accgccgcca aggccctgat gagccccttc    780
tacaccttca gataccccct gagcctgagc cctgacgaca gaagaggcat ccagcacctg    840
tacggcagac ctcagatggc ccctaccagc cctgccccta ccctgagcag ccaggccggc    900
accgacacca acgagatcgc cctgctggag cctgagaccc ctcctgatgt gtgcgagacc    960
agcttcgacg ccgtgtctac catcagaggc gagctgttct tcttcaaggc cggctttgtg   1020
tggagactga ggagcggcag actccagcct ggctaccctg ccctggccag cagacactgg   1080
cagggcctgc cttcccctgt ggacgccgcc ttcgaggacg cccagggcca gatttggttc   1140
ttccagggcg cccagtactg ggtgtacgac ggcgagaagc ctgtgctggg ccctgcccca   1200
ctgagcaagc tgggactcca gggcagccct gtgcacgctg ccctggtgtg gggacctgaa   1260
aagaacaaaa tctatttctt cagaggcggc gactactgga gattccaccc caggacccag   1320
agagtggaca accccgtgcc cagaagaagc accgactgga gaggcgtgcc tagcgagatc   1380
gacgccgctt tccaggatgc tgagggctac gcctacttcc tgaggggcca cctgtactgg   1440
aagttcgacc ccgtgaaggt gaaggtgctg gagggcttcc ctagacctgt gggccctgac   1500
ttcttcgact gcgccgagcc tgccaacacc ttccggtcta gagcccccca gagcatcacc   1560
gagctgtgca gcgagtaccg gaacacccag atttacacca tcaacgacaa gatcctgagc   1620
tacaccgaga gcatggccgg caagagggag atggtgatca tcaccttcaa gagcggcgcc   1680
```

```
accttccagg tggaggtgcc cggcagccag cacatcgaca gccagaagaa ggccatcgag   1740
cggatgaagg acaccctgcg gatcacctac ctcaccgaga ccaagatcga caagctgtgc   1800
gtgtggaaca acaagacccc caacagcatc gccgccatca gcatggagaa ttgataatct   1860
agatgataag tgactaaatg agaattcgtc gacgcggccg ccggcggtag tcgtacctct   1920
taactattag atctactatt cactgattta ctcttaagca gctgcgccgg cg           1972

<210> SEQ ID NO 15
<211> LENGTH: 597
<212> TYPE: PRT
<213> ORGANISM: Artificial Sequence
<220> FEATURE:
<223> OTHER INFORMATION: catalytically inactive mMMP-11-LTB fusion
      polypeptide <400> SEQUENCE: 15

Met Ala Arg Ala Ala Cys Leu Leu Arg Ala Ile Ser Arg Val Leu Leu
 1               5                  10                  15

Leu Pro Leu Pro Leu Leu Leu Leu Leu Leu Leu Leu Leu Pro Ser Pro
            20                  25                  30

Leu Met Ala Arg Ala Arg Pro Pro Glu Ser His Arg His His Pro Val
        35                  40                  45

Lys Lys Gly Pro Arg Leu Leu His Ala Ala Leu Pro Asn Thr Leu Thr
    50                  55                  60

Ser Val Pro Ala Ser His Trp Val Pro Ser Pro Ala Gly Ser Ser Arg
65                  70                  75                  80

Pro Leu Arg Cys Gly Val Pro Asp Leu Pro Asp Val Leu Asn Ala Arg
                85                  90                  95

Asn Arg Gln Lys Arg Phe Val Leu Ser Gly Gly Arg Trp Glu Lys Thr
            100                 105                 110

Asp Leu Thr Tyr Arg Ile Leu Arg Phe Pro Trp Gln Leu Val Arg Glu
        115                 120                 125

Gln Val Arg Gln Thr Val Ala Glu Ala Leu Gln Val Trp Ser Glu Val
    130                 135                 140

Thr Pro Leu Thr Phe Thr Glu Val His Glu Gly Arg Ala Asp Ile Met
145                 150                 155                 160

Ile Asp Phe Ala Arg Tyr Trp His Gly Asp Asn Leu Pro Phe Asp Gly
                165                 170                 175

Pro Gly Gly Ile Leu Ala His Ala Phe Phe Pro Lys Thr His Arg Glu
            180                 185                 190

Gly Asp Val His Phe Asp Tyr Asp Glu Thr Trp Thr Ile Gly Asp Asn
        195                 200                 205

Gln Gly Thr Asp Leu Leu Gln Val Ala Ala His Ala Phe Gly His Val
    210                 215                 220

Leu Gly Leu Gln His Thr Thr Ala Ala Lys Ala Leu Met Ser Pro Phe
225                 230                 235                 240

Tyr Thr Phe Arg Tyr Pro Leu Ser Leu Ser Pro Asp Asp Arg Arg Gly
                245                 250                 255

Ile Gln His Leu Tyr Gly Arg Pro Gln Met Ala Pro Thr Ser Pro Ala
            260                 265                 270

Pro Thr Leu Ser Ser Gln Ala Gly Thr Asp Thr Asn Glu Ile Ala Leu
        275                 280                 285

Leu Glu Pro Glu Thr Pro Pro Asp Val Cys Glu Thr Ser Phe Asp Ala
    290                 295                 300

Val Ser Thr Ile Arg Gly Glu Leu Phe Phe Phe Lys Ala Gly Phe Val
305                 310                 315                 320
```

Trp Arg Leu Arg Ser Gly Arg Leu Gln Pro Gly Tyr Pro Ala Leu Ala
                325                 330                 335

Ser Arg His Trp Gln Gly Leu Pro Ser Pro Val Asp Ala Ala Phe Glu
                340                 345                 350

Asp Ala Gln Gly Gln Ile Trp Phe Phe Gln Gly Ala Gln Tyr Trp Val
                355                 360                 365

Tyr Asp Gly Glu Lys Pro Val Leu Gly Pro Ala Pro Leu Ser Lys Leu
            370                 375                 380

Gly Leu Gln Gly Ser Pro Val His Ala Ala Leu Val Trp Gly Pro Glu
385                 390                 395                 400

Lys Asn Lys Ile Tyr Phe Phe Arg Gly Gly Asp Tyr Trp Arg Phe His
                405                 410                 415

Pro Arg Thr Gln Arg Val Asp Asn Pro Val Pro Arg Arg Ser Thr Asp
                420                 425                 430

Trp Arg Gly Val Pro Ser Glu Ile Asp Ala Ala Phe Gln Asp Ala Glu
                435                 440                 445

Gly Tyr Ala Tyr Phe Leu Arg Gly His Leu Tyr Trp Lys Phe Asp Pro
            450                 455                 460

Val Lys Val Lys Val Leu Glu Gly Phe Pro Arg Pro Val Gly Pro Asp
465                 470                 475                 480

Phe Phe Asp Cys Ala Glu Pro Ala Asn Thr Phe Arg Ser Arg Ala Pro
                485                 490                 495

Gln Ser Ile Thr Glu Leu Cys Ser Cys Tyr Arg Asn Thr Gln Ile Tyr
                500                 505                 510

Thr Ile Asn Asp Lys Ile Leu Ser Tyr Thr Glu Ser Met Ala Gly Lys
            515                 520                 525

Arg Glu Met Val Ile Ile Thr Phe Lys Ser Gly Ala Thr Phe Gln Val
                530                 535                 540

Glu Val Pro Gly Ser Gln His Ile Asp Ser Gln Lys Lys Ala Ile Glu
545                 550                 555                 560

Arg Met Lys Asp Thr Leu Arg Ile Thr Tyr Leu Thr Glu Thr Lys Ile
                565                 570                 575

Asp Lys Leu Cys Val Trp Asn Asn Lys Thr Pro Asn Ser Ile Ala Ala
                580                 585                 590

Ile Ser Met Glu Asn
        595

<210> SEQ ID NO 16
<211> LENGTH: 29
<212> TYPE: DNA
<213> ORGANISM: Artificial Sequence
<220> FEATURE:
<223> OTHER INFORMATION: PCR Primer

<400> SEQUENCE: 16
cccggggcgg atggcacggg ccgcctgtc                                     29

<210> SEQ ID NO 17
<211> LENGTH: 32
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (6)...(6)
<223> OTHER INFORMATION: m = a or c
<220> FEATURE:
<221> NAME/KEY: misc_feature

```
<222> LOCATION: (14)...(14)
<223> OTHER INFORMATION: r = a or g

<400> SEQUENCE: 17
gtcagmggaa agtrttggca ggctcagcac ag                                32
```

MATRIX METALLOPROTEINASE 11 VACCINE

CROSS REFERENCE TO RELATED APPLICATIONS

This application is a §371 National Stage Application of PCT/EP2006/009536, international filing date of Oct. 3, 2006, which claims the benefit of U.S. Provisional Application No. 60/724,498, filed Oct. 7, 2005, now expired, the contents of which are incorporated herein by reference in their entirety.

BACKGROUND OF THE INVENTION (1) Field of the Invention

The present invention relates to compositions comprising matrix metalloproteinase 11 (MMP-11) or stromelysin-3 (ST-3) or the nucleic acid encoding the MMP-11 for use in vaccines for treating tumors and cancers, which overexpress MMP-11. In particular embodiments, the compositions comprise a nucleic acid encoding a fusion polypeptide that includes a catalytically inactivated MMP-11 linked at the C-terminus to an immunoenhancing element wherein the codons encoding the MMP-11 and the immunoenhancing element have been optimized for enhanced expression of the fusion polypeptide in human cells. In other embodiments, the compositions comprise the catalytically inactivated MMP-11 linked at the C-terminus to an immunoenhancing element. The compositions can be used alone or in synergy with vaccines against other tumor associated antigens as well as with conventional therapies such as radiation therapy and chemotherapy.

(2) Description of Related Art

Matrix Metalloproteinase-11 (MMP-11) or stromelysin 3 (ST3) is expressed in many, if not most, invasive primary carcinomas and in a number of their metastases and more rarely in sarcomas and other non-epithelial malignancies (See Basset et al., Critical Reviews in Oncology/Hematology 26: 43-53, (1997)). Measuring levels of MMP-11 expression can be used to identify patients at greatest risk for cancer recurrence. It has been shown that recurrent breast carcinomas occurred more frequently in patients who had high levels of MMP-11 RNA or protein in their tumors than in patients who had low levels of MMP-11 RNA or protein in their tumors. Similarly, MMP-11 expression was found to be increased in pancreatic tumors as compared to normal tissue and the level of MMP-11 expression was strongly associated with lymph node involvement and overall survival (Jones et al., Clin. Cancer Res. 10: 2832-2845, (2004)). MMP-11 mRNA expression is also significantly increased in colon carcinomas compared to MMP-11 mRNA expression in non-tumorous tissue (Thewes et al., Diagn. Mol. Pathol. 5: 284-290, (1996)).

The role of MMP-11 in cancer progression has been demonstrated by several pre-clinical observations. For example, MMP-11 expression was shown to promote tumor take in mice (Noel et al., J Clin Invest 97: 1924-1930 (1996)). MMP-11 was also shown to promote homing of malignant epithelial cells in a paracrine manner and the homing appears to require extracellular matrix associated factors (Masson et al., J. Cell Biol. 140: 1535-1541 (1998)) such as basic fibroblast growth factor (bFGF) (Mari et al., J. Biol. Chem. 273: 618-626 (1998)). MMP-11 protease activity can modulate cancer progression by remodeling extracellular matrix and inducing it to release microenvironmental factors (Noel et al., Oncogene 19: 1605-1612 (2000)). MMP-11 has been shown to have an anti-apoptotic and anti-necrotic effect on tumorous cells (Boulay et al., Cancer Res. 61: 2189-2193 (2001)), which appears to be mediated by its catalytic activity (Wu et al., J. Cell Biochem. 82:549-555 (2001)). MMP-11 deficiency has been shown to increase tumor free survival and modulate local or distant invasion (Andarawewa et al., Cancer Res. 63:5844-5849 (2003)). Knocking down MMP-11 mRNA in gastric cancer cells appears to dramatically suppresses tumor growth both in vitro and in vivo (Deng et al., Biochem. Biophys. Res. Comm. 26: 274-281 (2005)). MMP-11 has also been shown to interfere with the immune system's response against tumors in that a cleavage product of a1-proteinase inhibitor, generated by MMP-11 cleavage, decreases the sensitivity of tumor cells to natural killer cells (NK) (Kataoka et al., Am. J. Pathol. 154: 457-468, (1999)). In addition, an increased number of neutrophils and macrophages infiltrate tumors in MMP-11-null mice compared with wild-type mice, indicating that MMP-11 inhibits a chemoattractant for these cells (Boulay et al., Cancer Res. 61: 2189-2193 (2001)). Thus, MMP-11 appears to play a crucial role in the initial stage of tumorigenesis.

Several agents have been developed that block the synthesis of MMPs, prevent them from interacting with the molecules that direct their activities to the cell surface, or inhibit their enzymatic activity (reviewed in Egeblad and Werb, Nature Reviews 2: 163-174 (2002)). Most of agents were not specifically directed against MMP-11 but interfered with functions of other members of MMP family. However, clinical trials with several of these MMP inhibitors have suggested the inhibitors have a limited antitumor effect. Therefore, in light of the above, there is a need for anti-cancer therapies and treatments that inhibit or interfere with MMP-11 activity.

BRIEF SUMMARY OF THE INVENTION

The present invention provides compositions comprising matrix metalloproteinase 11 (MMP-11) or stromelysin-3 (ST-3) or the nucleic acid encoding the MMP-11 for use in vaccines for treating tumors and cancers, which overexpress MMP-11. In particular embodiments, the compositions comprise a nucleic acid encoding a fusion polypeptide that includes a catalytically inactivated MMP-11 linked at the C-terminus to an immunoenhancing element wherein the codons encoding the MMP-11 and the immunoenhancing element have been optimized for enhanced expression of the fusion polypeptide in human cells. In other embodiments, the compositions comprise the catalytically inactivated MMP-11 linked at the C-terminus to an immunoenhancing element. The compositions can be used alone or in synergy with vaccines against other tumor associated antigens as well as with conventional therapies such as radiation therapy and chemotherapy.

Therefore, the present invention provides a nucleic acid comprising a nucleotide sequence encoding an MMP-11 polypeptide wherein one or more of the nucleotide codons encoding the MMP-11 that occur at low frequency in nucleic acids encoding highly expressed proteins in humans have been replaced with nucleotide codons that occur at a higher frequency in the nucleic acids encoding the highly expressed proteins in humans (that is, the nucleotide sequence has been optimized for high expression of the nucleic acid in cells of human origin).

In a preferred embodiment of the nucleic acid, the MMP-11 encoded by the nucleotide sequence further includes a mutation that renders the MMP-11 catalytically inactive, in particular embodiments, the mutation is in the zinc binding domain of the MMP-11.

In further embodiments of the nucleic acid, the polynucleotide encodes an MMP-11, wherein the polynucleotide encodes a human MMP-11 or an MMP-11 of primate origin.

In further still embodiments of the nucleic acid, the nucleic acid includes a nucleotide sequence that has the nucleotide sequence of SEQ ID NO:4.

The present invention further provides a nucleic acid encoding a fusion polypeptide having an MMP-11 linked to an immunoenhancing element or substantial portion thereof. In preferred embodiments, one or more of the nucleotide codons encoding the fusion polypeptide that occur at low frequency in nucleic acids encoding highly expressed proteins in humans have been replaced with nucleotide codons that occur at a higher frequency in the nucleic acids encoding the highly expressed proteins in humans. In particular embodiments, the immunoenhancing element is selected from the group consisting of heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and subunit B of the heat-labile toxin (LTB).

In a currently preferred embodiment of the nucleic acid, the immunoenhancing element is the *E. coli* LTB. In further embodiments, the LTB does not include a signal sequence. In further still embodiments of the nucleic acid, the LTB is encoded by the nucleotide sequence shown in SEQ ID NO:8.

In preferred embodiments of the above nucleic acid, the MMP-11 includes a mutation that renders the MMP-11 catalytically inactive.

In further embodiments of the nucleic acid, the MMP-11 is encoded by the nucleotide sequence shown in SEQ ID NO:4. In further still embodiments, the fusion polypeptide includes the nucleotide sequence shown in SEQ ID NO:11.

The present invention further provides an expression vector comprising the nucleic acid of any one of the aforementioned embodiments operably linked to a promoter. The present invention further provides a host cell containing any one of the embodiments of the above expression vector therein. The present invention further provides a process, comprising culturing the above host cell in a cell culture medium under conditions for producing the fusion polypeptide.

The present invention further provides a fusion polypeptide comprising an MMP-11 linked to an immunoenhancing element or substantial portion thereof.

In particular embodiments of the fusion polypeptide, the immunoenhancing element is selected from the group consisting of heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and subunit B of the heat-labile toxin (LTB).

In a currently preferred embodiment of the fusion polypeptide, the immunoenhancing element polypeptide is the *E. coli* LTB. In further still embodiments, the LTB does not include a signal sequence. In further still embodiments, the LTB includes the amino acid sequence shown in SEQ ID NO:9.

In preferred embodiments of the fusion polypeptide, the MMP-11 includes a mutation that renders it catalytically inactive. Preferably, the mutation is in the zinc binding domain of the MMP-11. In further still embodiments, the MMP-11 polypeptide comprising the fusion polypeptide includes the amino acid sequence shown in SEQ ID NO:5 or the polypeptide includes the amino acid sequence shown in SEQ ID NO:10.

The present invention further provides a polynucleotide vaccine comprising a nucleotide sequence encoding an MMP-11 wherein one or more of the nucleotide codons encoding the MMP-11 that occur at low frequency in nucleic acids encoding highly expressed proteins in humans have been replaced with nucleotide codons that occur at a higher frequency in the nucleic acids encoding the highly expressed proteins in humans.

In a preferred embodiment of the polynucleotide vaccine, the MMP-11 encoded by the nucleotide sequence further includes a mutation that renders the MMP-11 catalytically inactive. In a currently preferred embodiment, the mutation is in the zinc binding domain of the MMP-11. In further still embodiments of the polynucleotide vaccine, the MMP-11 is an MMP-11 of human origin or of primate origin. In a further still embodiment of the polynucleotide vaccine, the nucleotide sequence includes the nucleotide sequence of SEQ ID NO:4.

The present invention further provides a polynucleotide vaccine encoding a fusion polypeptide having an MMP-11 linked to an immunoenhancing element or substantial portion thereof. In particular embodiments of the polynucleotide vaccine, the immunoenhancing element is selected from the group consisting of heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and subunit B of the heat-labile toxin (LTB).

In a preferred embodiment of the polynucleotide vaccine, the MMP-11 encoded by the nucleotide sequence further includes a mutation that renders the MMP-11 catalytically inactive. In a currently preferred embodiment, the mutation is in the zinc binding domain of the MMP-11. In further still embodiments of the polynucleotide vaccine, the MMP-11 is an MMP-11 of human origin or of primate origin. In a further still embodiment of the polynucleotide vaccine, the nucleotide sequence includes the nucleotide sequence of SEQ ID NO:4.

In a currently preferred embodiment of the polynucleotide vaccine, the immunoenhancing element polypeptide is the subunit B of heat labile toxin (LTB) of *E. coli*. In further still embodiments, the LTB does not include a signal sequence and in further still embodiments, the LTB is encoded by the nucleotide sequence shown in SEQ ID NO:8.

In a further preferred embodiment of the polynucleotide vaccine, one or more of the nucleotide codons encoding the fusion polypeptide that occur at low frequency in nucleic acids encoding highly expressed proteins in humans have been replaced with nucleotide codons that occur at a higher frequency in the nucleic acids encoding the highly expressed proteins in humans.

In a further embodiment, the MMP-11 is encoded by the nucleotide sequence shown in SEQ ID NO:4. In a further still embodiment, the fusion polypeptide includes the nucleotide sequence shown in SEQ ID NO:11.

In further still embodiments of the polynucleotide vaccine, the vaccine further includes one or more genetic adjuvants. Such genetic adjuvants include, but are not limited to, costimulatory molecules such as CD80 and CD86; proinflammatory cytokines such as interleukin-1α (IL-1α); tumor necrosis factor-α and β (TNF-α and TNF-β); Th1 cytokines such as IL-2, IL-12, IL-15, and IL-18; Th2 cytokines such as IL-4, IL-5, and IL-10; macrophage colony-stimulating factor (M-CSF); granulocyte colony-stimulating factor (G-CSF); granulocytes-monocyte colony-stimulating factor (GM-CSF); IL-8; interferon-γ-inducible protein-10 (γIP-10); macrophage inhibitory protein-1α (MIP-1α); and RANTES.

In further still embodiments of the polynucleotide vaccine, the vaccine further includes one or more conventional adjuvants. Conventional adjuvants include, but are not limited to, mineral salts such as aluminum phosphate or hydroxide, bacteria-derived adjuvants such as monophosphoryl lipid A, cholera toxin, muramyl peptides, lipid particles such as cationic liposomes and mannan-coated liposomes, emulsifier adjuvants such as QS-21, and synthetic adjuvants such as ubenimex.

The present invention further provides a polypeptide vaccine comprising a fusion polypeptide having an MMP-11 linked to an immunoenhancing element polypeptide or substantial portion thereof. In a preferred embodiment, the MMP-11 has a mutation that renders it catalytically inactive. In a currently preferred embodiment, the mutation is in the zinc binding domain of the MMP-11.

In particular embodiments of the polypeptide vaccine, the immunoenhancing element is selected from the group consisting of heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and subunit B of the heat-labile toxin (LTB).

In a currently preferred embodiment, the immunoenhancing element is the *E. coli* LTB. In further still embodiments, the LTB does not include a signal sequence. In further still embodiments, the LTB includes the amino acid sequence shown in SEQ ID NO:9.

In further still embodiments of the polypeptide vaccine, the MMP-11 includes the amino acid sequence shown in SEQ ID NO:5 or includes the amino acid sequence shown in SEQ ID NO:10.

In further still embodiments of the polypeptide vaccine, the vaccine includes one or more molecular adjuvants capable of modulating the immune response towards either a Th1 or Th2 response. Such molecular adjuvants include, but are not limited to, costimulatory molecules such as CD80 and CD86; proinflammatory cytokines such as interleukin-1α (IL-1α); tumor necrosis factor-α and β (TNF-α and TNF-β); Th1 cytokines such as IL-2, IL-12, IL-15, and IL-18; Th2 cytokines such as IL-4, IL-5, and IL-10; macrophage colony-stimulating factor (M-CSF); granulocyte colony-stimulating factor (G-CSF); granulocytes-monocyte colony-stimulating factor (GM-CSF); IL-8; interferon-γ-inducible protein-10 (γIP-10); macrophage inhibitory protein-1α (MIP-1α); and RANTES.

In further still embodiments of the polypeptide vaccine, the vaccine can include one or more conventional adjuvants. Conventional adjuvants include, but are not limited to, mineral salts such as aluminum phosphate or hydroxide, bacteria-derived adjuvants such as monophosphoryl lipid A, cholera toxin, muramyl peptides, lipid particles such as cationic liposomes and mannan-coated liposomes, emulsifier adjuvants such as QS-21, and synthetic adjuvants such as ubenimex.

The present invention further provides for the use of a nucleic acid a nucleotide sequence encoding an MMP-11 wherein one or more of the nucleotide codons encoding the fusion polypeptide that occur at low frequency in nucleic acids encoding highly expressed proteins in humans have been replaced with nucleotide codons that occur at a higher frequency in the nucleic acids encoding the highly expressed proteins in humans; use of a nucleic acid encoding a fusion polypeptide comprising an MMP-11 linked to an immunoenhancing element in a medicament for treating a carcinoma in an individual; and, use of a fusion polypeptide comprising an MMP-11 linked to an immunoenhancing element in a medicament for treating a carcinoma in an individual.

The present invention further provides a method for treating a carcinoma in an individual comprising providing a polynucleotide vaccine which includes a nucleic acid including a nucleotide sequence encoding an MMP-11 wherein one or more of the nucleotide codons encoding the MMP-11 that occur at low frequency in nucleic acids encoding highly expressed proteins in humans have been replaced with nucleotide codons that occur at a higher frequency in the nucleic acids encoding the highly expressed proteins in humans or a fusion polypeptide that includes an MMP-11 linked to an immunoenhancing element; and administering the vaccine to the individual to treat the cancer. In currently preferred embodiments of the nucleic acid encoding the fusion polypeptide, one or more of the nucleotide codons encoding the fusion polypeptide that are not present in nucleic acids encoding highly expressed proteins in humans have been replaced with nucleotide codons that are present in nucleic acids encoding the highly expressed proteins in humans.

In particular embodiments of the above method, the individual is undergoing one or more treatments selected from the group consisting of chemotherapy, radiation therapy, and vaccine against a tumor associated antigen. In further still embodiments, the individual has an invasive carcinoma selected from the group consisting of the breast, colon, head and neck, lung, ovary, pancreas, prostate, skin (basal cell carcinoma), uterus (cervix carcinoma and endometrial carcinoma) or the individual has a non-invasive carcinoma that has a risk of evolving towards invasion.

In a preferred embodiment of the method, the MMP-11 encoded by the nucleotide sequence further includes a mutation that renders the MMP-11 catalytically inactive. In a currently preferred embodiment, the mutation is in the zinc binding domain of the MMP-11. In further still embodiments of the polynucleotide vaccine, the MMP-11 is an MMP-11 of human origin or of primate origin. In a further still embodiment of the polynucleotide vaccine, the nucleotide sequence includes the nucleotide sequence of SEQ ID NO:4.

In particular embodiments of the method, the immunoenhancing element is selected from the group consisting of heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and subunit B of the heat-labile toxin (LTB).

In a currently preferred embodiment of the method, the immunoenhancing element polypeptide is the subunit B of heat labile toxin of *E. coli* (LTB). In further still embodiments, the LTB does not include a signal sequence and in further still embodiments, the LTB is encoded by the nucleotide sequence shown in SEQ ID NO:8.

In a further embodiment, the MMP-11 is encoded by the nucleotide sequence shown in SEQ ID NO:4. In a further still embodiment, the fusion polypeptide includes the nucleotide sequence shown in SEQ ID NO:11.

In further still embodiments of the method, the vaccine further includes one or more genetic adjuvants. Such genetic adjuvants include, but are not limited to, costimulatory molecules such as CD80 and CD86; proinflammatory cytokines such as interleukin-1α (IL-1α); tumor necrosis factor-α and β

(TNF-α and TNF-β); Th1 cytokines such as IL-2, IL-12, IL-15, and IL-18; Th2 cytokines such as IL-4, IL-5, and IL-10; macrophage colony-stimulating factor (M-CSF); granulocyte colony-stimulating factor (G-CSF); granulocytes-monocyte colony-stimulating factor (GM-CSF); IL-8; interferon-γ-inducible protein-10 (γIP-10); macrophage inhibitory protein-1α (MIP-1α); and RANTES.

In further still embodiments of the method, the vaccine further includes one or more conventional adjuvants. Conventional adjuvants include, but are not limited to, mineral salts such as aluminum phosphate or hydroxide, bacteria-derived adjuvants such as monophosphoryl lipid A, cholera toxin, muramyl peptides, lipid particles such as cationic liposomes and mannan-coated liposomes, emulsifier adjuvants such as QS-21, and synthetic adjuvants such as ubenimex.

The present invention further provides a method for treating a carcinoma in an individual comprising providing a vaccine that includes a fusion polypeptide having an MMP-11 linked to an immunoenhancing element; and administering the vaccine to the individual to treat the cancer.

In particular embodiments of the above method, the individual is undergoing one or more treatments selected from the group consisting of chemotherapy, radiation therapy, and vaccine against a tumor associated antigen. In further still embodiments, the individual has an invasive carcinoma selected from the group consisting of the breast, colon, head and neck, lung, ovary, pancreas, prostate, skin (basal cell carcinoma), uterus (cervix carcinoma and endometrial carcinoma) or the individual has a non-invasive carcinoma that has a risk of evolving towards invasion.

In particular embodiments of the method, the immunoenhancing element is selected from the group consisting of heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and subunit B of the heat-labile toxin (LTB).

In a currently preferred the method, the immunoenhancing element is the *E. coli* LTB. In further still embodiments, the LTB does not include a signal sequence. In further still embodiments, the LTB includes the amino acid sequence shown in SEQ ID NO:9.

In further still embodiments of the method, the MMP-11 includes the amino acid sequence shown in SEQ ID NO:5 or includes the amino acid sequence shown in SEQ ID NO:10.

In further still embodiments of the method, the vaccine includes one or more molecular adjuvants capable of modulating the immune response towards either a Th1 or Th2 response. Such molecular adjuvants include, but are not limited to, costimulatory molecules such as CD80 and CD86; proinflammatory cytokines such as interleukin-1α (IL-1α); tumor necrosis factor-α and β (TNF-α and TNF-β); Th1 cytokines such as IL-2, IL-12, IL-15, and IL-18; Th2 cytokines such as IL-4, IL-5, and IL-10; macrophage colony-stimulating factor (M-CSF); granulocyte colony-stimulating factor (G-CSF); granulocytes-monocyte colony-stimulating factor (GM-CSF); IL-8; interferon-γ-inducible protein-10 (γIP-10); macrophage inhibitory protein-1α (MIP-1α); and RANTES.

In further still embodiments of the method, the vaccine can include one or more conventional adjuvants. Conventional adjuvants include, but are not limited to, mineral salts such as aluminum phosphate or hydroxide, bacteria-derived adjuvants such as monophosphoryl lipid A, cholera toxin, muramyl peptides, lipid particles such as cationic liposomes and mannan-coated liposomes, emulsifier adjuvants such as QS-21, and synthetic adjuvants such as ubenimex.

The present invention further provides a method for identifying an analyte for inhibiting a cancer that overexpresses MMP-11, which comprises inducing the cancer in a mouse; administering the analyte to the mouse with the induced cancer; and determining whether the analyte inhibits the cancer in the mouse with the induced tumor, which identifies the analyte for inhibiting a cancer that overexpresses the MMP-11.

In particular embodiments, the analyte is determined to bind the MMP-11 before it is administered to the mouse.

In further still embodiments, the cancer that is induced in the mouse is a colon cancer, and in further still embodiments, the cancer is induced in the mouse by administering to the mouse 1-2dimethylhydrazine (DMH) in an amount sufficient to induce the cancer in the mouse.

DEFINITIONS

As used throughout the specification and in the appended claims, the singular forms "a," "an," and "the" include the plural reference unless the context clearly dictates otherwise.

As used throughout the specification and appended claims, the following definitions and abbreviations apply:

The term "promoter" refers to a recognition site on a DNA strand to which RNA polymerase binds. The promoter forms an initiation complex with RNA polymerase to initiate and drive transcriptional activity of a nucleic acid sequence located downstream from the promoter. The promoter can be modified by including activating sequences termed "enhancers" or inhibiting sequences termed "silencers" within the promoter. The term further includes both promoters which are inducible and promoters which are constitutive.

The term "cassette" refers to a nucleotide or gene sequence that is to be expressed from a vector, for example, the nucleotide or gene sequence encoding the cDkk4 protein. In general, a cassette comprises a gene sequence inserted into a vector which in some embodiments provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences which can be provided by the vector include, but are not limited to, enhancers, transcription termination sequences, splice acceptor and donor sequences, introns, ribosome binding sequences, and poly(A) addition sequences.

The term "vector" refers to some means by which DNA fragments can be introduced into a host organism or host tissue. There are various types of vectors including plasmid, viruses (including adenovirus), bacteriophages, and cosmids.

The term "MMP-1" refers to the MMP-11 protein or polypeptide.

The term "immunoenhancing element" refers to a polypeptide portion of the MMP-11 fusion polypeptides of the present invention that is capable of stimulating or enhancing the immune response to the associated MMP-11, relative to full-length wild-type MMP-11. Immunoenhancing elements of the present invention include, but are not limited to, polypeptides comprising all of or a substantial portion of the polypeptides selected from the group consisting of heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and heat labile toxin B subunit (LTB) of *E. coli* or other bacterial species.

The term "fusion protein" or "fusion polypeptide" refers to a protein having at least two polypeptides covalently linked in which one polypeptide comes from one protein sequence or domain and the other polypeptide comes from a second protein sequence or domain. The fusion proteins of the present invention comprise an MMP-11, and a second polypeptide, which comprises an immunoenhancing element or substantial portion thereof, which, in some cases, is a bacterial toxin. The MMP-11 may be a human MMP-11 or MMP-11 from another species. The polypeptides that comprise the fusion protein are preferably linked N-terminus to C-terminus. The MMP-11 and the immunoenhancing element can be fused in any order. In some embodiments of this invention, the C-terminus of the MMP-11 is fused to the amino terminus of the immunoenhancing element or the immunoenhancing element is fused to the amino terminus of the MMP-11.

The term "MMP-1 fusion protein" is intended to be a general term which refers to a fusion protein as described above, which comprises an MMP-11 polypeptide or fragment or variant thereof fused to a polypeptide comprising an immunoenhancing element or portion thereof. The term "MMP-11 fusion protein" is interchangeable with the term "MMP-11 fusion polypeptide".

The term "recombinant MMP-11" refers to an MMP-11 that has been modified by genetic engineering. For example, the term includes the catalytically inactive MMP-11 and the MMP-11 fusion polypeptides disclosed herein.

The terms "polynucleotide", "nucleic acid", and "nucleic acid molecule" are intended to refer to any polymer of nucleotides bonded to one another by phosphodiester bonds, for example, ribonucleic acid (RNA) or deoxyribonucleic acid (DNA) molecules of any length. Polynucleotides or nucleic acid can include genes and fragments or portions thereof, probes, oligonucleotides, and primers. DNA can be either complementary DNA (cDNA) or genomic DNA, e.g. a gene encoding an MMP-11 or variant thereof. The terms "nucleic acid" and "polynucleotide" are used interchangeably herein.

The term "recombinant polynucleotide" or "recombinant nucleic acid" refers to a polynucleotide which has been modified by genetic engineering. For example, the term includes a polynucleotide encoding an MMP-11 in which the polynucleotide includes a mutation which renders the MMP-11 catalytically inactive. The term further includes the polynucleotide encoding the MMP-11 or catalytically inactive MMP-11 wherein one or more of the nucleotide codons have been optimized for enhanced expression in humans. The term also includes the MMP-11 fusion polypeptides disclosed herein.

The term "variant thereof" refers to recombinant MMP-11 or polynucleotide. For example, the catalytically inactive MMP-11 or MMP-11 fusion polypeptide is a variant of the wild-type MMP-11. A polynucleotide encoding MMP-11 in which the codons have been optimized for enhanced expression in humans, the catalytically inactive MMP-11, or the MMP-11 fusion polypeptide is a variant of the wide-type polynucleotide encoding the wild-type MMP-11.

The term "substantially similar" means that a given nucleic acid or amino acid sequence shares at least 75%, preferably 85%, more preferably 90%, and even more preferably 95% identity with a reference sequence. In the present invention, the reference sequence can be relevant portions of the wild-type MMP-11 nucleotide or amino acid sequence, or the wild-type nucleotide or amino acid sequence of an immunoenhancing element, as dictated by the context of the text. The reference sequence may be, for example, the wild-type human or non-human MMP-11 sequence. Thus, an MMP-11 sequence that is "substantially similar" to the wild-type MMP-11 or fragment thereof will share at least 75% identity with the relevant fragment of the wild-type MMP-11, along the length of the fragment, preferably 85% identity, more preferably 90% identity and even more preferably 95% identity. Whether a given MMP-11 or immunoenhancing element polypeptide or nucleotide sequence is "substantially similar" to a reference sequence can be determined for example, by comparing sequence information using sequence analysis software such as the GAP computer program, version 6.0, available from the University of Wisconsin Genetics Computer Group (UWGCG). The GAP program utilizes the alignment method of Needleman and Wunsch (J. Mol. Biol. 48:443, 1970), as revised by Smith and Waterman (Ada. Appl. Math. 2:482, 1981).

The term "gene" refers both to the genomic nucleic acid encoding the gene product, which for many genes comprises a combination of exon and intron sequences, and the cDNA derived from the mRNA encoding the gene product, which does not include intron sequences.

The term "substantial portion" of a gene or polypeptide, variant, fragment, or subunit thereof, means a portion of at least 50%, preferably 75%, more preferably 90%, and even more preferably 95% of a reference sequence.

The phrases "codon-optimized", "nucleotide codons are optimized for enhanced expression in humans", "nucleotide sequence has been optimized for high expression", and the like for describing the polynucleotides of the present invention mean that one or more of the nucleotide codons of the MMP-11 and/or immunoenhancing element that occur at low frequency in nucleic acids encoding highly expressed proteins in an organism have been replaced with nucleotide codons that occur at a higher frequency in the nucleic acids encoding the highly expressed proteins in the organism. The nucleotide codon for a particular amino acid with "low frequency" is that nucleotide codon with the lowest frequency of use in nucleic acids that encode highly expressed proteins in the organism. The nucleotide codon for a particular amino acid with "high frequency" is that nucleotide codon with the highest frequency of use or a frequency of use that is higher than the nucleotide codon with the lowest frequency in nucleic acids that encode highly expressed proteins in the organism.

The term "treatment" refers to both therapeutic treatment and prophylactic or preventative measures. Individuals in need of treatment include those already with the disorder as well as those prone to have the disorder or those in which the disorder is to be prevented.

The polynucleotides and polypeptides of the present invention are intended for use as treatments for disorders or conditions associated with overexpression of MMP-11 and which are characterized by aberrant cell proliferation, including, but not limited to, breast cancer, colorectal cancer, and lung cancer.

The term "effective amount" means sufficient vaccine composition is introduced to produce the adequate levels of the polypeptide, so that an immune response results. One skilled in the I art recognizes that this level may vary.

The term "analyte" includes molecule, compound, composition, drug, protein, peptide, nucleic acid, antibody and active fragment thereof, nucleic acid aptamer, peptide aptamer, and the like.

BRIEF DESCRIPTION OF THE DRAWINGS

FIG. 3 shows the nucleotide sequence of codon-optimized nucleic acid encoding catalytically inactive mouse MMP-11 (mMMP-11opt) (SEQ ID NO:13). The nucleotides corresponding to the codon-optimized, catalytically inactive mMMP-11 are in black and the additional nucleotides for the polylinker comprising an XbaI site are underlined. Nucleotides for cloning sites, Kozak sequence, and stop codons are in shown in italics. The mMMP-11 start codon is in bold type.

FIG. 4 shows the nucleotide sequence of codon-optimized nucleic acid encoding catalytically inactive mMMP-11 linked to *E. coli* LTB (mMMP-11-LTBopt) (SEQ ID NO:14). The nucleotides corresponding to the codon-optimized, catalytically inactive mMMP-11 are in black and the additional nucleotides for the polylinker comprising an XbaI site are underlined. The nucleotides encoding the *E. coli* LTB sequence are in lower-case letters. Nucleotides for cloning sites, Kozak sequence, and stop codons are in italics.

FIG. 5 shows the amino acid sequence of the catalytically inactive mMMP-11-LTBopt fusion polypeptide (SEQ ID NO:15). The amino acids comprising the polypeptide corresponding to the catalytically inactive mMMP-11 are in black and the LTB sequence are in italics. The amino acids encoded by the polylinker are underlined.

FIG. 14 shows the nucleotide sequence of a nucleic acid encoding catalytically inactive human MMP-11 (hMMP-11 (cat-)opt) wherein the codons have been optimized for expression in humans (SEQ ID NO:4).

FIG. 15 shows the amino acid sequence of catalytically inactive hMMP-11 (SEQ ID NO:5).

FIG. 16 shows the nucleotide sequence of a nucleic acid encoding a fusion polypeptide comprising a catalytically-inactive hMMP-11 linked to the *E. coli* LTB wherein the codons encoding both the MMP-11 and the LTB have been optimized for expression in humans (SEQ ID NO:12) (hMMP-11(cat-)-LTBopt). The codons encoding amino acids 1 to 21 of the LTB are not included in the fusion polypeptide. The nucleotides corresponding to the codon-optimized, catalytically inactive hMMP-11 are in black and the additional nucleotides for the polylinker comprising an XbaI site are underlined. The nucleotides encoding the *E. coli* LTB sequence are in lower-case letters.

FIG. 17 shows the amino acid sequence for the catalytically-inactive hMMP-11-LTB fusion polypeptide (SEQ ID NO:10). The amino acids comprising the catalytically-inactive MMP-11 are in upper-case letters, the amino acids comprising the LTB are in italics, and the amino acids encoded by the polylinker are underlined. The start codon is in bold-faced type.

FIG. 18 shows a map of the vector pV1J-hMMP-11(cat-) opt comprising a codon-optimized polynucleotide encoding the catalytically inactive hMMP-11.

DETAILED DESCRIPTION OF THE INVENTION

Figure 1:
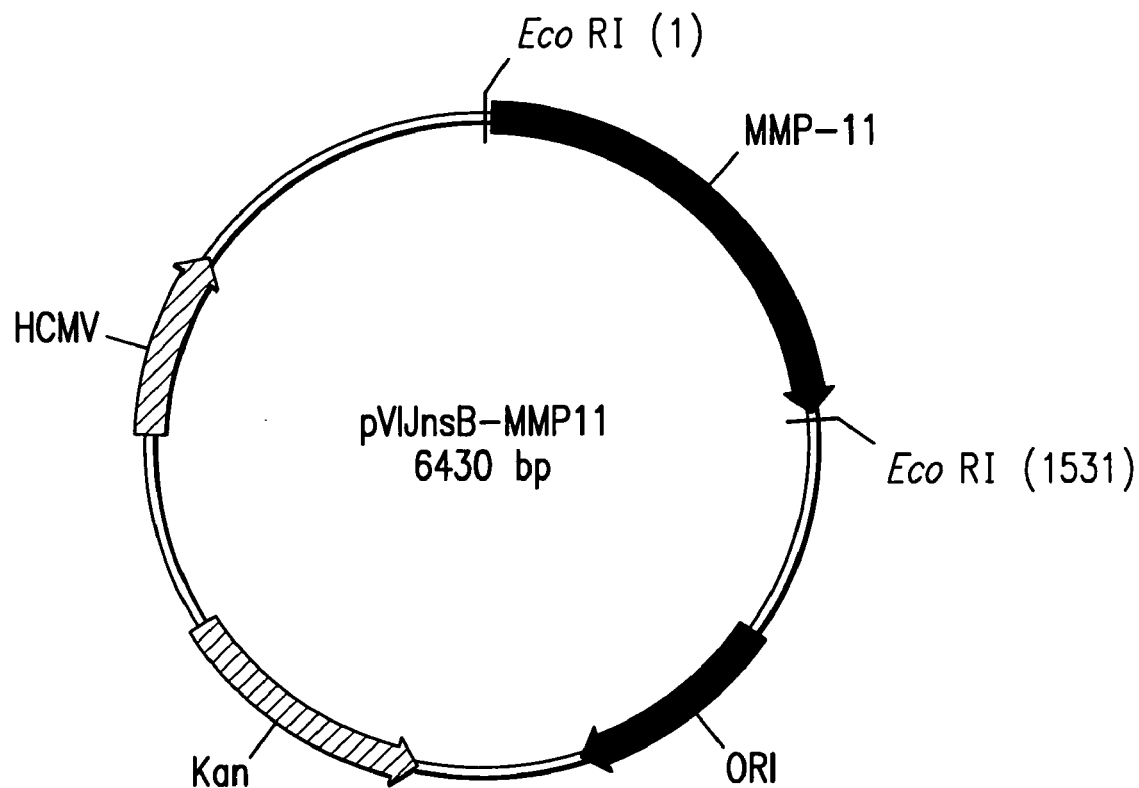
FIG. 1 shows a map of the vector pV1JnsB-mMMP-11. The human CMV promoter and mouse MMP-11 cDNA are indicated.

The present invention provides compositions that can be used as anti-MMP-11 vaccines for inhibiting tumors and cancers that overexpress MMP-11 in an individual, in particular, for inhibiting invasive carcinomas that overexpress MMP-11 such as particular carcinomas of the breast, colon, head and neck, lung, ovary, pancreas, prostate, skin (basal cell carcinoma), uterus (cervix carcinoma and endometrial carcinoma) or non-invasive carcinomas that have a risk of evolving towards invasion. The anti-MMP-11 vaccine or anti-tumor associated antigen (anti-TAA) vaccine can be used, for example, in a mono-therapy regimen that targets tumor cells and stromal compartment; in a multi-therapy regimen with another anti-TAA vaccine, which targets tumor cells via a multi-specific cell mediated immune response and stromal compartment; in a multi-therapy regimen with other molecules or adjuvants; in a therapy that includes chemotherapy, the rationale being to get the stromal structure more permeable to cytotoxic agents; in a therapy that includes radiotherapy; and, in any one of the previous therapies wherein the MMP-11 is provided as part of a multi-epitope polypeptide or minigene. The anti-MMP-11 vaccines of the present invention can be a polypeptide vaccine, or preferably, a polynucleotide vaccine.

As shown in the Examples, it was found that administering an anti-MMP-11 vaccine to mice having colonic tumors, which had been induced with 1,2-dimethylhydrazine (DMH), caused a significant reduction of the DMH-induced carcinogenesis progression in the colon tissue of the mice. In susceptible mouse strains, such as A/J, but also to a lesser extent BALB/c, DMH induced carcinogenesis progression in colon tissue goes through different stages: (1) aberrant crypt formation (ACF); (2) Adenoma; (3) Polyp; and (4) Adenocarcinoma (See Bird, Cancer Lett. 93(1): 55-71 (1995)). The inventors found that MMP-11 is overexpressed in the DMH-induced tumor tissue, which suggested the suitability of DMH-induced carcinogenesis in mice as a model for anti-MMP-11 therapy and vaccination. The inventors then found that a genetic vaccine comprising a nucleic acid encoding the mouse MMP-11 (mMMP-11), wherein the mMMP-11 had been inactivated catalytically by introducing a point mutation in the Zn binding domain in the catalytic site, induced an immune response in mice and that the immune response was further enhanced when the nucleic acid encoding the catalytically inactive mMMP-11 was linked to a nucleic acid encoding the subunit B heat-labile toxin (LTB) of *E. coli* without the signal peptide and the codons encoding the MMP-11 was optimized for enhanced expression in the mouse and the codons encoding the LTB were optimized for enhanced expression in humans. Finally, the inventors found that the genetic vaccine was efficacious in effecting a reduction in all phases of DMH-induced carcinogenesis in the mouse. Therefore, in light of the results of the mouse model, the present invention provides anti-MMP-11 vaccines comprising either a polynucleotide encoding the MMP-11 or the MMP-11 polypeptide, preferably an anti-MMP-11 vaccine having any one of the embodiments as set forth below.

In its most basic embodiment, the present invention provides a nucleic acid or polynucleotide, which comprises a nucleic acid or polynucleotide molecule encoding an MMP-11 or variant due to degeneracy of the genetic code, genetic engineering as disclosed below, or both, under the control of or operably linked to a suitable heterologous promoter and preferably wherein the nucleic acid encoding the MMP-11 has been modified to include a mutation that renders the encoded MMP-11 catalytically inactive. The mutation that renders the MMP-11 catalytically inactive can be introduced into the polynucleotide by genetic engineering. The recombinant polynucleotides encoding the catalytically inactive MMP-11 include polynucleotides derived from humans and non-human species wherein the polynucleotide is modified to include a mutation that renders the encoded MMP-11 catalytically inactive. Non-human species include primates, for example chimpanzee, rhesus monkey, cynomolgus monkey, and the like, and non-primate species, for example mouse, rat, dog, and the like. In a currently preferred embodiment, the recombinant polynucleotide encoding the MMP-11 is of human origin or encodes an MMP-11 having an amino acid sequence the same as or substantially similar to the amino acid sequence of human MMP-11. The nucleotide sequence of the cDNA encoding the human MMP-11 (hMMP-11) is set forth in GenBank Accession No. NM_005940 (SEQ ID NO:1). The recombinant polynucleotide encoding the hMMP-11 is modified as shown below to encode variants which can be used in the anti-MMP-11 vaccines of the present invention. It is to be understood that while the currently preferred embodiments of the present invention comprise recombinant nucleic acids or polynucleotides encoding the hMMP-11, the present invention is not limited to recombinant polynucleotides encoding the hMMP-11. The present invention further include embodiments wherein the recombinant polynucleotides encode MMP-11 of non-human origin and the recombinant nucleic acids or polynucleotides have been modified as shown below to encode MMP-11 variants that can be used in the anti-MMP-11 vaccines of the present invention.

In a preferred embodiment of the recombinant nucleic acid or polynucleotide, the MMP-11 encoded by the polynucleotide is a catalytically inactive variant of the MMP-11. A polynucleotide encoding a catalytically inactive MMP-11 can be produced by modifying by genetic engineering one or more of the nucleotide codons encoding the conserved amino acids comprising the zinc binding site H E X X H X X G X X H (SEQ ID NO:3) of the MMP-11 (for the hMMP-11, amino acids 215 to 225 of SEQ ID NO:5) to an alternative amino acid to produce a recombinant polynucleotide encoding a catalytically inactive MMP-11. For example, as shown by the nucleotide sequence in SEQ ID NO:4 encoding a catalytically inactive hMMP-11, the nucleotide codon GAA encoding the conserved glutamic acid at amino acid position 216 of the hMMP-11 was changed to the nucleotide codon GTG encoding the amino acid valine to produce a catalytically inactive hMMP-11 having the amino acid sequence shown in SEQ ID NO:5 wherein the amino acid at position 216 is valine. Noël et al., (Oncogene 19: 1605-1612 (2000)) have shown that changing the nucleotide codon at position 216 to a nucleotide codon encoding alanine rendered the hMMP-11 catalytically inactive and that changing the nucleotide codon encoding the glutamic acid at amino acid position 220 of the corresponding region of the mMMP-11 with a nucleotide codon that encodes alanine rendered the mMMP-11 catalytically inactive. While the nucleotide codon encoding the glutamic acid at amino acid position number two of SEQ ID NO:3 has been changed to a nucleotide codon encoding valine or alanine to produce a catalytically inactive MMP-11, the nucleotide codon can also be changed to other amino acids or the codons encoding one or more of the other conserved amino acids of the Zn binding domain can be changed to encode other amino acids without departing from the invention.

It has been shown that codon optimization of genes or transcription units coding for particular polypeptides leads to increased expression of the encoded polypeptide, that is increased translation of the mRNA encoding the polypeptide. In the case of a polynucleotide vaccine, the increased expression of the encoded polypeptide produces more of the encoded polypeptide which can lead to increased immunogenecity of the vaccine in vivo, which in turn, can enhance the efficacy of the vaccine. In the context of codon optimization, the term "expression" and its variants refer to translation of the mRNA encoding the polypeptide and not to transcription of the polynucleotide encoding the polypeptide. The term "gene" as used herein refers to both the genomic DNA or RNA encoding a polypeptide and to the cDNA encoding the polypeptide.

Codon optimization is a process that seeks to improve heterologous expression of a gene when that gene is moved into a foreign genetic environment that exhibits a different nucleotide codon usage from the gene's native genetic environment or improve ectopic expression of a gene in its native genetic environment when the gene naturally includes one or more nucleotide codons that are not usually used in genes native to the genetic environment that encode highly expressed genes. In other words, codon optimization involves replacing those nucleotide codons of a gene that are used at a relatively low frequency in a particular genetic environment or organism with nucleotide codons that are used in genes that are expressed at a higher frequency in the genetic environment or organism. In that way, the expression (translation) of the gene product (polypeptide) is increased. The assumption is that the nucleotide codons that appear with high frequency in highly expressed genes are more efficiently translated than nucleotide codons that appear at low frequency.

In general, methods for optimizing nucleotide codons for a particular gene depend on identifying the frequency of the nucleotide codons for each of the amino acids used in genes that are highly expressed in an organism and then replacing those nucleotide codons in a gene of interest that are used with low frequency in the highly expressed genes with nucleotide codons that are identified as being used in the highly expressed genes (See for example Lathe, *Synthetic Oligonucleotide Probes Deduced from Amino Acid Sequence Data: Theoretical and Practical Considerations*, J. Molec. Biol.: 183: 1-12 (1985); Nakamura et al., Nuc. Acid Res. 28: 292 (2000); Fuglsang, Protein Expression & Purification 31: 247-249 (2003). There are numerous computer programs that will automatically analyze the nucleotide codons of a nucleic acid of an organism encoding a gene and suggest nucleotide codons to replace nucleotide codons, which occur with low frequency in the organism, with nucleotide codons that are found in genes that are highly expressed in the organism. For convenience, a table of nucleotide codon usage for humans derived from Nakamura (ibid.) is shown below in Table 1 and identifies which nucleotide codons occur at low frequency in nucleic acids encoding highly expressed proteins in humans and which nucleotide codons occur at a higher frequency in the nucleic acids encoding the highly expressed proteins in humans.

TABLE 1

| Codon | Amino Acid | Frequency | Codon | Amino Acid | Frequency |
|---|---|---|---|---|---|
| UUU | F | 17.4 | UCU | S | 15.1 |
| UUC | F | 20.4 | UCC | S | 17.7 |
| UUA | L | 7.5 | UCA | S | 12.1 |
| UUG | L | 12.8 | UCG | S | 4.5 |
| CUU | L | 13.1 | CCU | P | 17.5 |
| CUC | L | 19.7 | CCC | P | 20.0 |
| CUA | L | 7.1 | CCA | P | 16.9 |
| CUG | L | 39.9 | CCG | P | 7.0 |
| AUU | I | 15.8 | ACU | T | 13.0 |
| AUC | I | 20.9 | ACC | T | 19.0 |
| AUA | I | 7.4 | ACA | T | 15.0 |
| AUG | M | 22.0 | ACG | T | 5.1 |
| GUU | V | 11.0 | GCU | A | 18.5 |
| GUC | V | 14.6 | GCC | A | 28.1 |
| GUA | V | 7.1 | GCA | A | 15.9 |
| GUC | V | 28.4 | GCG | A | 7.5 |
| UAU | Y | 12.1 | UGU | C | 10.4 |
| UAC | Y | 15.3 | UGC | C | 12.6 |
| UAA | * | 1.0 | UGA | * | 1.6 |
| UAG | * | 0.8 | UGG | W | 13.2 |
| CAU | H | 10.8 | CGU | R | 4.6 |
| CAC | H | 15.1 | CGC | R | 10.6 |
| CAA | Q | 12.1 | CGA | R | 6.2 |
| CAG | Q | 34.2 | CGG | R | 11.6 |
| AAU | N | 16.7 | AGU | S | 12.1 |
| AAC | N | 19.1 | AGC | S | 19.4 |
| AAA | K | 24.1 | AGA | R | 11.9 |
| AAG | K | 32.0 | AGG | R | 11.9 |
| GAU | D | 21.7 | GGU | G | 10.8 |
| GAC | D | 25.2 | GGC | G | 22.5 |
| GAA | E | 28.6 | GGA | G | 16.4 |
| GAG | E | 39.7 | GGG | G | 16.5 |

* Stop codon.

Therefore, in further embodiments, a recombinant polynucleotide is provided wherein one or more of the nucleotide codons encoding the amino acids comprising the MMP-11 are optimized to enhance the expression of the encoded MMP-11 and thereby in the case of the anti-MMP-11 vaccine, enhance the efficacy of the anti-MMP-11 vaccine. That is, one or more of the nucleotide codons encoding the MMP-11 and/or immunoenhancing element that occur at low frequency in nucleic acids encoding highly expressed proteins in an organism have been replaced with nucleotide codons that occur at a higher frequency in the nucleic acids encoding the highly expressed proteins in the organism. Preferably, the nucleotide codons are optimized for enhanced expression of the MMP-11 in humans. However, recombinant polynucleotides codon-optimized for enhanced expression in another organism, for example, primates, are equivalents of recombinant polynucleotides codon-optimized for enhanced expression in humans. Currently, it is preferable that the MMP-11 be catalytically inactive and it is currently preferred that the catalytically inactive MMP-11 be the hMMP-11. Where there are multiple nucleotide codons for a particular amino acid of MMP-11 and two or more of the nucleotide codons have the same relative frequency of use in highly expressed human genes or a frequency of use greater in highly expressed human genes than the nucleotide codon having the lowest frequency of use in highly expressed human genes, each of the nucleotide codons for the amino acid in the MMP-11 can independently be any one of the nucleotide codons of the same frequency of use or frequency of use greater than the nucleotide codon having the lowest frequency of use. Not all nucleotide codons in the codon optimized polynucleotide encoding the MMP-11 need be the nucleotide codon having the highest frequency of use in highly expressed human genes. An example of a nucleotide sequence of hMMP-11 that is catalytically inactive and in which the codons encoding the catalytically inactive hMMP-11 have been optimized for expression in humans is shown in SEQ ID NO:6.

The mouse model showed that the efficacy of an anti-MMP-11 vaccine comprising a recombinant polynucleotide encoding a catalytically inactive mMMP-11 in which the nucleotide codons encoding the mMMP-11 were optimized for enhanced expression in the mouse (mMMP-11-opt) was further enhanced when the nucleotide codon encoding the carboxy terminal amino acid of the mMMP-11-opt was linked or fused to nucleotide codons encoding a substantial portion of the immunoenhancing heat-labile toxin B (LTB) of E. coli to produce a fusion polypeptide comprising the mMMP-11 and the E. coli LTB. Therefore, in a preferred embodiment, the recombinant polynucleotide comprises a nucleic acid encoding a the catalytically inactive MMP-11 linked to a nucleic acid encoding an immunoenhancing element polypeptide or substantial portion thereof (MMP-11 fusion polypeptide). In currently preferred embodiments, the recombinant polynucleotide comprises a nucleic acid encoding the catalytically inactive hMMP-11 linked to a nucleic acid encoding an immunoenhancing element which is the LTB of E. coli such that the polynucleotide encodes an hMMP-11-LTB fusion protein. In further embodiments, the nucleic acid encoding the LTB does not include the codons encoding the LTB signal peptide. The nucleic acid sequence encoding the E. coli LTB is available in GenBank Accession No. AB011677 and the amino acid sequence for the E. coli LTB is shown in GenBank Accession No. BAA25726. The signal peptide includes amino acid residues 1 to 21 of the amino acid sequence shown in BAA25726. The nucleotide sequence of the E. coli LTB without the signal peptide is shown in SEQ ID NO:7 and its amino acid sequence is shown in SEQ ID NO:9. The polynucleotide sequence encoding the E. coli LTB without the signal peptide and in which the nucleotide codons encoding the LTB have been optimized for enhanced expression in humans sis shown in SEQ ID NO:8. In a particularly preferred embodiment, the nucleotide codons of the polynucleotide encoding the catalytically inactive hMMP-11 and the LTB are optimized for expression in humans.

While the E. coli LTB was the source for the immunoenhancing element polypeptide that was used in the fusion polypeptide embodiments disclosed herein, the present invention further contemplates embodiments comprising recombinant polynucleotides encoding fusion polypeptides comprising MMP-11 fused to other immunoenhancing element polypeptides or substantial portions thereof. Examples of immunoenhancing element polypeptides include, but are not limited to, heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from Vibrio cholerae, and LTB from other bacterial species.

Therefore, in light of the above, the present invention further provides a recombinant nucleic acid or polynucleotide which encodes a single fusion polypeptide comprising a catalytically inactive MMP-11 linked to an LTB or substantial portion thereof or another immunoenhancing element polypeptide or substantial portion thereof. An example of such a polynucleotide comprises a polynucleotide encoding a polypeptide comprising the amino acid of SEQ ID NO:5 (catalytically inactive hMMP-11) and the amino acid sequence of SEQ ID NO: 8 (E. coli LTB without signal peptide). The polynucleotide can comprise the nucleotide sequence of SEQ ID NO:4 encoding the catalytically inactive hMMP-11 and SEQ ID NO:7 encoding the E. coli LTB without signal peptide or SEQ ID NO:8 (polynucleotide encoding the E. coli LTB without signal peptide codon-optimized for enhanced expression in humans). As an example, the polynucleotide can encode a catalytically inactive hMMP-11-LTB fusion polypeptide having the amino acid sequence shown in SEQ ID NO:10. Such a polypeptide can be encoded by the nucleotide sequence shown in SEQ ID NO:11.

In a preferred embodiment, the nucleotide codons of any one of the recombinant nucleic acids and polynucleotides disclosed herein are optimized for enhanced expression of the recombinant polypeptide encoded thereon in humans. That is, one or more of the nucleotide codons of the recombinant nucleic acids and polynucleotides that occur at low frequency in nucleic acids encoding highly expressed proteins in humans have been replaced with nucleotide codons that occur at a higher frequency in the nucleic acids encoding the highly expressed proteins in humans. It is further preferable in the case of recombinant polynucleotides encoding any one of the fusion polypeptides disclosed herein that the nucleotide codons of the recombinant polynucleotides encoding the immunoenhancing element polypeptide or LTB comprising the recombinant polypeptide are also optimized for enhanced expression of the fusion polypeptide in humans. An example of such a recombinant polynucleotide would comprise the codon-optimized nucleotide sequence of SEQ ID NO:6 encoding the catalytically inactive hMMP-11 and the codon-optimized nucleotide sequence of SEQ ID NO:8 encoding the E. coli LTB without signal peptide. As an example, the recombinant polynucleotide encoding the codon-optimized, catalytically inactive HMMP-11-LTB fusion polypeptide has the nucleotide sequence shown in SEQ ID NO:12.

The present invention further provides recombinant polypeptides comprising a catalytically inactive MMP-11 wherein the one or more of the conserved amino acids comprising the zinc binding site H E X X H X X G X X H (SEQ ID NO:3) of MMP-11 are changed to an alternative amino acid. For example, as shown in SEQ ID NO:5 for hMMP-11 wherein the conserved glutamic acid at position 216 of the hMMP-11 was changed to the amino acid valine to produce a catalytically inactive MMP-11. Preferably, the catalytically inactive MMP-11 polypeptide comprises a fusion polypeptide wherein the MMP-11 is linked at its carboxy terminus to an immunoenhancing element polypeptide or substantial portion of (MMP-11 fusion polypeptide). In currently preferred embodiments, the immunoenhancing element polypeptide is the E. coli LTB. In further embodiments, the LTB does not include its signal peptide. An example of an MMP-1 fusion polypeptide comprises the catalytically inactive hMMP-11 having the amino acid sequence shown in SEQ ID NO:5 linked at its carboxy terminus to the amino terminus of the E. coli LTB polypeptide without signal peptide having the amino acid sequence shown in SEQ ID NO:7. The MMP-11 fusion polypeptide can be encoded by, for example, the polynucleotide shown in SEQ ID NO:11 or the codon-optimized polynucleotide shown in SEQ ID NO:12.

While the E. coli LTB is the source for the immunoenhancing element that was used in the MMP-11 fusion polypeptide embodiments exemplified herein, the present invention further contemplates embodiments comprising MMP-11 fusion polypeptides comprising MMP-11 fused to other immunoenhancing element polypeptides or substantial portions thereof. Examples of immunoenhancing element polypeptides include, but are not limited to, heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from Vibrio cholerae, and LTB from other bacterial species.

The present invention further provides vectors which comprise at least one of the nucleic acid molecules disclosed throughout this specification (herein after "recombinant polynucleotides"), preferably wherein the nucleic acid molecule is operably linked to a heterologous promoter. These vectors can comprise DNA or RNA. For most purposes, DNA plasmid or viral expression vectors are preferred. Typical expression vectors include plasmids, modified viruses, bacteriophage, cosmids, yeast artificial chromosomes, and other forms of episomal or integrated DNA, any of which expresses any one of the recombinant polynucleotides disclosed herein. Preferably, the nucleotide codons encoding the any one of the aforementioned embodiments is optimized for enhanced expression in humans.

An expression vector comprising a polynucleotide encoding any one of the recombinant polynucleotides disclosed herein wherein the DNA is preferably codon-optimized for enhanced expression in humans and operably linked to a heterologous promoter can be used for expression of the any one of the recombinant polynucleotides disclosed herein in a recombinant host cell. Such recombinant host cells can be cultured under suitable conditions to produce any one of the recombinant polynucleotides disclosed herein. Expression vectors include, but are not limited to, cloning vectors, modified cloning vectors, specifically designed plasmids, or specifically designed viruses. The expression vectors described in the examples are acceptable expression vectors.

The nucleic acids of the present invention are preferably assembled into an expression cassette that comprises sequences which provide for efficient expression of any one of the recombinant polynucleotides disclosed herein encoded thereon in a human cell. The cassette preferably contains homologous or heterologous transcriptional and translational control sequences operably linked to the nucleic acid. Such control sequences include at least a transcription promoter (constitutive or inducible) and transcription termination sequences and can further include other regulatory elements such as transcription enhancers, ribosome binding sequences, splice junction sequences, and the like. In most embodiments, the promoter is a heterologous promoter; however, in particular embodiments, the promoter can the native promoter for the MMP-11. In a particularly useful embodiment, the promoter is the constitutive cytomegalovirus immediate early promoter with or without the intron A sequence (CMV) although those skilled in the art will recognize that any of a number of other known promoters such as the strong immunoglobulin promoter, Rous sarcoma virus long terminal repeat promoter, SV40 small or large T antigen promoter, or the like. Transcriptional terminators include the bovine growth hormone terminator although other known transcriptional terminators such as SV40 termination sequences can also be used. The plasmids pV1JnsB and pV1JnsA, each of which contain the cytomegalovirus (CMV) immediate/early region promoter and enhancer with intron A followed by a cloning site and the BGH polyadenylation signal, are examples of a useful an expression vector. The MMP-11 in any one of the aforementioned embodiments can be cloned into the cloning site to complete the expression cassette.

Commercially available mammalian expression vectors which are suitable for expression of any one of the recombinant polynucleotides disclosed herein include, but are not limited to, pV1JnsA, pV1JnsB, pVAX1 (Invitrogen, Carlsbad, Calif.), pcDNA3.neo (Invitrogen), pcDNA3.1 (Invitrogen), pcDNA3.1/Myc-His (Invitrogen), pCI-neo (Promega, Madison, Wis.), pLITMUS28, pLITMUS29, pLITMUS38 and pLITMUS39 (New England Bioloabs, Beverly, Mass.), pcDNAI, pcDNAIamp (Invitrogen), pcDNA3 (Invitrogen), pMC1neo (Stratagene, La Jolla, Calif.), pXT1 (Stratagene), pSG5 (Stratagene), EBO-pSV2-neo (ATCC 37593) pBPV-1 (8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

Also, a variety of bacterial expression vectors can be used to express any one of the recombinant polynucleotides disclosed herein in bacterial cells. Commercially available bacterial expression vectors which may be suitable for expression include, but are not limited to, pCR2.1 (Invitrogen), pET11a (Novagen, Madison, Wis.), lambda gt11 (Invitrogen), and pKK223-3(Pharmacia).

In addition, a variety of fungal cell expression vectors may be used to express any one of the recombinant polynucleotides disclosed herein in fungal cells. Commercially available fungal cell expression vectors that are suitable for expression include, but are not limited to, pYES2 (Invitrogen) and Pichia expression vector (Invitrogen).

Also, a variety of insect cell expression vectors can be used to express any one of the recombinant polynucleotides disclosed herein in insect cells. Commercially available insect cell expression vectors which can be suitable for expression include, but are not limited to, pBlueBacIII and pBlueBacHis2 (Invitrogen), and pAcG2T (Pharmingen).

Viral vectors that can be used for expression of any one of the recombinant polynucleotides disclosed herein in mammalian cells include, but are not limited to, adenovirus vectors, adeno-associated virus vectors, herpesvirus vectors, Sindbis virus vectors, Similiki forest virus vectors, parvovirus vectors, pox virus vectors (such as vaccinia virus, fowl pox, canary pox, and the like), retrovirus vectors, bacteriophage vectors, and baculovirus vectors. Many of the viral vectors for making recombinant viruses encoding any one of the recombinant polynucleotides herein are commercially available.

In currently preferred embodiments, the viral vector used for making recombinant viruses is an adenoviral or plasmid vector, although linear DNA linked to a promoter, or other vectors, such as adeno-associated virus or a modified vaccinia virus, retroviral or lentiviral vector may also be used. If the vector chosen is an adenovirus, it is currently preferred that the vector be a so-called first-generation adenoviral vector. These adenoviral vectors are characterized by having a non functional E1 gene region, and preferably a deleted adenoviral E1 gene region. In some embodiments, the expression cassette is inserted in the position where the adenoviral E1 gene is normally located. In addition, these vectors optionally have a non-functional or deleted E3 region. It is also preferred that the adenovirus genome used be deleted of both the E1 and E3 regions (AE1AE3).

The adenovirus vectors can be multiplied in known cell lines which express the viral E1 gene, such as 293 cells, or PERC.6 cells, or in cell lines derived from 293 or PERC.6 cell which are transiently or stably transformed to express an extra protein. For examples, when using constructs that have a controlled gene expression, such as a tetracycline regulatable promoter system, the cell line may express components involved in the regulatory system. One example of such a cell line is TRex-293, others are known in the art.

For convenience in manipulating the adenoviral vector, the adenovirus may be in a shuttle plasmid form. This invention is also directed to a shuttle plasmid vector, which comprises a plasmid portion and an adenovirus portion, the adenovirus portion comprising an adenoviral genome which has a deleted E1 and optional E3 deletion, and has an inserted expression cassette comprising a nucleic acid encoding a catalytically inactive MMP-11 polypeptide or catalytically inactive MMP-11 fusion polypeptide. In preferred embodiments, there is a restriction site flanking the adenoviral portion of the plasmid so that the adenoviral vector can easily be removed. The shuffle plasmid may be replicated in prokaryotic cells or eukaryotic cells.

In a currently preferred embodiment of the invention, an expression cassette comprising a nucleic acid encoding any one of the recombinant MMP-11 disclosed herein is inserted into the pMRKAdS-HV0 adenovirus plasmid (See Emini et al., WO0222080). This plasmid comprises an Ads adenoviral genome deleted of the E1 and E3 regions. The design of the pMRKAd5-HV0 plasmid was improved over prior adenovectors by extending the 5' cis-acting packaging region further into the E1 gene to incorporate elements found to be important in optimizing viral packaging, resulting in enhanced virus amplification. Advantageously, this enhanced adenoviral vector is capable of maintaining genetic stability following high passage propagation.

The present invention further provides recombinant host cells transformed or transfected with a vector comprising any one of the recombinant polynucleotides disclosed herein, particularly host cells transformed or transfected with a vector comprising any one of the aforementioned nucleic acid molecules wherein the nucleic acid molecule is operably linked to a promoter. Recombinant host cells include bacteria such as *E. coli*, fungal cells such as yeast, plant cells, mammalian cells including, but not limited to, cell lines of bovine, porcine, monkey, human, or rodent origin; and insect cells including, but not limited to, *Drosophila* and silkworm-derived cell lines. For instance, one insect expression system utilizes *Spodoptera frugiperda* (Sf21) insect cells (Invitrogen) in tandem with a baculovirus expression vector (pAcG2T, Pharmingen, San Diego, Calif.). Also, mammalian species which may be suitable and which are commercially available, include but are not limited to, L cells L-M(TK-) (ATCC CCL-1.3), L cells L-M (ATCC CCL-1.2), Saos-2 cells (ATCC HTB-85), 293 cells (ATCC CRL-1573), Raji cells (ATCC CCL-86), CV-1 cells (ATCC CCL-70), COS-1 cells (ATCC CRL-1650), COS-7 cells (ATCC CRL-1651), CHO-K1 cells (ATCC CCL-61), 3T3 cells (ATCC CCL-92), NIH/3T3 cells (ATCC CRL-1658), HeLa cells (ATCC CCL-2), C1271 cells (ATCC CRL-1616), BS-C-1 cells (ATCC CCL-26), MRC-5 cells (ATCC CCL-171), HEK293T cells (ATCC CRL-1573), ST2 cells (Riken Cell bank, Tokyo, Japan RCB0224), C3H10T1/2 cells (JCRB0602, JCRB9080, JCRB0003, or IFO50415), and CPAE cells (ATCC CCL-209).

As noted above, an expression vector containing any one of the recombinant polynucleotides disclosed herein can be used to express the recombinant MMP-11 encoded therein in a recombinant host cell. Therefore, the present invention provides a process for expressing any one of the recombinant polynucleotides disclosed herein in a recombinant host cell comprising introducing the vector comprising a nucleic acid which encodes the recombinant MMP-11 into a suitable host cell and culturing the host cell under conditions which allow expression any one of the recombinant polynucleotides disclosed herein. The polynucleotide encoding the recombinant MMP-11 is operably linked to a heterologous promoter which can be constitutive or inducible.

Following expression of any one of the recombinant nucleic acids or polynucleotides disclosed herein in a host cell, the recombinant MMP-11 polypeptide can be recovered for use in a polypeptide-based vaccine. Methods for purifying polypeptides are well known in the art and include purification from cell lysates and extracts by various combinations of, or individual application of salt fractionation, ion exchange chromatography, size exclusion chromatography, hydroxylapatite adsorption chromatography, or hydrophobic interaction chromatography. In addition, recombinant MMP-11 can be separated from other cellular polypeptides by use of an immunoaffinity column made with monoclonal or polyclonal antibodies specific for MMP-11 or the immunoenhancing element polypeptide in the case of the MMP-11 fusion polypeptide.

Cloning, expression vectors, transfections and transformations, and protein isolation of expressed proteins are well known in the art and have been described, for example, in Sambrook et al., Molecular Cloning: A Laboratory Manual 2nd Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001).

The anti-MMP-11 vaccines of the present invention include both polynucleotide vaccines encoding any one of the embodiments of recombinant MMP-11 or MMP-11 fusion polypeptides disclosed herein and polypeptide vaccines comprising any one of the embodiments of recombinant MMP-11 or MMP-11 fusion polypeptides disclosed herein. Individuals suffering from invasive carcinomas that overexpress MMP-11 such as those of the breast, colon, head and neck, lung, ovary, pancreas, prostate, skin (basal cell carcinoma), uterus (cervix carcinoma and endometrial carcinoma) or non-invasive carcinomas that have a risk of evolving towards invasion can benefit from immunization by the vaccines of the present invention. The anti-MMP-11 vaccines further include adenovirus anti-MMP-11 vaccines which comprise a recombinant adenovirus having any one of the recombinant polynucleotides disclosed herein.

In its most basic embodiment, the nucleic acid or polynucleotide anti-MMP-11 vaccine comprises any one of the recombinant polynucleotides disclosed herein, for example, a recombinant nucleic acid molecule or polynucleotide encoding anyone of the aforementioned embodiments of the recombinant MMP-11 polypeptides or MMP-11 fusion polypeptides under the control of or operably linked to a suitable heterologous promoter. The encoded recombinant MMP-11 polypeptide can have the amino acid sequence of the MMP-11 polypeptide of any species, including, but not limited to, the MMP-11 from humans; primates such as chimpanzees, Rhesus monkey, Cynomolgus monkey; non-primates such as mouse, rat, dog, and the like. Preferably, the encoded recombinant MMP-11 has the amino acid sequence of the human MMP-11. The following illustrates the currently preferred embodiments of the nucleic acids encoding the MMP-11 for inclusion in the aforementioned gene cassettes and expression vectors for use as a polynucleotide anti-MMP-11 vaccine.

In a preferred embodiment, the MMP-11 encoded by the polynucleotide of the anti-MMP-11 vaccine is catalytically inactive. For example, the catalytically inactive hMMP-11 is shown by the nucleotide sequence in SEQ ID NO:4 wherein the nucleotide codon GAA encoding the conserved glutamic acid at position 216 of the hMMP-11 had been changed to the nucleotide codon GTG encoding the amino acid valine to produce a catalytically inactive hMMP-11 having the amino acid sequence shown in SEQ ID NO:5. While the nucleotide codon encoding the glutamic acid residue was changed to a nucleotide codon encoding valine, the nucleotide codon can also be changed to other amino acids or the histidine residues changed to other amino acids without departing from the invention.

As discussed previously, it has been shown that codon optimization of genes or transcription units coding for particular polypeptides leads to increased expression of the encoded polypeptide, that is increased translation of the mRNA encoding the polypeptide. In the case of a polynucleotide vaccine, the increased expression of the encoded polypeptide produces more of the encoded polypeptide which can lead to increased immunogenecity of the vaccine in vivo, which in turn, can enhance the efficacy of the vaccine. Therefore, in further embodiments, the nucleotide codons encoding the amino acids comprising the MMP-11 are optimized to enhance expression of the MMP-11 and thus, the efficacy of the anti-MMP-11 vaccine. That is, one or more of the nucleotide codons encoding the MMP-11 that occur at low frequency in nucleic acids encoding highly expressed proteins in humans have been replaced with nucleotide codons that occur at a higher frequency in the nucleic acids encoding the highly expressed proteins in humans. The nucleotide sequence of hMMP-11 that is catalytically inactive and in which the codons encoding the catalytically inactive hMMP-11 have undergone codon optimization is shown in SEQ ID NO:6.

The mouse model of the examples show that the efficacy of an anti-MMP-11 vaccine comprising a polynucleotide encoding a catalytically inactive, codon-optimized mouse MMP-11 was enhanced when the carboxy terminal codon of the codons encoding the mMMP-11-opt was linked to codons encoding the immunoenhancing element polypeptide: the *E. coli* LTB. Therefore, in a preferred embodiment of the anti-MMP-11 vaccine, the polynucleotide comprises a nucleic acid encoding the catalytically inactive MMP-11 linked to a polynucleotide encoding an immunoenhancing element polypeptide or substantial portion (MMP-11 fusion polypeptide). In currently preferred embodiments, the polynucleotide comprises a nucleic acid encoding the catalytically inactive MMP-11 linked to a polynucleotide encoding the *E. coli* LTB or substantial portion of such that the polynucleotide encodes an MMP-11-LTB fusion protein. In further embodiments, the polynucleotide encoding the LTB does not include the codons encoding the LTB signal peptide. Currently, it is preferable that the MMP-11 be the hMMP-11. The nucleotide sequence of the *E. coli* LTB without the signal peptide is shown in SEQ ID NO:7 and its amino acid sequence is shown in SEQ ID NO:9. The polynucleotide sequence encoding the *E. coli* LTB without the signal peptide in which the nucleotide codons have been optimized for enhanced expression in humans is shown in SEQ ID NO:8. In a particularly preferred embodiment, the nucleotide codons comprising the polynucleotide encoding the catalytically inactive hMMP-111 and the LTB are optimized for enhanced expression in humans.

While the *E. coli* LTB was the source of the immunoenhancing element polypeptide that was used in the fusion polypeptide embodiments of the anti-MMP-11 vaccines disclosed herein, the present invention further contemplates embodiments comprising polynucleotides encoding fusion polypeptides comprising MMP-11 fused to other immunoenhancing element polypeptides or substantial portions thereof. Examples of immunoenhancing element polypeptides include, but are not limited to, heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and LTB from other bacterial species.

Therefore, in light of the above, the present invention provides a nucleic acid or polynucleotide anti-MMP-11 vaccine which encodes a single fusion polypeptide comprising a catalytically inactive MMP-11 linked to an immunoenhancing element or substantial portion thereof, for example, the *E. coli* LTB. An example of such a vaccine comprises a polynucleotide encoding a polypeptide comprising the amino acid of SEQ ID NO:5 (catalytically inactive hMMP-11) and the amino acid of SEQ ID NO:8 (LTB) or the nucleotide sequence of SEQ ID NO:4 (catalytically inactive hMMP-11) and SEQ ID NO:7 (encoding LTB without signal peptide) or SEQ ID NO: 8 (wherein nucleotide codons encoding the LTB without signal peptide have been optimized for expression in humans), respectively. As an example, the vaccine comprises a polynucleotide that encodes a catalytically inactive hMMP-11-LTB fusion polypeptide having the amino acid sequence shown in SEQ ID NO:10. Such a polypeptide can be encoded by the nucleotide sequence shown in SEQ ID NO:11.

In a preferred embodiment of the polynucleotide anti-MMP-11 vaccine, the nucleotide codons of the polynucleotide encoding the catalytically inactive MMP-11 are optimized for enhanced expression in humans as described above. It is further preferable that the nucleotide codons of the polynucleotide encoding the immunoenhancing element are also enhanced for enhanced expression in humans. An example of such a polynucleotide would comprise the codon-optimized nucleotide sequence of SEQ ID NO:6 encoding the catalytically inactive hMMP-11 and the codon-optimized nucleotide sequence of SEQ ID NO:8 encoding the LTB. As an example, the polynucleotide encoding the codon-optimized, catalytically inactive hMMP-11-LTB fusion polypeptide has the nucleotide sequence shown in SEQ ID NO:12.

The polynucleotide anti-MMP-11 vaccines can be administered by a variety of delivery mechanisms such as direct injection, electroporation, mucosal delivery, and the like. In some preferred embodiments, the vaccine is administered intramuscularly, intranasally, intraperitoneally, subcutaneously, intradermally, bombardment by gene gun, topically, or orally. For example, the vaccine can be administered intramuscularly into the deltoid muscle and can be administered using a 0.5 mL syringe followed by an electrical stimulus within two minutes of the injection. The electrical stimulus can be provided using the MEDPULSER DNA delivery system (Inovio Biomedical Corporation, San Diego, Calif.). Preferably, the polynucleotide anti-MMP-11 vaccines comprise any one of the above polynucleotides in a pharmaceutically acceptable carriers and excipients such as water, saline, dextrose, glycerol, ethanol, and the like, and combinations thereof. In a currently preferred embodiment, the vaccine is formulated in a saline solution. In some cases it is anticipated that the polynucleotide vaccines can comprise the expression vector within a bacterium such as an attenuated strains of *Shigella flexneri, Salmonella* spp., *Yersinia enterocolitica*, or *Listeria monocytogenes*. The polynucleotide anti-MMP-11 vaccines can also contain auxiliary substances such as wetting agents, emulsifying agents, buffers, and the like.

The polynucleotide anti-MMP-11 vaccine can include one or more genetic adjuvants (nucleic acids encoding one or more molecular adjuvants) capable of modulating the immune response towards either a Th1 or Th2 response. Such genetic adjuvants include, but are not limited to, costimulatory molecules such as CD80 and CD86; proinflammatory cytokines such as interleukin-1α (IL-1α); tumor necrosis factor-α and β (TNF-α and TNF-β); Th1 cytokines such as IL-2, IL-12, IL-15, and IL-18; Th2 cytokines such as IL-4, IL-5, and IL-10; macrophage colony-stimulating factor (M-CSF); αgranulocyte colony-stimulating factor (G-CSF); granulocytes-monocyte colony-stimulating factor (GM-CSF); IL-8; interferon-γ-inducible protein-10 (γIP-10); macrophage inhibitory protein-1α (MIP-1α); and RANTES. Sasaki et al., Methods 31: 243-254 (2003), provides a good discussion on adjuvant formulations and delivery systems for DNA vaccines (See also Kim et al., J. Interferon Cytokine Res. 20: 487-498 (2000) and Kim et al., Human Gene Therapy 11: 305-321 (2000)). The genetic adjuvants can be provided in an expression cassette on an expression vector separate from the expression vector encoding the hMMP-11 in any one of the aforementioned embodiments or on the same expression vector encoding the hMMP-11 in any one of the aforementioned embodiments.

The polynucleotide anti-MMP-11 vaccine can include one or more conventional adjuvants. Conventional adjuvants include, but are not limited to, mineral salts such as aluminum phosphate or hydroxide, bacteria-derived adjuvants such as monophosphoryl lipid A, cholera toxin, muramyl-peptides, lipid particles such as cationic liposomes and mannan-coated liposomes, emulsifier adjuvants such as QS-21, and synthetic adjuvants such as ubenimex. Additional adjuvants and excipients can be found in "A Compendium of Vaccine Adjuvants and Excipients ($2^{nd}$ Edition)" by Vogel et al., Vaccine and Prevention Research Program, Division of AIDS, National Institute of Allergy and Infectious Diseases, National Institutes of Health, Bethesda, Md. 20892.

The polynucleotide anti-MMP-11 vaccines of the present invention are preferably administered as a solution or suspension in a pharmaceutically acceptable carrier, at a DNA concentration in the range of about 10 µg/mL to about 5 mg/mL. In general, an immunologically or prophylactically effective dose of about 5 mg, and preferably about 0.05, of a plasmid vaccine vector is administered directly into muscle tissue. The appropriate dosage will depend upon the individual to be vaccinated, and can depend upon the capacity of the individual's ability to express the nucleic acids encoding the hMMP-11 contained in the vaccine and the individual's immune system to react to the expressed hMMP-11. The exact dosage chosen may also depend, in part, upon the judgment of the medical practitioner administering or requesting administration of the vaccine.

The anti-MMP-11 vaccines further include recombinant adenoviruses comprising any one of the aforementioned recombinant polynucleotides. Adenovirus vaccine is currently preferably administered intramuscularly in deltoid diluted in a diluent such as phosphate buffered saline in a final volume of less than about 1 mL. A effective dose of the recombinant adenovirus is generally about $10^6$ to $10^{12}$ viral particles, preferably, about $10^7$ to $10^{11}$ viral particles.

In some embodiments of this invention, the adenovirus and polynucleotide anti-MMP-11 vaccines disclosed herein are used in various prime/boost combinations in order to induce an enhanced immune response. In this case, the two vectors are administered in a "prime and boost" regimen. For example the first type of vector is administered one or more times, then after a predetermined amount of time, for example, 2 weeks, 1 month, 2 months, six months, or other appropriate interval, a second type of vector is administered one or more times. Preferably the vectors carry expression cassettes encoding the same polynucleotide or combination of polynucleotides. In the embodiment where a plasmid vector is also used, it is preferred that the vector contain one or more promoters recognized by mammalian or insect cells. In a preferred embodiment, the plasmid vector would contain a strong promoter such as, but not limited to, the CMV promoter.

As stated above, an adenoviral vector anti-MMP-11 vaccine and a polynucleotide anti-MMP-11 vaccine may be administered to a vertebrate as part of a single therapeutic regime to induce an immune response. In one embodiment, the first vector is a plasmid and the second vector is an adenovirus vector. In an alternative embodiment, the first vector is an adenovirus vector and the second vector is a plasmid. In the method described above, the first type of vector may be administered more than once, with each administration of the vector separated by a predetermined amount of time. Such a series of administration of the first type of vector may be followed by administration of a second type of vector one or more times, after a predetermined amount of time has passed. Similar to treatment with the first type of vector, the second type of vector may also be given one time or more than once, following predetermined intervals of time.

Another embodiment of the present invention is a kit comprising the adenovirus vector or polynucleotide anti-MMP-11 vaccines of the present invention packaged in suitably sterilized containers such as ampules, bottles, vials, and the like, either in multi-dose or in unit-dosage forms. The containers are preferably hermetically sealed after being filled with a vaccine preparation. Preferably, the polynucleotide anti-MMP-11 vaccines are packaged in a container having a label affixed thereto, which label identifies the vaccine, and bears a notice in a form prescribed by a government regulatory agency such as the United States Food and Drug Administration reflecting approval of the vaccine under appropriate laws, dosage information, and the like. The label preferably contains information about the vaccine that is useful to a health care professional administering the vaccine to a patient. The kit also preferably contains printed informational materials relating to the administration of the vaccine, instructions, indications, and any necessary required warnings.

In its most basic embodiment, the anti-MMP-11 polypeptide vaccines of the present invention comprises a catalytically inactive MMP-11 wherein the one or more of the conserved amino acids comprising the zinc binding site H E X X H X X G X X H (SEQ ID NO:3) of the MMP-11 are changed to an alternative amino acid. For example, as shown in SEQ ID NO:5 wherein the conserved glutamic acid at position 216 of the hMMP-11 was changed to the amino acid valine to produce a catalytically inactive MMP-11. Preferably, the catalytically inactive MMP-11 is an MMP-11 fusion polypeptide wherein the MMP-11 is fused or linked at its carboxy terminus to a an immunoenhancing element polypeptide or substantial portion thereof. In currently preferred embodiments, the immunoenhancing element polypeptide is the LTB polypeptide, preferably an LTB in which the signal peptide had been removed, for example, the catalytically inactive MMP-11 shown in SEQ ID NO:5 linked to the LTB polypeptide comprising the amino acid sequence shown in SEQ ID NO:7.

The polypeptide anti-MMP-11 vaccines can be administered by a variety of delivery mechanisms such as direct injection, mucosal delivery, oral delivery, and the like. In some preferred embodiments, the vaccine is administered intramuscularly, intranasally, intraperitoneally, subcutaneously, intradermally, topically, or orally. Preferably, the polynucleotide anti-MMP-11 vaccines are formulated with pharmaceutically acceptable carriers and excipients such as water, saline, dextrose, glycerol, ethanol, and the like, and combinations thereof. The polynucleotide anti-MMP-11 vaccines can also contain auxiliary substances such as wetting agents, emulsifying agents, buffers, and the like. The polypeptide anti-MMP-11 vaccine can include one or more molecular adjuvants capable of modulating the immune response towards either a Th1 or Th2 response. Such molecular adjuvants include, but are not limited to, costimulatory molecules such as CD80 and CD86, proinflammatory cytokines such as interleukin-1α (IL-1α), tumor necrosis factor-α and β (TNF-α and TNF-β), Th1 cytokines such as IL-2, IL-12, IL-15, and IL-18), Th2 cytokines such as IL-4, IL-5, and IL-10, macrophage colony-stimulating factor (M-CSF), granulocyte colony-stimulating factor (G-CSF), granulocytes-monocyte colony-stimulating factor (GM-CSF), IL-8, interferon-γ-inducible protein-10 (γIP-10), macrophage inhibitory protein-1α (MIP-1α), and RANTES. The polypeptide anti-MMP-11 vaccine can include one or more conventional adjuvants. Conventional adjuvants include, but are not limited to, mineral salts such as aluminum phosphate or hydroxide, bacteria-derived adjuvants such as monophosphoryl lipid A, cholera toxin, muramyl peptides, lipid particles such as cationic liposomes and mannan-coated liposomes, emulsifier adjuvants such as QS-21, and synthetic adjuvants such as ubenimex. Additional adjuvants and excipients can be found in aforementioned "A Compendium of Vaccine Adjuvants and Excipients (2$^{nd}$ Edition)" by Vogel et al.

The present invention further provides a method for identifying an analyte for inhibiting a cancer that overexpresses MMP-11, which comprises inducing the cancer in a mouse; administering the analyte to the mouse with the induced cancer; and determining whether the analyte inhibits the cancer in the mouse with the induced tumor, which identifies the analyte for inhibiting a cancer that overexpresses the MMP-11. In particular embodiments, the analyte is determined to bind the MMP-11 before it is administered to the mouse. In further still embodiments, the cancer that is induced in the mouse is a colon cancer, and in further still embodiments, the cancer is induced in the mouse by administering to the mouse 1-2dimethylhydrazine (DMH) in an amount sufficient to induce the cancer in the mouse.

The following examples are provided to further illustrate the features and embodiments of the present invention, and are not meant to be limiting.

EXAMPLE 1

To construct a vector expressing the mouse MMP-11, cDNA was cloned from mouse fibroblast cells, which were part of stromal compartment. Total RNA was extracted from NIH-3T3 cells and oligonucleotides specific for the mouse MMP-11 were used to amplify the cDNA using Polymerase chain reaction (PCR). The PCR primers used were forward 5'-MMP-11, having the nucleotide sequence 5'-CCCGGGGCGG ATGGCACGGG CCGCCTGTC-3' (SEQ ID NO:16) and the degenerated oligonucleotide reverse 3'-MMP-11-1473 having the nucleotide sequence 5'-GTCAGMGGAA AGTRTTGGCA GGCTCAGCAC AG-3' (SEQ ID NO:17) wherein M is A or C and R is A or G. The RT-PCR reaction was performed as follows: 45° C. for 30 minutes; 94° C. for 2 minutes, and then 40 cycles at 94° C. for 15 seconds, 58° C. for 30 seconds, and 68° C. for 2 minutes.

An amplification product of about 1630 bp was obtained and cloned into the TA cloning vector pCR2.1 (Invitrogen, Carlsbad, Calif.) to produce plasmid pCR2.1-MMP-11. DNA sequence analysis the cloned amplification product showed that the DNA sequence of the cloned amplification product was a complete match with the nucleotide sequence for the mouse MMP-11 cDNA (Accession number: NM_008606). The cDNA encoding the mouse MMP-11 was removed from the pCR2.1-MMP-11 by digesting with EcoRI and cloning into the EcoRI site of plasmid vector pV1JnsB to produce expression vector pV1JnsB-MMP-11 (FIG. 1). As shown in FIG. 1, the cDNA encoding MMP-11 is downstream of a human CMV promoter. The PV1j vectors have been described by Montgomery et al. in DNA Cell Biol. 12: 777-783 (1993).

Figure 2:
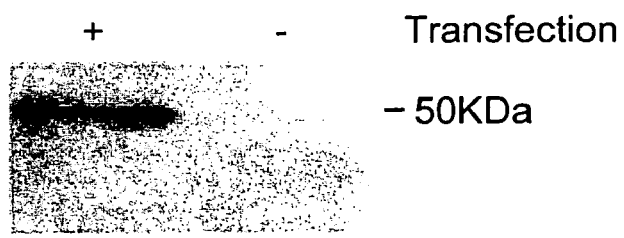
FIG. 2 shows the expression of mouse MMP-11. HeLa cells were transfected with pV1JnsB-MMP-11 and extracts analyzed by western blot. A band corresponding to the molecular weight of MMP-11 was detected.

To verify the expression of MMP-11, HeLa cells were transfected with pV1JnsB-MMP-11. Cell extracts were analyzed by western blot using an antibody for human MMP-11 cross reacting with mouse MMP-11. As shown in FIG. 2, a band of about 50 KDa was detected, indicating that MMP-11 was expressed by the vector.

EXAMPLE 2

It has been shown that codon optimization of genes coding for various types of antigens can lead to increased expression and enhanced immunogenicity in vivo. Therefore, to increase expression and enhance immunogenicity of the mMMP-11, the mMMP-11 coding sequence was codon optimized.

The mMMP-11 cDNA sequence was converted to a polynucleotide sequence encoding the same amino acid sequence but with codon usage optimized for expression in mouse cells (For a general discussion on codon optimization, see Lathe, J. Molec. Biol.: 183: 1-12 (1985)). The methodology generally consisted of identifying codons in the wild-type mMMP-11 polynucleotide sequence that are not commonly associated with highly expressed genes in mice and replacing them with codons commonly associated with highly expressed genes in mice to produce a polynucleotide having only codons commonly associated with highly expressed genes for high expression of the polynucleotide in cells of mouse origin. The new gene sequence was then inspected for undesired sequences generated by these codon replacements (e.g., "ATTTA" sequences, inadvertent creation of intron splice recognition sites, unwanted restriction enzyme sites, high GC content, etc.). Undesirable sequences were eliminated by substitution of the codons comprising the undesirable sequences with other codons, preferably, if practical, with another codon associated with highly expressed genes that codes for the same amino acid. The synthetic gene segments are then tested for improved expression. The codon optimized gene for mouse expression was designed using the Vector NTI program algorithm (InforMax, Rockville, Md.). To increase the level of transcription, an optimized Kozak sequence was inserted 5' to the ATG start codon. Moreover, two consecutive stop codons were inserted downstream of the coding sequence to enhance translation termination.

Figure 6A:
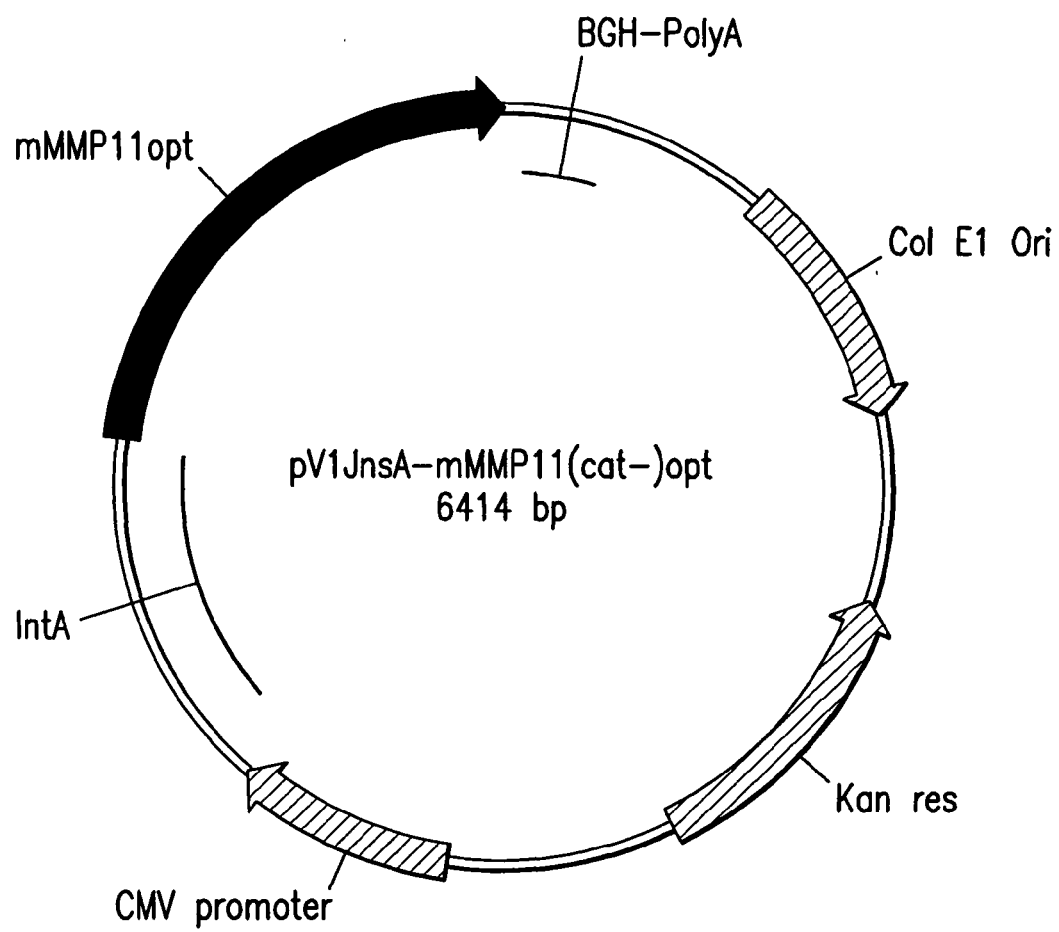
FIG. 6A shows a map of the vector pV1J-mMMP-11(cat-)opt comprising a codon-optimized polynucleotide encoding the catalytically inactive mMMP-11.

The codon-optimized cDNA encoding mMMP-11 was synthesized by oligonucleotide assembly performed at GENEART GmbH, Germany and then cloned into the BglII/SalI site of the pV1JnsA vector, thus generating pV1JnsA-mMMP-11opt. In order to abrogate enzymatic activity of the MMP-11 while not modifying its immunogenic properties, a point mutation was introduced in the catalytic site, which changed the glutamic acid (E) in position 220 to an alanine (A) (Noel et al., Oncogene. 19: 1605-12 (2000)). This produced vector pV1JnsA-mMMP-11(cat-)opt. The nucleotide sequence of the codon-optimized, catalytically inactive variant of mMMP-11 (mMMP-11(cat-)opt) is shown in FIG. 3 (SEQ ID NO:13) and the map for the vector pV1JnsA-mMMP-11(cat-)opt is shown in FIG. 6A.

Figure 6B:
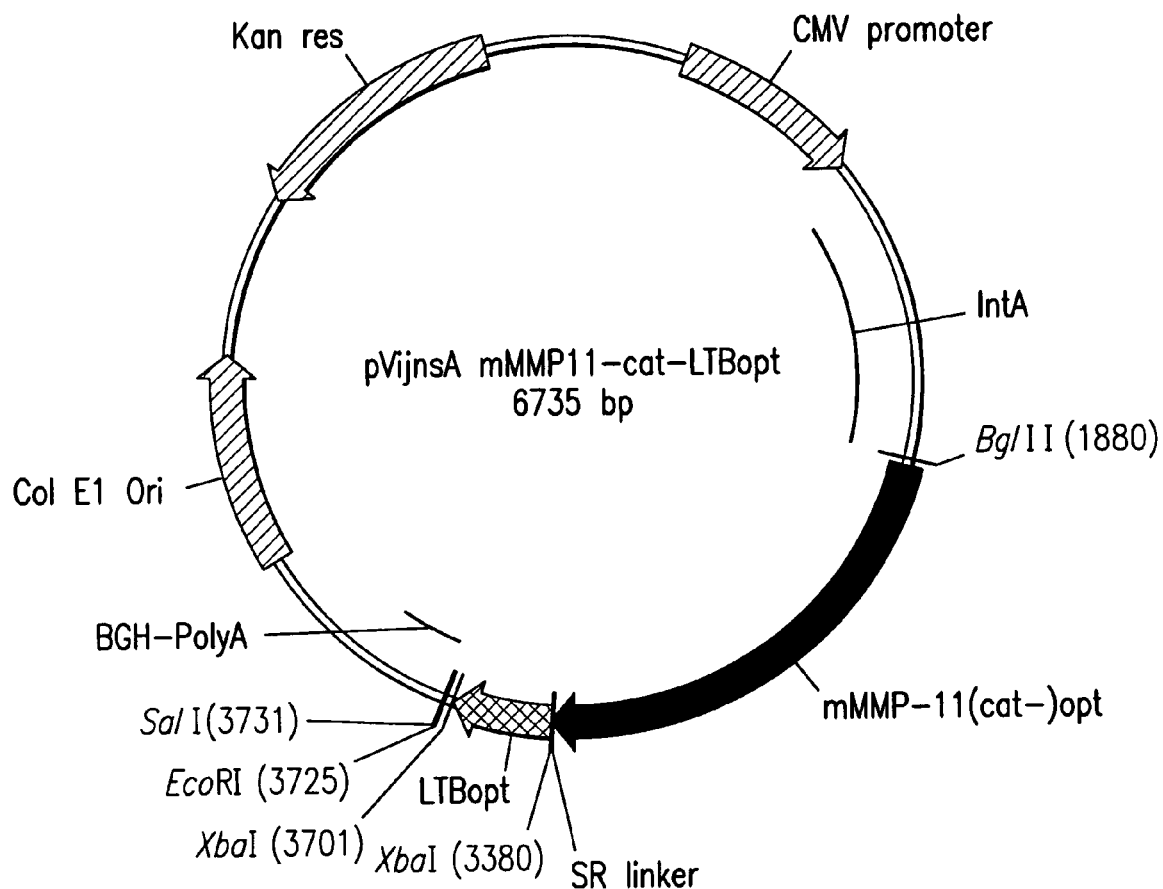
FIG. 6B shows a map of the vector pV1J-mMMP-11(cat-)-LTBopt comprising a codon-optimized polynucleotide encoding the catalytically inactive mMMP-11 linked to the *E. coli* LTB.

WO2005077977 showed that a genetic fusion of the carcinoembryonic antigen (CEA) to immunoenhancing elements such as the heat labile toxin B (LTB) of *E. Coli* further increased the efficacy of vaccination against CEA. Therefore, to enhance the efficacy of the MMP-11, the codon-optimized polynucleotide encoding the catalytically inactive mMMP-11 fused to the *E. coli* LTB with the signal sequence removed was synthesized and cloned into the BglII/SalI site of the pV1JnsA vector, thus generating pV1JnsA-mMMP-11(cat-)-LTBopt (FIG. 6B). The catalytically inactive mMMP-11-LTB fusion was synthesized by oligonucleotide assembly performed at GENEART GmbH, Germany. The codons encoding the LTB were optimized for expression in cells of human origin. FIG. 4 shows the codon-optimized nucleotide sequence encoding the catalytically inactive mMMP-11-LTB fusion polypeptide and FIG. 5 shows the amino acid sequence of the catalytically inactive mMMP-11-LTB fusion polypeptide, respectively.

Figure 7:
FIG. 7 shows a Western blot showing expression of pV1JnsA-MMP-11(cat-)-LTBopt in HeLa cells transfected with the pV1JnsA-MMP-11(cat-)-LTBopt using either anti-MMP-11 or anti-LTB antibodies.

To test the expression of pV1JnsA-mMMP-11(cat-)-LTBopt, HeLa cells were transfected with pV1jnsA-mMMP-11(cat-)-LTBopt by Lipofectamine-2000 (Invitrogen). Whole Cell extracts were prepared using Lysis buffer (2% SDS, 5 mM EGTA, 5 mM EDTA, 20 mM Tris-HCl, pH7.4) and analyzed by Western blot for expression of the catalytically inactive mMMP-11-LTB fusion protein. The catalytically inactive mMMP-11-LTB fusion protein was detected using anti-MMP-11 and anti-LTB antibodies following standard Western blot protocols. Anti-MMP-11 and -LTB antibodies were from BIOMOL (Exter, UK and Plymouth Meeting, Pa., Anti-MMP-11 cat. # SA-371) and Abcam (Cambridge, UK and MA, Anti-*E. Coli* heat labile toxin, cat# ab9199). As shown in FIG. 7, both antibodies bound to a band of about 60 KDa, which corresponded to the molecular weight of the catalytically inactive mMMP-11-LTB fusion protein.

EXAMPLE 3

Figure 8:
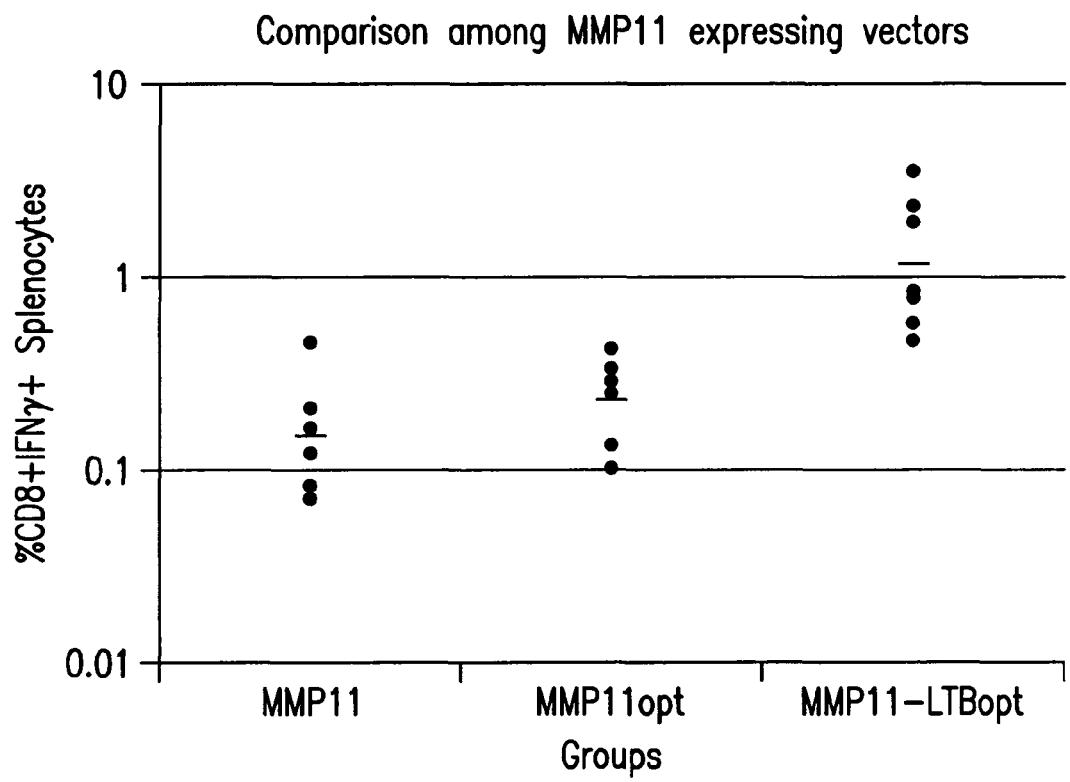
FIG. 8 shows the cell mediated immune response elicited by mMMP-11, mMMP-11opt and mMMP-11(cat-)-LTBopt. Six BALB/c mice were immunized with four weekly injections of DNA electroporation (DNA-EP). Immune response was measured by intracellular staining for IFNγ using peptides covering the C-term of mMMP-11 protein. Dots represent the % CD8+IFNγ+ for each single mouse. Horizontal bar represents the geometric mean of the group.

To test the immunogenic potential of mMMP-11 (cat-)opt and mMMP-11(cat-)-LTBopt as compared to the wild-type mMMP-11, BALB/c mice were each immunized intramuscularly with four DNA injections of 50 µg of plasmid DNA in saline followed by electroporation (EP) 1 week apart, according to Zucchelli et al. (*Enhancing B and T cell Immune response to an HCV E2 DNA vaccine by muscle electro gene transfer*. J. Virol. 74: 11598-11607, (2000)). Two weeks after last injection, mice were sacrificed and the immune response against mMMP-11 peptides was measured by intracellular staining for interferon gamma (IFNγ). As shown in FIG. 8, both wild type and catalytically inactive mMMP-11 opt were efficient to break tolerance in mice (% CD8+IFNγ+>0.1%). There did not appear to be any significant difference between mMMP-11 and catalytically inactive mMMP-11opt. However, as also shown in FIG. 8, fusion of catalytically inactive mMMP-11opt to LTB significantly increased the immune response (p<0.05).

Figure 9:
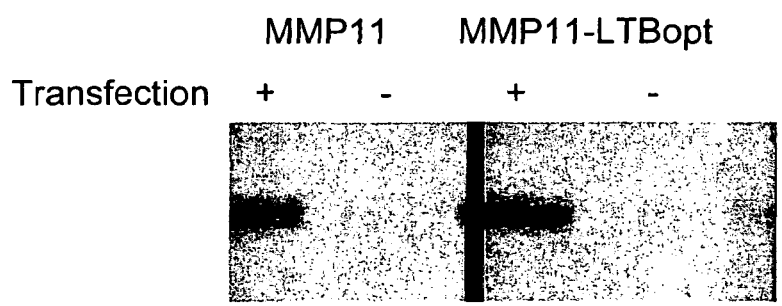
FIG. 9 shows the humoral response elicited by catalytically inactive mMMP-11 and mMMP-11(cat-)-LTBopt. BALB/c mice were immunized with four weekly injections of DNA electroporation (DNA-EP). Presence of antibodies was measured by western blot. Detection of a 50 KDa band corresponding to mMMP-11 indicates a humoral response against mMMP-11.

The humoral response was measured in a Western blot. To measure the humoral immune response, whole cell extracts from HeLa cells transfected with pV1JnsB-MMP-11 were separated on a polyacrylamide gel and transferred onto nitrocellulose membranes. Sera from the above immunized mice were incubated with the membranes. Afterwards, detection of mouse antibodies against mMMP-11 was by using an anti-mouse IgG conjugated with alkaline phosphatases (Sigma Chemicals, St. Louis, Mo.). Detection of a band corresponding to the molecular weight of mMMP-11 indicates the presence of antibodies against mMMP-11. As shown in FIG. 9, no apparent significant difference was observed in the humoral response between mice immunized with mMMP-11 and mice immunized with catalytically inactive mMMP-11(cat-)-LTB opt.

Based on the results shown in FIG. 8, mMMP-11(cat-)-LTBopt was selected as the best immunogen to be used for the vaccination studies.

EXAMPLE 4

A tumor model overexpressing MMP-11 was produced as follows. 1,2-dimethylhydrazine (DMH) or its metabolite azoxymethane are often used as the initiating carcinogen in tumor-induction studies. DMH has been found to induce colonic tumors in numerous species of animals (Choudhary and H. Hansen, Chemosphere 37: 801-843 (1998)), even after a single oral exposure in some cases, but typically 6 to 10 weekly treatments are used. DMH is an alkylating agent and treatment with this chemical has been shown to induce methyl adducts to DNA bases, point mutations, micronuclei, and sister chromatid exchanges. Treatment with DMH induces apoptosis in the colon (Blakey et al., Cancer Res. 45: 242-249 (1985)) as well as an increase in cellular proliferation of colonic epithelial cells (Ma et al., World J. Gastroenterol. 8: 847-852 (2002)), which is a characteristic of human colon cancer.

Figure 10:
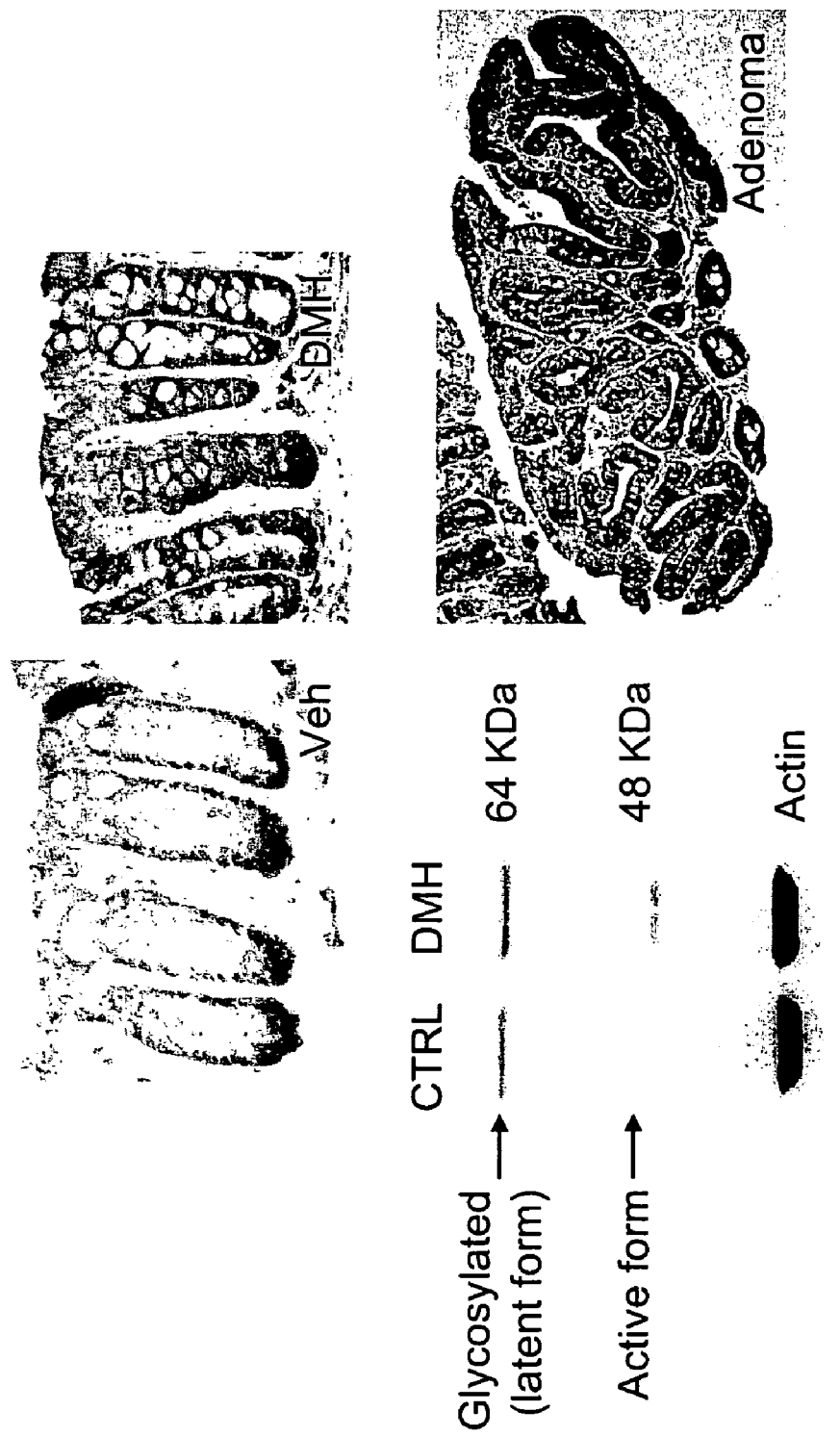
FIG. 10 shows mMMP-111 is overexpressed in Mouse Colon Adenomas induced by DMH. A/J mice were treated with six IP injections of DMH. Five weeks later, colon tissue is analyzed by IHC and western blotting. Veh means vehicle (PBS).

In susceptible mouse strains, such as A/J, but also to a lesser extent BALB/c, DMH induced carcinogenesis progression in colon tissue goes through different stages: (1) aberrant crypt formation (ACF); (2) Adenoma; (3) Polyp; and (4) Adenocarcinoma. In order to verify the expression of mMMP-11 in this process of tumorigenesis, A/J mice received six weekly injections of DMH and were sacrificed five weeks after last DMH injection: at this stage both aberrant crypts and some adenomas were present in mouse colon tissue. Gut tissue was frozen and analyzed by western blot and immunohistochemistry (IHC) using an antibody against mMMP-11. In untreated mice (vehicle), IHC analysis showed expression of mMMP-11 at the basis of normal crypt: it appears that expression of mMMP-11 was limited to colonic stem cells. Strong and diffused expression was detected in aberrant crypt and adenoma formations (FIG. 10). This observation was confirmed by western blot analysis of colon tissue extracts from mice treated with DMH or left untreated: the activated form of mMMP-11 was present in DMH treated colon (FIG. 10), thus indicating overexpression of the proteinase by the tumorous tissue. These data indicate the suitability of DMH induced carcinogenesis as model for anti-MMP-11 therapy and vaccination.

EXAMPLE 5

This example shows the therapeutic efficacy of anti-MMP-11 vaccine. As shown in the previous example, MMP-11 is overexpressed in aberrant crypt formations (ACF) and adenomas induced by the administration of 1-2dimethylhydrazine (DMH) in A/J mice. Other studies have demonstrated that DMH does not interfere with the immune system and efficacy of genetic vaccination. The following experiment was performed to determine whether DMH would interfere with the functionality of the immune system and efficacy of genetic vaccination.

Figure 19A:
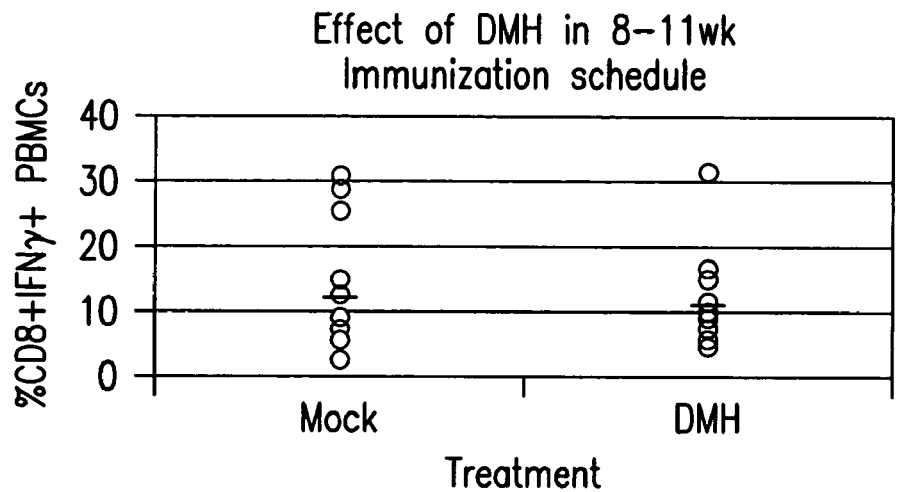
FIG. 19A shows that DMH does not interfere with the CD8+ immune response of BALB/c mice.
Figure 19B:
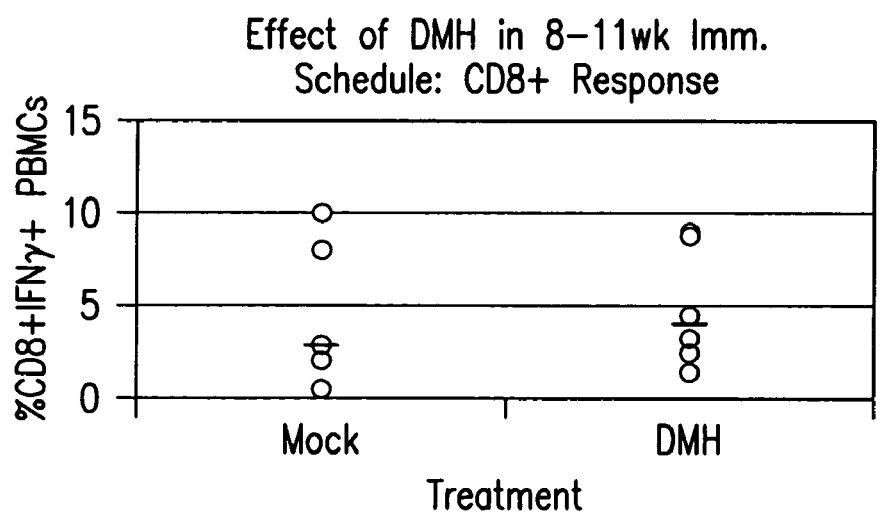
FIG. 19B shows that DMH does not interfere with the CD8+ immune response of A/J mice.
Figure 19C:
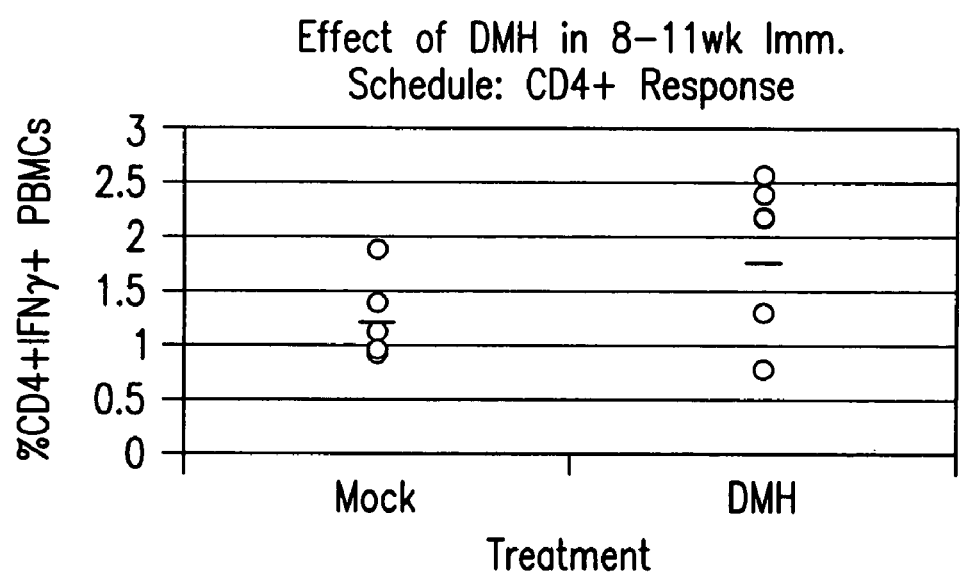
FIG. 19C shows that DMH does not interfere with the CD4+ immune response of A/J mice.

Groups of 10 BALB/c or A/J mice were treated with six intraperitoneal (IP) injections of DMH starting from the fifth week of age or left untreated (Mock). At weeks eight and 11, all of the mice received injections of 50 µg of the plasmid pV1J-CEAopt (See WO2005077977 for pV1J-CEAopt). Two weeks later, the mice were bled and their immune responses to the CEA encoded by pV1J-CEAopt analyzed by intracellular staining upon stimulation with $15^{mer}$ peptides covering CEA protein. For the BALB/c mice, the CD8+ immune response was measured. FIG. 19A shows that there was no significant difference in CD8+ response between DMH-treated and mock-treated BALB/c mice. For the A/J mice, the CD8+ and CD4+ immune responses were measured. FIGS. 19B and 19C show that there was no significant difference in CD8+ and CD4+ responses between DMH-treated and mock-treated A/J mice. These results demonstrated that DMH did not appear to influence the immune system activity. Taken together, these data suggested that MMP-11 is a tumor associated antigen and that a vaccine against MMP-11 would be feasible means for treating cancers that overexpress MMP-11.

Figure 11A:
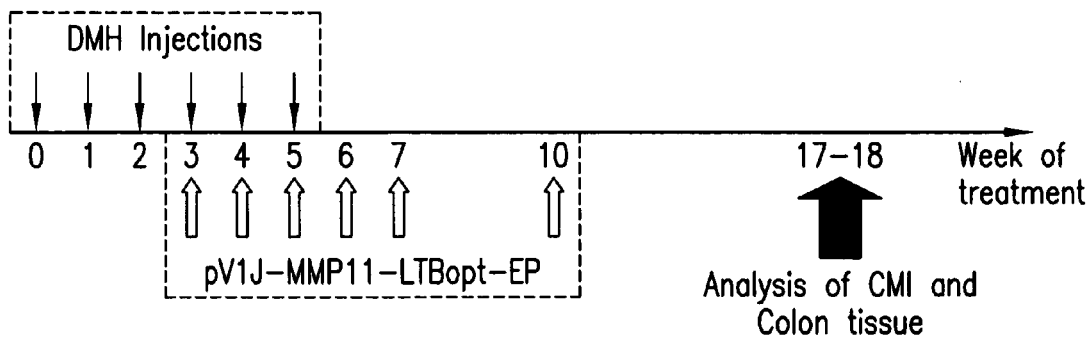
FIG. 11A shows a schematic representation of the experiment performed to demonstrate therapeutic efficacy of the mMMP-11(cat-)-LTBopt genetic vaccine for preventing colon cancer. A/J mice were treated with six IP injections of DMH. A group of mice was left untreated (naive), a second group was vaccinated with the 50 µg of the plasmid pV1J-mMMP-11(cat-)-LTBopt. Seven to eight weeks after the last DMH injection, mice were sacrificed and colon analyzed at microscope for aberrant crypt formation (ACF) (FIGS. 11B and 11C), polyps (FIG. 11D), and adenomas (FIG. 11E).
Figure 11B:
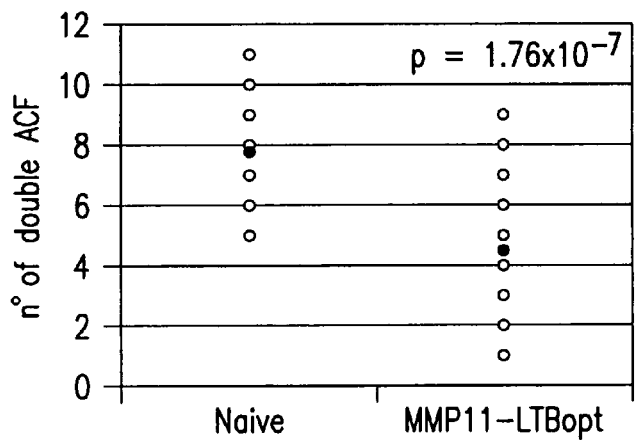
FIG. 11B shows the therapeutic efficacy of the mMMP-11 (cat-)-LTBopt genetic vaccine in inhibiting ACF. Open dots indicate the number of formations per mouse; filled-in dot indicates the geometric mean of the group. Statistic analysis (T student's test) is indicated.
Figure 11C:
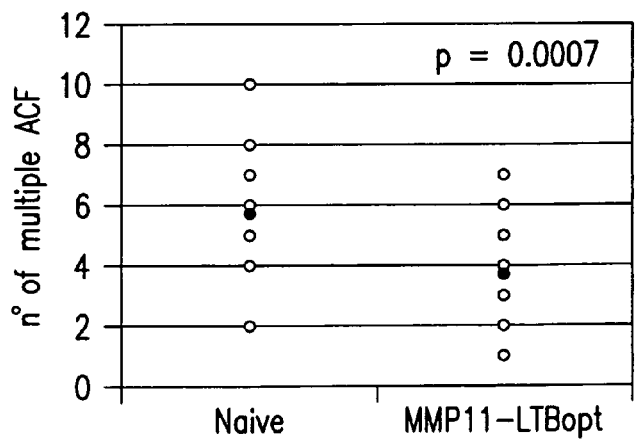
FIG. 11C shows the therapeutic efficacy of the mMMP-11 (cat-)-LTBopt genetic vaccine in inhibiting ACF. Open dots indicate the number of formations per mouse; filled-in dot indicates the geometric mean of the group. Statistic analysis (T student's test) is indicated.
Figure 11D:
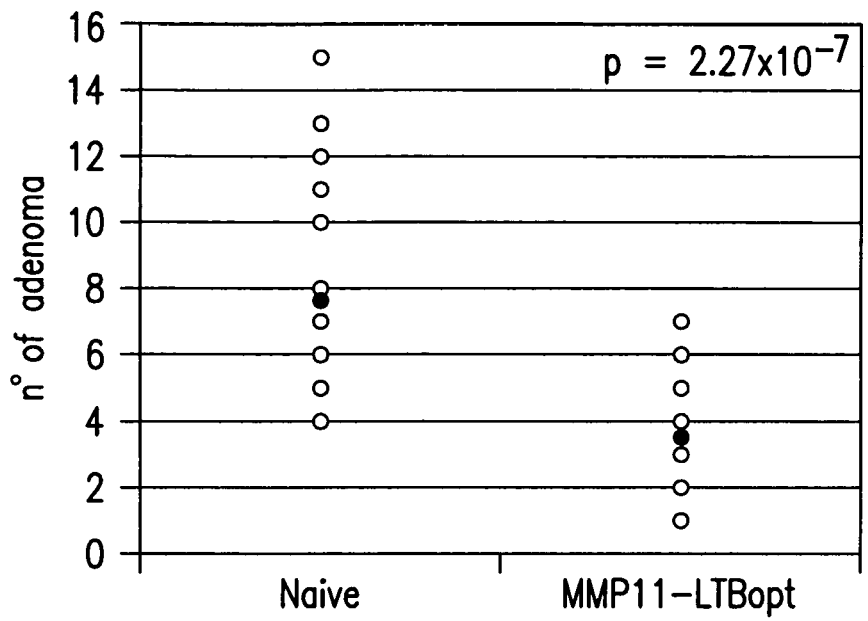
FIG. 11D shows the therapeutic efficacy of the mMMP-11 (cat-)-LTBopt genetic vaccine in inhibiting polyps. Open dots indicate the number of formations per mouse; filled-in dot indicates the geometric mean of the group. Statistic analysis (T student's test) is indicated.
Figure 11E:
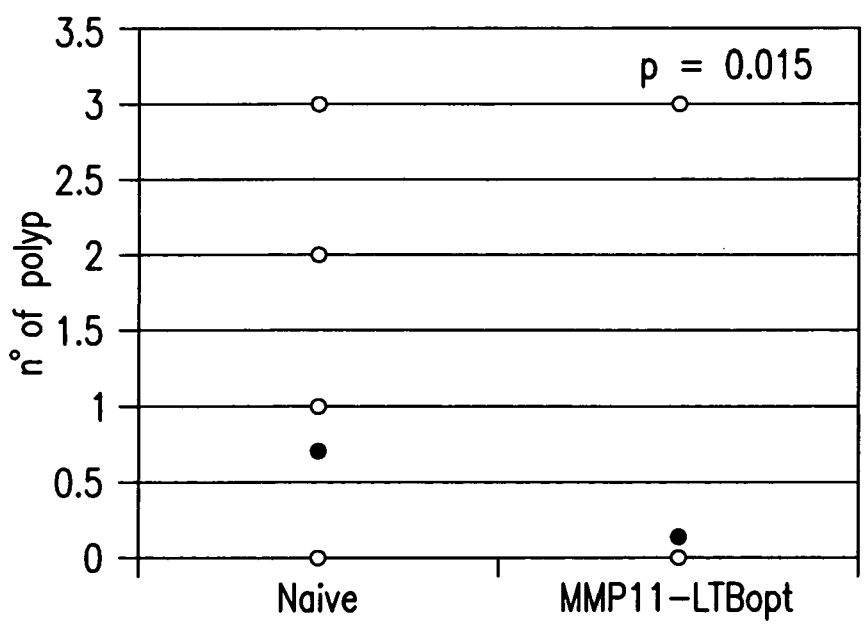
FIG. 11E shows the therapeutic efficacy of the mMMP-11 (cat-)-LTBopt genetic vaccine in inhibiting adenomas. Open dots indicate the number of formations per mouse; filled-in dot indicates the geometric mean of the group. Statistic analysis (T student's test) is indicated.

To test efficacy of an anti-MMP-11 vaccine, groups of 60 A/J mice were treated with DMH with six weekly injections: one group is left untreated (Naïve), a second group is immunized with pV1jnsA-mMMP-11(cat-)-LTBopt followed by electroporation, as indicated in the scheme shown in FIG. 11A. Two weeks after the last immunization, cell-mediated immunity (CMI) against mMMP-11 was analyzed with pool of 15mer peptides encompassing the entire protein; however, poor immune-response was detected in the analyzed groups (data not shown). Seven to eight weeks after the last injection of DMH, 20 mice per group were sacrificed and the colon was analyzed for the presence of ACF, Adenomas, polyps, and adenocarcinomas. Vaccinated mice show significant reduction of DMH-induced presence of ACF, Adenomas, polyps, and adenocarcinomas (FIGS. 11B to 11E).

EXAMPLE 6

To confirm the efficacy of tumor protection in DMH carcinogenesis model in another mouse strain, the same treatment and immunization scheme as above was followed using BALB/c mice. Two weeks after the last immunization, CMI against mMMP-11 was analyzed with a pool of 15mer peptides encompassing the entire protein.

For preparation of splenocytes from immunized mice, spleens were removed from sacrificed mice in a sterile manner and disrupted by scratching through a grid. Erythrocyte lysis was obtained by incubation for 10 minutes with ACK lysing buffer (Life Technologies, Bethesda, Md.). After centrifugation at 1200 rpm for 10 minutes, white cells were resuspended in R10 medium. About 1 to $2 \times 10^6$ splenocytes or PBMC (peripheral blood mononuclear cells) were resuspended in 1 mL R10 medium. Antigen peptides were added to a final concentration of 1 µg/mL with Brefeldin A. The mMMP-11 antigen peptides comprised a pool of 15mer peptides, which together encompassed the entire MMP-11 peptide. The total number of peptides was 121 and was divided in 4 pools (A, from 1 to 30; B, from 31 to 60; C, from 61 to 90; D, from 91 to 121).

After 12 hours incubation at 37° C., the cells were washed with 3 mL FACS buffer (PBS supplemented with either 1% FBS and containing 0.05% $NaN_3$) and centrifuged for 10 minutes at room temperature. The cells were incubated with anti-mouse CD16/CD32 in 100 µL FACS buffer for 15 minutes at 4° C. Then, after washing the cells with FACS buffer, the cells were analyzed for the secretion of IFNγ upon incubation with 15mer mMMP-11 antigen peptides.

For surface antigen staining, allophycocyanin (APC) conjugated anti-mouse CD3☐ phycoerythrin (PE) conjugated anti-mouse CD4, and peridininchlorophyll protein (PerCP) conjugated anti-mouse CD8α, all diluted 1:50 in FACS buffer, were added to the cells in 100 µL final volume and the cells incubated for 30 minutes at room temperature in the dark. After washing with PERMWASH (Pharmingen), cells were resuspended in 100 µL of CYTOFIX-CYTOPERM solution (Pharmingen), vortexed, and incubated for 20 minutes at 4° C. in the dark.

For intracellular staining, the cells were incubated with fluorescein (FITC) conjugated anti-mouse interferon-γ diluted 1:50 in PermWash (100 µL final volume) for 30 minutes at room temperature in the dark. After washing, the cells were resuspended in 250 to 300 µL 1% formaldehyde in PBS and analyzed with a FACS CALIBER (Becton Dickinson, San Jose, Calif.).

Figure 12A:
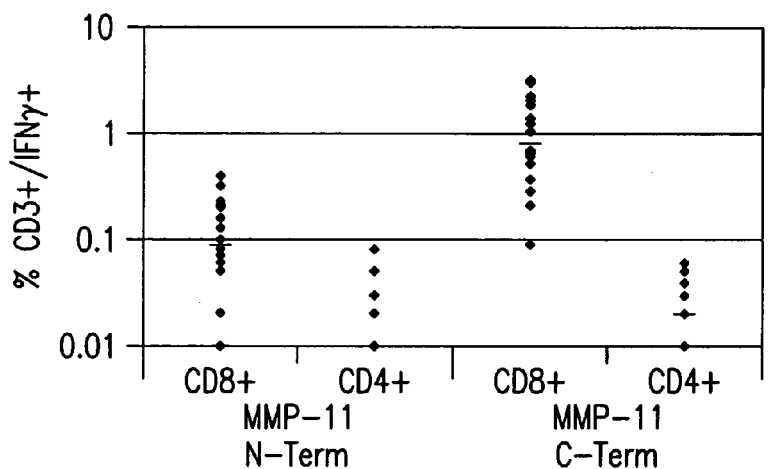
FIG. 12A shows the immune response elicited by anti-mMMP-11 genetic vaccine. BALB/c mice were treated with six IP injections of DMH. A group of mice was left untreated (naive) and a second group was vaccinated with the 50 µg of the plasmid pV1J-mMMP-11(cat-)-LTBopt. The immune response was measured by intracellular staining for IFNγ. Black dots represent the % CD8+ IFNγ+ for each single mouse. Horizontal bar represents the geometric mean of the group.
Figure 12B:
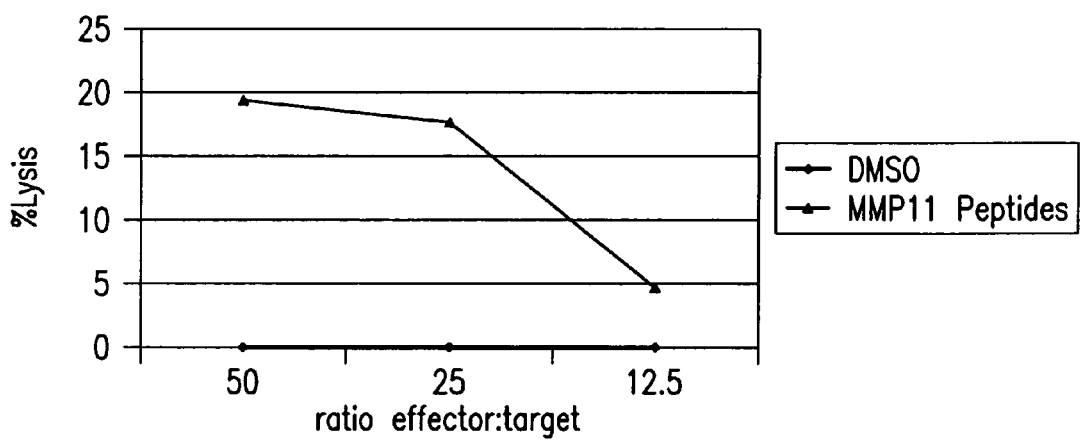
FIG. 12B shows the immune response elicited by anti-mMMP-11 genetic vaccine. BALB/c mice were treated with six IP injections of DMH. A group of mice was left untreated (naive) and a second group was vaccinated with the 50 g of the plasmid pV1J-mMMP-11(cat-)-LTBopt. The immune response was measured using a CTL assay wherein effectors cells were stimulated for seven days with mMMP-11 peptides. p815 mastocytoma cells unloaded or loaded with mMMP-11 peptides were used as target.
Figure 13A:
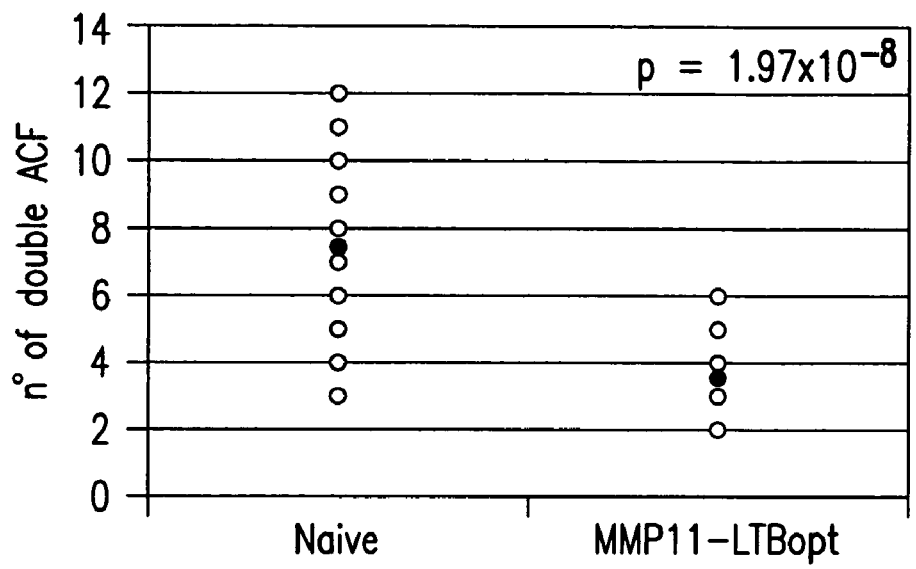
FIG. 13A shows the therapeutic efficacy of mMMP-11 (cat-)-LTBopt genetic vaccine in BALB/c mice in inhibiting ACF. Seven to eight weeks after the last DMH injection, mice were sacrificed and colon analyzed at microscope for ACF. Open dots indicate number of formations per mouse; filled-in dots indicate the geometric mean of the group. Statistic analysis (T student's test) is indicated.
Figure 13B:
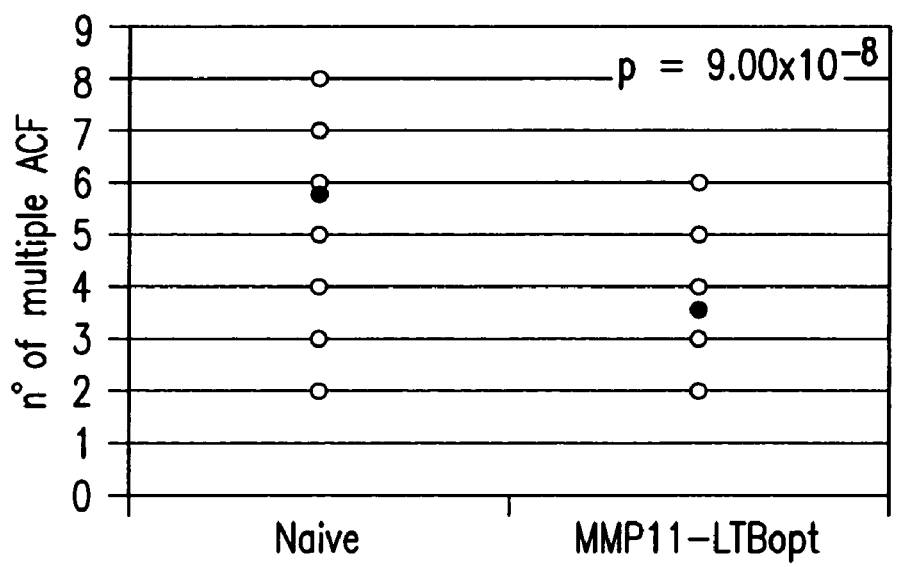
FIG. 13B shows the therapeutic efficacy of mMMP-11 (cat-)-LTBopt genetic vaccine in BALB/c mice in inhibiting ACF. Seven to eight weeks after the last DMH injection, mice were sacrificed and colon analyzed at microscope for ACF. Open dots indicate number of formations per mouse; filled-in dots indicate the geometric mean of the group. Statistic analysis (T student's test) is indicated.
Figure 13C:
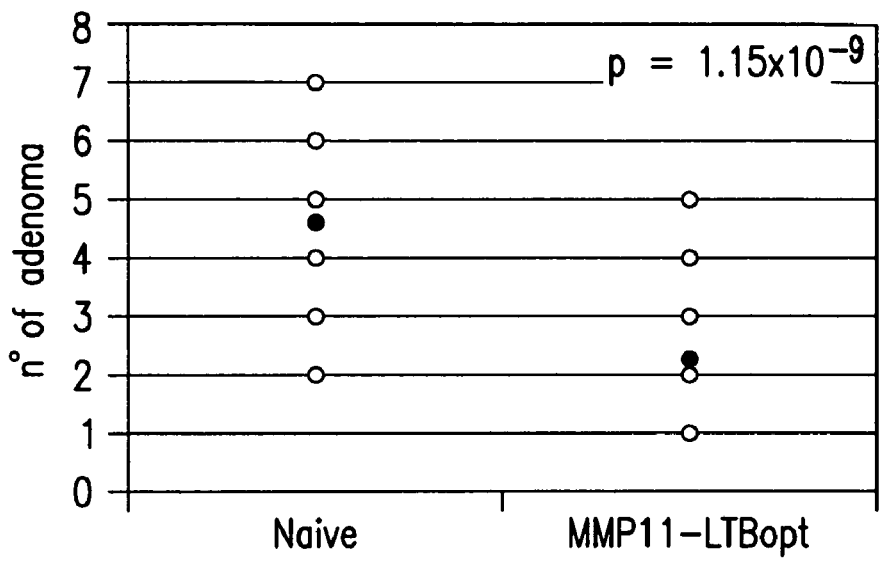
FIG. 13C shows the therapeutic efficacy of mMMP-11 (cat-)-LTBopt genetic vaccine in BALB/c mice in inhibiting polyps. Seven to eight weeks after the last DMH injection, mice were sacrificed and colon analyzed at microscope for polyps. Open dots indicate number of formations per mouse; filled-in dots indicate the geometric mean of the group. Statistic analysis (T student's test) is indicated.
Figure 13D:
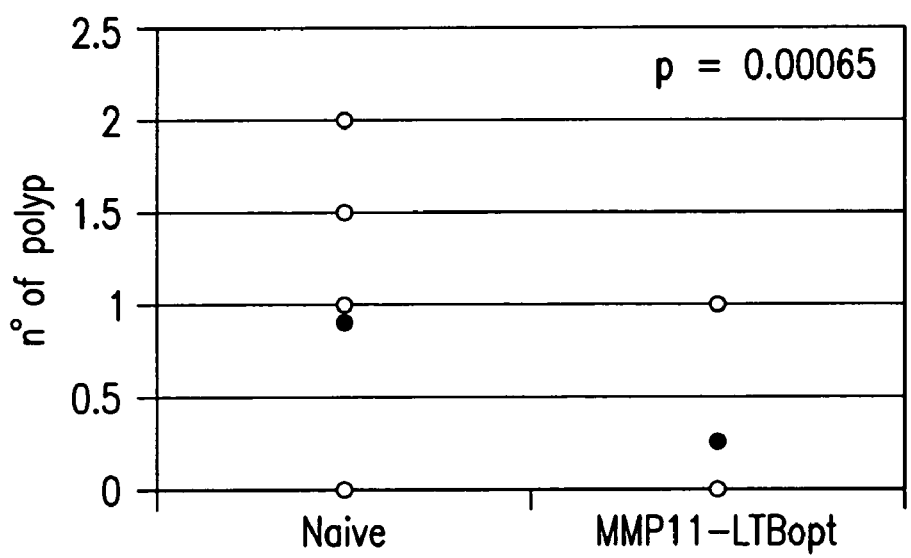
FIG. 13D shows the therapeutic efficacy of mMMP-11 (cat-)-LTBopt genetic vaccine in BALB/c mice in inhibiting adenomas. Seven to eight weeks after the last DMH injection, mice were sacrificed and colon analyzed at microscope for adenomas. Open dots indicate number of formations per mouse; filled-in dots indicate the geometric mean of the group. Statistic analysis (T student's test) is indicated.

A significant immune-response was detected in the immunized groups mainly directed against C-term of the protein and was CD8+ specific (FIG. 12A). Elicited CD8+ effectors were functional since they were able to lyse tumorous target cells loaded with mMMP-11 antigen peptides (FIG. 12B). Most importantly, highly significant protection in vaccinated mice was observed at all stages from ACF to adenomas (FIGS. 13A to 13D). These data indicate that MMP-11 is an optimal target for active specific immunotherapy and genetic vaccination is extremely efficient in tumor protection.

EXAMPLE 7

Cloning and optimization of nucleotide sequence encoding catalytically inactive human MMP-11.

Similar to the mouse MMP-11, the human MMP-11 was codon optimized according to human cell most frequent codon usage and rendered catalytically inactive by changing the codon for the glutamic acid (E) in the catalytic site in position 220 with an alanine (A). The polynucleotide comprising the codon-optimized, catalytically inactive hMMP-11 was synthesized by oligonucleotide assembly (GENEART, GmbH) and cloned into the BglII/EcoRI site of the vector pV1JnsA, generating pV1JnsA-hMMP-11(cat-)opt (FIG. 18). The nucleotide sequence of the codon-optimized polynucleotide encoding the catalytically inactive hMMP-11 is shown in FIG. 14. The amino acid sequence of the catalytically inactive hMMP-11 is shown in FIG. 15. Vector pV1JnsA-hMMP-11(cat-)opt was designed for use in humans and may be used in preclinical models such as mice transgenic for human MHC class I, such as HLA-A2.1 to identify immunogenic epitopes.

Figure 20:
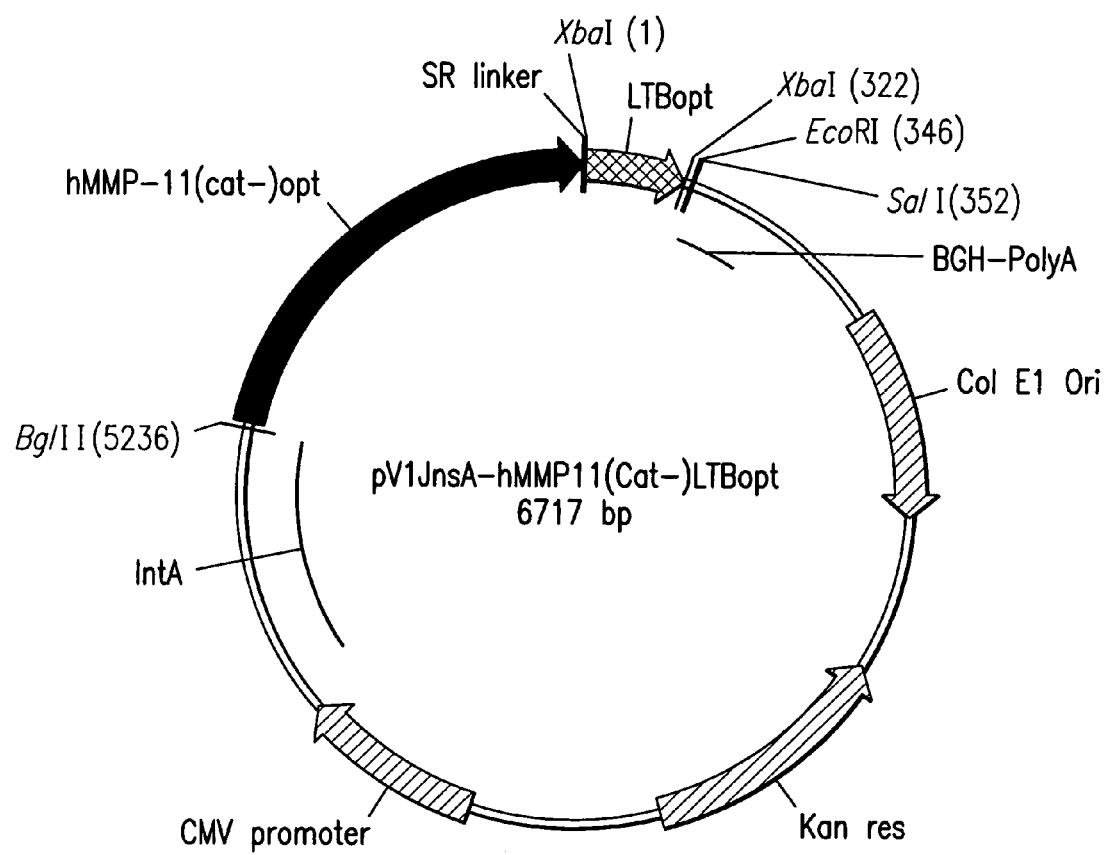
FIG. 20 shows a map of the vector pV1J-hMMP-11(cat-)-LTBopt (See SEQ ID NO:2) comprising a codon-optimized polynucleotide encoding the catalytically inactive hMMP-11 linked to the *E. coli* LTB.

To improve efficacy of the anti-MMP-11 vaccine comprising the hMMP-11, the codon-optimized polynucleotide encoding the catalytically inactive hMMP-11 fused to the *E. coli* LTB with the signal sequence removed is synthesized and cloned into the BglII/SalI site of the pV1JnsA vector, thus generating pV1JnsA-MMP-11(cat-)-LTBopt (FIG. 20). The nucleotide sequence of pV1JnsA-MMP-11(cat-)-LTBopt is shown in SEQ ID NO:2. The nucleotide sequence starts at the second nucleotide of the XbaI polylinker separating the nucleotide codons encoding the catalytically inactive hMMP-11 from the nucleotide codons encoding the LTB. In the nucleotide sequence of SEQ ID NO:2, the CMV promoter includes nucleotides 3647 to 4261, intron A includes nucleotides 4396 to 5221, catalytically inactive hMMP-11 includes nucleotides 5253 to 6715, the XbaI polylinker includes nucleotides 6715 to 5, the LTB includes nucleotides 6 to 315, and the BGH polyA includes nucleotides 382 to 599. The polynucleotide encoding catalytically inactive human MMP-11-LTB fusion can be synthesized by oligonucleotide assembly, which can be performed at GENEART GmbH, Germany.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. An isolated nucleic acid comprising a nucleotide sequence encoding a human matrix metalloproteinase 11 (MMP-11) protein, said protein comprising the sequence of amino acids as set forth in SEQ ID NO:5, wherein one or more of the nucleotide codons have been optimized for enhanced expression of the nucleic acid in cells of human origin.

2. The nucleic acid of claim 1 wherein the nucleotide sequence comprises the nucleotide sequence of SEQ ID NO:6.

3. An isolated nucleic acid encoding a fusion polypeptide having a matrix metalloproteinase 11 (MMP-11) linked to a subunit B of heat labile toxin (LTB) of *E. coli* wherein the LTB does not include a signal peptide and wherein the LTB is encoded by the nucleotide sequence as set forth in SEQ ID NO:8.

4. The nucleic acid of claim 3 wherein the MMP-11 includes a mutation that renders it catalytically inactive.

5. The nucleic acid of claim 3 wherein the MMP-11 is encoded by the nucleotide sequence shown in SEQ ID NO:6.

6. The nucleic acid of claim 3 wherein the fusion polypeptide is encoded by the nucleotide sequence shown in SEQ ID NO:12.

7. An expression vector comprising the nucleic acid of claim 3 operably linked to a promoter.

8. An isolated host cell containing the expression vector of claim 7 therein.

9. A process for expressing an MMP-11 fusion protein in an isolated host cell, comprising culturing the host cell of claim 8 in a cell culture medium under conditions for producing the fusion polypeptide.

* * * * *